US011696752B2

(12) United States Patent
Viola

(10) Patent No.: US 11,696,752 B2
(45) Date of Patent: Jul. 11, 2023

(54) SYSTEMS AND METHODS FOR ALL-INSIDE SUTURE FIXATION FOR IMPLANT ATTACHMENT AND SOFT TISSUE REPAIR

(71) Applicant: Stryker Corporation, Kalamazoo, MI (US)

(72) Inventor: Paul Viola, Montvale, NJ (US)

(73) Assignee: Stryker Corporation, Kalamazoo, MI (US)

( * ) Notice: Subject to any disclaimer, the term of this patent is extended or adjusted under 35 U.S.C. 154(b) by 118 days.

(21) Appl. No.: 17/161,028

(22) Filed: Jan. 28, 2021

(65) Prior Publication Data
US 2021/0145432 A1    May 20, 2021

Related U.S. Application Data

(63) Continuation of application No. 15/604,071, filed on May 24, 2017, now Pat. No. 10,932,769.
(Continued)

(51) Int. Cl.
*A61B 17/04*        (2006.01)
*A61B 17/06*        (2006.01)

(52) U.S. Cl.
CPC ...... *A61B 17/0401* (2013.01); *A61B 17/0469* (2013.01); *A61B 17/06066* (2013.01);
(Continued)

(58) Field of Classification Search
CPC ............ A61B 17/0401; A61B 17/0469; A61B 17/06066; A61B 17/06109;
(Continued)

(56) References Cited

U.S. PATENT DOCUMENTS 3,103,666 A    9/1963   Bone
3,399,432 A    9/1968   Merser
(Continued)

FOREIGN PATENT DOCUMENTS

CN       105078522 A      11/2015
DE    102010060899 A1      5/2012
(Continued)

OTHER PUBLICATIONS

Arthrotek, "Hand Instruments, HP High Performance, PS Precision Series," Arthrotek, a Biomet Company, Arthrotek, Inc. (Warsaw, IN), (2000), 3 pages.
(Continued)

*Primary Examiner* — Erich G Herbermann
(74) *Attorney, Agent, or Firm* — Lerner David LLP

(57) ABSTRACT

In one embodiment, the present invention is a system for repairing a meniscus including: a suture assembly including a first anchor, a second anchor, and a flexible suture connecting the first anchor and the second anchor, the flexible suture including a slide knot between the first anchor and the second anchor; and an inserter including a needle having a longitudinal extending bore and an open distal end, the bore being configured to receive the first anchor and the second anchor, a housing operatively connected to a proximal end of the needle, the housing having a lumen and a slot, the slot including a first portion, a second portion, a first shoulder and a second shoulder and a pusher configured to rotate and slide within the lumen of the housing and the longitudinal extending bore of the needle, the pusher having an extension extending through the slot and configured to be maneuverable through the first portion and second portion and engageable with the first shoulder and second shoulder.

18 Claims, 48 Drawing Sheets

Related U.S. Application Data

(60) Provisional application No. 62/370,167, filed on Aug. 2, 2016, provisional application No. 62/341,744, filed on May 26, 2016.

(52) U.S. Cl.
CPC ............ *A61B 17/06109* (2013.01); *A61B 2017/0404* (2013.01); *A61B 2017/0409* (2013.01); *A61B 2017/0417* (2013.01); *A61B 2017/0445* (2013.01); *A61B 2017/0464* (2013.01); *A61B 2017/0474* (2013.01); *A61B 2017/0475* (2013.01); *A61B 2017/061* (2013.01)

(58) Field of Classification Search
CPC .... A61B 2017/0404; A61B 2017/0409; A61B 2017/0417; A61B 2017/0445; A61B 2017/0464; A61B 2017/0474; A61B 2017/0475; A61B 2017/061; A61B 17/0483; A61B 17/04; A61B 2017/0477
See application file for complete search history.

(56) References Cited

U.S. PATENT DOCUMENTS

| | | |
|---|---|---|
| 3,527,223 A | 9/1970 | Shein |
| 3,845,772 A | 11/1974 | Smith |
| 3,875,648 A | 4/1975 | Bone |
| 4,235,238 A | 11/1980 | Ogiu et al. |
| 4,493,323 A | 1/1985 | Albright et al. |
| 4,669,473 A | 6/1987 | Richards et al. |
| 4,705,040 A | 11/1987 | Mueller et al. |
| 4,741,330 A | 5/1988 | Hayhurst |
| 4,836,205 A | 6/1989 | Barrett |
| 4,994,074 A | 2/1991 | Bezwada et al. |
| 5,085,661 A | 2/1992 | Moss |
| 5,176,691 A | 1/1993 | Pierce |
| 5,312,422 A | 5/1994 | Trott |
| 5,380,334 A | 1/1995 | Torrie et al. |
| 5,391,182 A | 2/1995 | Chin |
| 5,405,352 A | 4/1995 | Weston |
| 5,417,691 A | 5/1995 | Hayhurst |
| 5,437,680 A | 8/1995 | Yoon |
| 5,443,475 A | 8/1995 | Auerbach et al. |
| 5,467,786 A | 11/1995 | Allen et al. |
| 5,470,337 A | 11/1995 | Moss |
| 5,549,631 A | 8/1996 | Bonutti |
| 5,562,684 A | 10/1996 | Kammerer |
| 5,562,689 A | 10/1996 | Green et al. |
| 5,569,305 A | 10/1996 | Bonutti |
| 5,601,557 A | 2/1997 | Hayhurst |
| 5,601,558 A | 2/1997 | Torrie et al. |
| 5,601,571 A | 2/1997 | Moss |
| 5,601,576 A | 2/1997 | Garrison |
| 5,626,614 A | 5/1997 | Hart |
| 5,649,947 A | 7/1997 | Auerbach et al. |
| 5,667,513 A | 9/1997 | Torrie et al. |
| 5,702,462 A | 12/1997 | Oberlander |
| 5,718,717 A | 2/1998 | Bonutti |
| 5,759,189 A | 6/1998 | Ferragamo et al. |
| 5,801,848 A | 9/1998 | Kafri |
| 5,810,848 A | 9/1998 | Hayhurst |
| 5,895,395 A | 4/1999 | Yeung |
| 5,928,252 A | 7/1999 | Steadman et al. |
| 5,941,439 A | 8/1999 | Kammerer et al. |
| 5,976,127 A | 11/1999 | Lax |
| 5,980,559 A | 11/1999 | Bonutti |
| 6,039,753 A | 3/2000 | Meislin |
| 6,047,826 A | 4/2000 | Kalinski et al. |
| 6,056,760 A | 5/2000 | Koike et al. |
| 6,066,146 A | 5/2000 | Carroll et al. |
| 6,071,292 A | 6/2000 | Makower et al. |
| 6,156,044 A | 12/2000 | Kammerer et al. |
| 6,206,895 B1 | 3/2001 | Levinson |
| 6,287,317 B1 | 9/2001 | Makower et al. |
| 6,293,961 B2 | 9/2001 | Schwartz et al. |
| 6,306,156 B1 | 10/2001 | Clark |
| 6,306,159 B1 | 10/2001 | Schwartz et al. |
| 6,319,263 B1 | 11/2001 | Levinson |
| 6,319,271 B1 | 11/2001 | Schwartz et al. |
| 6,432,123 B2 | 8/2002 | Schwartz et al. |
| 6,488,691 B1 | 12/2002 | Carroll et al. |
| 6,491,707 B2 | 12/2002 | Makower et al. |
| 6,500,195 B2 | 12/2002 | Bonutti |
| 6,554,845 B1 | 4/2003 | Fleenor et al. |
| 6,572,635 B1 | 6/2003 | Bonutti |
| 6,592,609 B1 | 7/2003 | Bonutti |
| 6,626,916 B1 | 9/2003 | Yeung et al. |
| 6,635,073 B2 | 10/2003 | Bonutti |
| 6,656,182 B1 | 12/2003 | Hayhurst |
| 6,730,112 B2 | 5/2004 | Levinson |
| 6,884,249 B2 | 4/2005 | May et al. |
| 6,932,826 B2 | 8/2005 | Chan |
| 6,955,683 B2 | 10/2005 | Bonutti |
| 6,972,027 B2 | 12/2005 | Fallin et al. |
| 6,997,933 B2 | 2/2006 | Bittar |
| 7,004,959 B2 | 2/2006 | Bonutti |
| 7,025,756 B2 | 4/2006 | Frazier et al. |
| 7,033,380 B2 | 4/2006 | Schwartz et al. |
| 7,056,325 B1 | 6/2006 | Makower et al. |
| 7,066,944 B2 | 6/2006 | Laufer et al. |
| 7,087,073 B2 | 8/2006 | Bonutti |
| 7,108,700 B2 | 9/2006 | Chan |
| 7,118,583 B2 | 10/2006 | O'Quinn et al. |
| 7,150,750 B2 | 12/2006 | Damarati |
| 7,153,312 B1 | 12/2006 | Torrie et al. |
| 7,192,431 B2 | 3/2007 | Hangody et al. |
| 7,318,833 B2 | 1/2008 | Chanduszko |
| 7,320,701 B2 | 1/2008 | Haut et al. |
| 7,347,863 B2 | 3/2008 | Rothe et al. |
| 7,361,180 B2 | 4/2008 | Saadat et al. |
| 7,390,329 B2 | 6/2008 | Westra et al. |
| 7,390,332 B2 | 6/2008 | Selvitelli et al. |
| 7,594,922 B1 | 9/2009 | Goble et al. |
| 7,601,165 B2 | 10/2009 | Stone |
| 7,601,659 B2 | 10/2009 | Bomberger et al. |
| 7,608,092 B1 | 10/2009 | Schaffhausen |
| 7,608,098 B1 | 10/2009 | Stone et al. |
| 7,621,925 B2 | 11/2009 | Saadat et al. |
| 7,645,286 B2 | 1/2010 | Catanese, III et al. |
| 7,651,509 B2 | 1/2010 | Bojarski et al. |
| 7,658,751 B2 | 2/2010 | Stone et al. |
| 7,736,374 B2 | 6/2010 | Vaughan et al. |
| 7,749,250 B2 | 7/2010 | Stone et al. |
| 7,846,181 B2 | 12/2010 | Schwartz et al. |
| 7,857,830 B2 | 12/2010 | Stone et al. |
| 7,887,551 B2 | 2/2011 | Bojarski et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,959,650 B2 | 6/2011 | Kaiser et al. |
| 7,993,405 B2 | 8/2011 | Cauthen, III et al. |
| 8,034,090 B2 | 10/2011 | Stone et al. |
| 8,057,511 B2 | 11/2011 | Flores et al. |
| RE43,143 E | 1/2012 | Hayhurst |
| 8,088,130 B2 | 1/2012 | Kaiser et al. |
| 8,118,836 B2 | 2/2012 | Denham et al. |
| 8,128,640 B2 | 3/2012 | Harris et al. |
| 8,137,382 B2 | 3/2012 | Denham et al. |
| 8,202,282 B2 | 6/2012 | Schmieding et al. |
| 8,216,252 B2 | 7/2012 | Vaughan et al. |
| 8,216,253 B2 | 7/2012 | Saadat et al. |
| 8,231,654 B2 | 7/2012 | Kaiser et al. |
| 8,236,009 B2 | 8/2012 | Saadat et al. |
| 8,241,305 B2 | 8/2012 | Stone |
| 8,251,998 B2 | 8/2012 | Hoeppner et al. |
| 8,257,394 B2 | 9/2012 | Saadat et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,308,765 B2 | 11/2012 | Saadat et al. |

(56) References Cited

U.S. PATENT DOCUMENTS

| | | |
|---|---|---|
| 8,317,825 B2 | 11/2012 | Stone |
| 8,323,315 B2 | 12/2012 | Schwartz et al. |
| 8,337,525 B2 | 12/2012 | Stone et al. |
| 8,343,227 B2 | 1/2013 | Metzger et al. |
| 8,361,113 B2 | 1/2013 | Stone et al. |
| 8,366,744 B2 | 2/2013 | Bojarski et al. |
| 8,409,253 B2 | 4/2013 | Stone et al. |
| 8,444,657 B2 | 5/2013 | Saadat et al. |
| 8,460,319 B2 | 6/2013 | Wales et al. |
| 8,500,818 B2 | 8/2013 | Metzger et al. |
| 8,506,597 B2 | 8/2013 | Kaiser et al. |
| 8,512,374 B2 | 8/2013 | Schwartz et al. |
| 8,512,375 B2 | 8/2013 | Torrie et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,574,235 B2 | 11/2013 | Stone |
| 8,597,327 B2 | 12/2013 | Stone et al. |
| 8,623,051 B2 | 1/2014 | Bojarski et al. |
| 8,632,569 B2 | 1/2014 | Stone et al. |
| 8,652,153 B2 | 2/2014 | Brady et al. |
| 8,696,704 B2 | 4/2014 | Selvitelli et al. |
| 8,790,369 B2 | 7/2014 | Orphanos et al. |
| 8,808,309 B2 | 8/2014 | Nelson et al. |
| 8,814,902 B2 | 8/2014 | Bonutti |
| 8,814,903 B2 | 8/2014 | Sengun et al. |
| 8,814,904 B2 | 8/2014 | Bennett |
| 8,828,027 B2 | 9/2014 | Vaughan et al. |
| 8,828,052 B2 | 9/2014 | Caborn et al. |
| 8,828,054 B2 | 9/2014 | Caborn et al. |
| 8,834,524 B2 | 9/2014 | Torrie et al. |
| 8,876,842 B2 | 11/2014 | Marshall et al. |
| 8,926,634 B2 | 1/2015 | Rothe et al. |
| 8,961,538 B2 | 2/2015 | Koogle, Jr. et al. |
| 9,084,597 B2 | 7/2015 | Arai et al. |
| 9,173,645 B2 | 11/2015 | Overes et al. |
| 9,173,651 B2 | 11/2015 | Stone et al. |
| 9,173,653 B2 | 11/2015 | Bojarski et al. |
| 9,220,493 B2 | 12/2015 | Hart et al. |
| 9,220,494 B2 | 12/2015 | Bojarski et al. |
| 9,247,935 B2 | 2/2016 | George et al. |
| 9,277,914 B2 | 3/2016 | Wales et al. |
| 9,289,201 B2 | 3/2016 | Schwartz et al. |
| 9,295,461 B2 | 3/2016 | Bojarski et al. |
| 9,332,980 B2 | 5/2016 | George et al. |
| 9,351,722 B2 | 5/2016 | Koogle, Jr. et al. |
| 2002/0019649 A1 | 2/2002 | Sikora et al. |
| 2002/0107532 A1 | 8/2002 | Huet-Olivier et al. |
| 2002/0116012 A1 | 8/2002 | May et al. |
| 2002/0143342 A1 | 10/2002 | Hangody et al. |
| 2002/0193811 A1 | 12/2002 | Chan |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0036797 A1 | 2/2003 | Malaviya et al. |
| 2003/0036801 A1 | 2/2003 | Schwartz et al. |
| 2003/0049299 A1 | 3/2003 | Malaviya et al. |
| 2003/0078617 A1 | 4/2003 | Schwartz et al. |
| 2003/0130694 A1 | 7/2003 | Bojarski et al. |
| 2003/0158604 A1 | 8/2003 | Cauthen et al. |
| 2003/0181928 A1 | 9/2003 | Vidlund et al. |
| 2003/0204194 A1 | 10/2003 | Bittar |
| 2003/0236535 A1 | 12/2003 | Onuki et al. |
| 2004/0002734 A1 | 1/2004 | Fallin et al. |
| 2004/0015186 A1 | 1/2004 | Bittar |
| 2004/0127915 A1 | 7/2004 | Fleenor et al. |
| 2004/0138683 A1 | 7/2004 | Shelton et al. |
| 2004/0153074 A1 | 8/2004 | Bojarski et al. |
| 2004/0166169 A1 | 8/2004 | Malaviya et al. |
| 2004/0225183 A1 | 11/2004 | Michlitsch et al. |
| 2004/0243178 A1 | 12/2004 | Haut et al. |
| 2004/0249395 A1 | 12/2004 | Mikkaichi et al. |
| 2004/0254598 A1 | 12/2004 | Schumacher et al. |
| 2004/0260343 A1 | 12/2004 | Leclair |
| 2005/0033325 A1 | 2/2005 | May et al. |
| 2005/0033363 A1 | 2/2005 | Bojarski et al. |
| 2005/0090840 A1 | 4/2005 | Gerbino et al. |
| 2005/0113851 A1 | 5/2005 | Swain et al. |
| 2005/0131313 A1 | 6/2005 | Mikulka et al. |
| 2005/0159762 A1 | 7/2005 | Nuutinen et al. |
| 2005/0165418 A1 | 7/2005 | Chan |
| 2005/0187577 A1 | 8/2005 | Selvitelli et al. |
| 2005/0283192 A1 | 12/2005 | Torrie et al. |
| 2005/0283246 A1 | 12/2005 | Cauthen et al. |
| 2006/0025819 A1 | 2/2006 | Nobis et al. |
| 2006/0030884 A1 | 2/2006 | Yeung et al. |
| 2006/0064126 A1 | 3/2006 | Fallin et al. |
| 2006/0074438 A1 | 4/2006 | Chan |
| 2006/0100643 A1 | 5/2006 | Laufer et al. |
| 2006/0161183 A1 | 7/2006 | Sauer |
| 2006/0178680 A1* | 8/2006 | Nelson ............... A61B 17/0467 606/139 |
| 2006/0189993 A1 | 8/2006 | Stone |
| 2006/0190042 A1 | 8/2006 | Stone et al. |
| 2006/0265042 A1 | 11/2006 | Catanese et al. |
| 2006/0293709 A1 | 12/2006 | Bojarski et al. |
| 2007/0027476 A1 | 2/2007 | Harris et al. |
| 2007/0049929 A1 | 3/2007 | Catanese et al. |
| 2007/0073316 A1* | 3/2007 | Sgro .................... A61B 17/068 606/151 |
| 2007/0083236 A1 | 4/2007 | Sikora et al. |
| 2007/0088390 A1 | 4/2007 | Paz et al. |
| 2007/0142846 A1 | 6/2007 | Catanese et al. |
| 2007/0173865 A1 | 7/2007 | Oren et al. |
| 2007/0213746 A1 | 9/2007 | Hahn et al. |
| 2007/0219567 A1 | 9/2007 | Bayer et al. |
| 2007/0270889 A1 | 11/2007 | Conlon et al. |
| 2008/0009904 A1 | 1/2008 | Bourque et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033487 A1 | 2/2008 | Schwartz et al. |
| 2008/0033488 A1 | 2/2008 | Catanese et al. |
| 2008/0039872 A1 | 2/2008 | Catanese et al. |
| 2008/0039893 A1 | 2/2008 | McLean et al. |
| 2008/0188893 A1 | 8/2008 | Selvitelli et al. |
| 2009/0062854 A1 | 3/2009 | Kaiser et al. |
| 2009/0255544 A1 | 10/2009 | Cox |
| 2010/0010497 A1 | 1/2010 | Goble et al. |
| 2010/0094425 A1 | 4/2010 | Bentley et al. |
| 2010/0114161 A1 | 5/2010 | Bojarski et al. |
| 2010/0130989 A1* | 5/2010 | Bourque ............ A61B 17/0482 606/144 |
| 2011/0009872 A1 | 1/2011 | Mistry et al. |
| 2011/0172701 A1 | 7/2011 | Wales et al. |
| 2012/0316648 A1* | 12/2012 | Lambrecht ......... A61B 17/0401 623/17.16 |
| 2013/0030463 A1 | 1/2013 | Harris et al. |
| 2013/0131809 A1* | 5/2013 | Michielli ............... A61F 2/4455 623/17.16 |
| 2013/0144314 A1 | 6/2013 | Bojarski et al. |
| 2013/0144337 A1 | 6/2013 | Stone et al. |
| 2013/0204276 A1 | 8/2013 | Stone et al. |
| 2013/0211452 A1 | 8/2013 | Stone et al. |
| 2014/0135835 A1 | 5/2014 | Stone et al. |
| 2014/0214053 A1 | 7/2014 | Bourque et al. |
| 2014/0243858 A1 | 8/2014 | Bourque et al. |
| 2014/0276987 A1 | 9/2014 | Saliman |
| 2014/0296913 A1 | 10/2014 | Orphanos et al. |
| 2014/0350599 A1 | 11/2014 | Torrie et al. |
| 2015/0066061 A1 | 3/2015 | Caborn et al. |
| 2015/0190129 A1 | 7/2015 | Nelson et al. |
| 2015/0223803 A1 | 8/2015 | Trawick |
| 2016/0022261 A1 | 1/2016 | Stone et al. |

(56) References Cited

U.S. PATENT DOCUMENTS

2016/0120535 A1 5/2016 Ferragamo et al.
2016/0120536 A1 5/2016 Bojarski et al.

FOREIGN PATENT DOCUMENTS

| EP | 0129442 A1 | 12/1984 |
|---|---|---|
| EP | 0241240 A2 | 10/1987 |
| EP | 0415915 A1 | 3/1991 |
| EP | 0702933 A1 | 3/1996 |
| EP | 1408848 A1 | 4/2004 |
| EP | 1685802 A1 | 8/2006 |
| EP | 2098172 A1 | 9/2009 |
| EP | 2277457 A1 | 1/2011 |
| GB | 2118474 A | 11/1983 |
| JP | 2004508128 A | 3/2004 |
| JP | 2004515273 A | 5/2004 |
| WO | 8603666 A1 | 7/1986 |
| WO | 8701270 A1 | 3/1987 |
| WO | 2004037094 A2 | 5/2004 |
| WO | 2006086275 A2 | 8/2006 |
| WO | 2008021691 A2 | 2/2008 |
| WO | 2009014996 A2 | 1/2009 |
| WO | 2009124215 A1 | 10/2009 |
| WO | 2012072244 A1 | 6/2012 |
| WO | 1399671 A1 | 7/2013 |
| WO | 2014039610 A1 | 3/2014 |

OTHER PUBLICATIONS

Borden, Peter, et al., "Biomechanical Comparison of the FasT-Fix Meniscal Repair Suture System with Vertical Mattress Sutures and Meniscus Arrows," The American Journal of Sports Medicine, American Orthopaedic Society for Sports Medicine, vol. 31 (No. 3), p. 374-378. May-Jun. 2003.
David Caborn, M.D., "Meniscal Repair with the FasT-Fix Suture System," A Smith & Nephew Technique Plus Illustrated Guide, Smith & Nephew (Andover, MA), (2002), 12 pages.
De Beer, J.F. et al.: 'Nicky's Knot—A New Slip Knot for Arthroscopic Surgery' Arthroscopy: The Journal of Arthroscopic and Relate Surgery vol. 14, No. 1, Jan.-Feb. 1998, pp. 109-110.
Extended European Search Report for Application No. EP17173055.9 dated Oct. 20, 2017.
Field, M.H. et al.: 'Technical Note: A 'New' Arthroscopic Sliding Knot' Orthopedic Clinics of North America vol. 32, No. 3, Jul. 2001, pp. 525-526.
Fleega, B.A. et al.: 'The Giant Knot: A New One-Way Self-Locking Secured Arthroscopic Slip Knot' Arthroscopy: The Journal of Arthroscopic and Relate Surgery vol. 15, No. 4, May-Jun. 1999, pp. 451-452.
Fromm, Stuart E., "Surgical Technique for Repair of Meniscal Tears," RapidLoc Meniscal Repair System, Mitek Products (Rapid City, South Dakota), (2001), 6 pages.
Harris et al., U.S. Appl. No. 60/650,131, filed Feb. 7, 2005, titled "System and method for all-inside suture fixation for implant attachment and soft tissue repair".
International Search Report and Written Opinion Issued in PCT/US2007/074491, dated Aug. 6, 2008.
International Search Report issued in PCT/US06/04039, dated Sep. 13, 2007, 3 pages.
Israelsson, L.A. et al. "Physical Properties of Self Locking and Conventional Surgical Knots", European Journal of Surgery, Jul. 1994, vol. 160 (6-7) (Abstract Only).
Japanese Office Action dated May 13, 2011, for Japanese Patent Application No. 2007-554285 with translation.
Kim, S. et al.: 'Arthroscopic Knot Tying' Techniques in Shoulder & Elbow Surgery vol. 4, No. 2, Jun. 2003, pp. 35-43.
Kim, S. et al.: 'The SMC Knot—A New Slip Knot With Locking Mechanism' Arthroscopy: The Journal of Arthroscopic and Relate Surgery vol. 16, No. 5, Jul.-Aug. 2000, pp. 563-565.
Nottage, W.M. et al.: 'Arthroscopic Knot Tying Techniques' Arthroscopy: The Journal of Arthroscopic and Relate Surgery vol. 15, No. 5, Jul.-Aug. 1999, pp. 515-521.
Pallia, C.S.: 'The PC Knot: A Secure and Satisfying Arthroscopic Slip Knot' Arthroscopy: The Journal of Arthroscopic and Relate Surgery vol. 19, No. 5, May-Jun. 2003, pp. 558-560.
Patent Examination Report for Application No. AU 2007284219 dated Aug. 18, 2012, 4 pages.
Stone et al. Regeneration of Meniscal Cartilage with Use of a Collagen Scaffold, Analysis of Preliminary Data. The Journal of Bone and Joint Surgery Dec. 1997, 79-A(12); 1770-1777; Abstract.
Supplementary European Search Report dated Apr. 12, 2013, for EP 06720310, 4 pages.
Supplementary European Search Report dated Apr. 25, 2013, for EP 07799856, 3 pages.
Supplementary European Search Report for Application No. 16173415.7 dated Jan. 16, 2017.
Weston, P. V. "A New Clinch Knot", Obstetrics & Gynecology, Jul. 1991, vol. 78, pp. 144-147.
Wiley, W.B. et al.: 'The Tuckahoe Knot: A Secure Locking Slip Knot' Arthroscopy: The Journal of Arthroscopic and Relate Surgery vol. 20, No. 5, May-Jun. 2004, pp. 556-559.
Written Opinion of the International Search Authority in PCT/US06/04039, dated Sep. 13, 2007, 5 pages.

\* cited by examiner

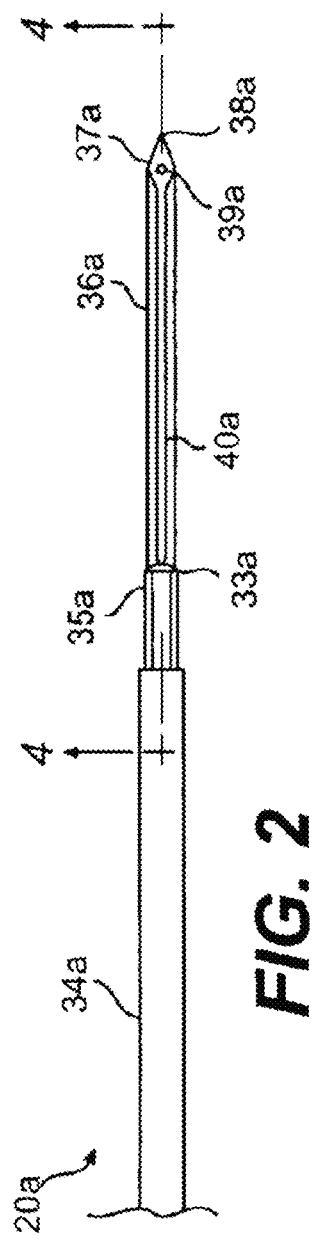
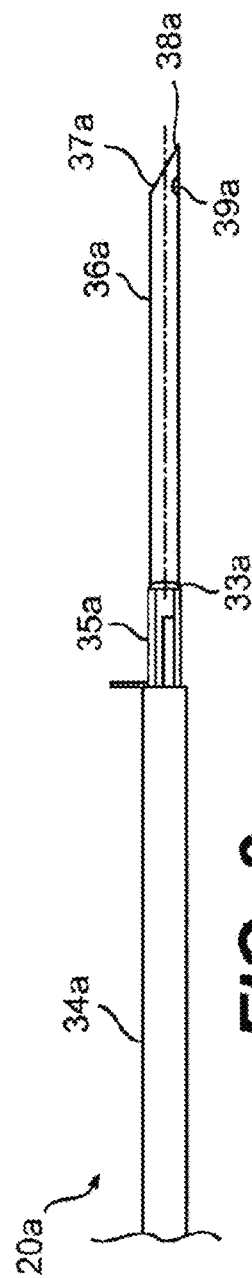
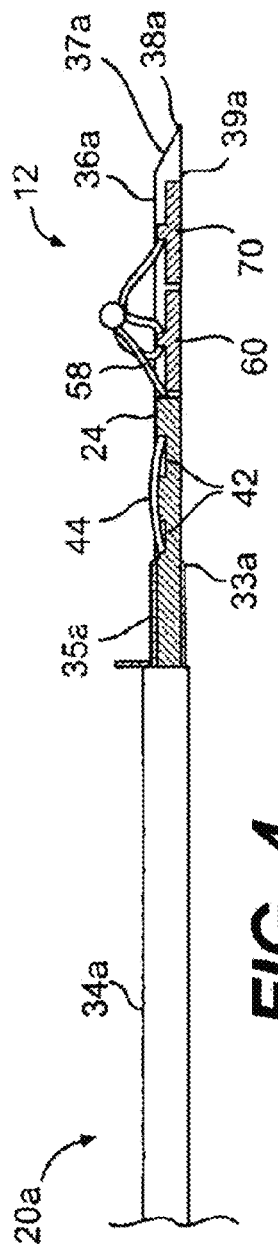
FIG. 2
FIG. 3
FIG. 4

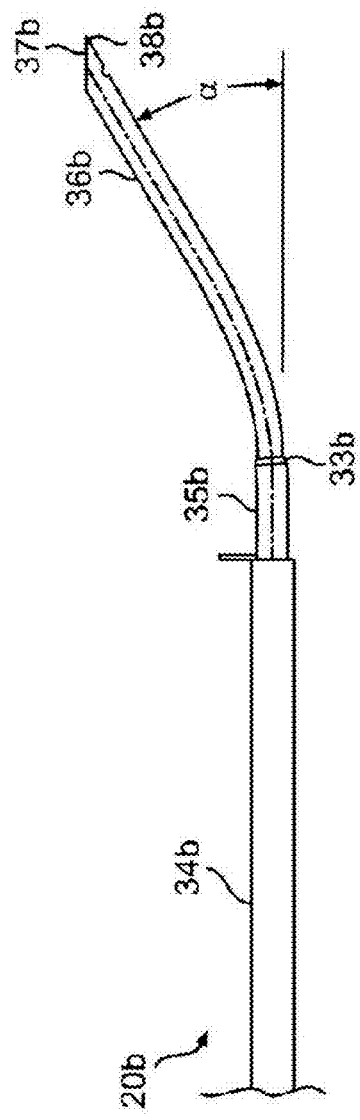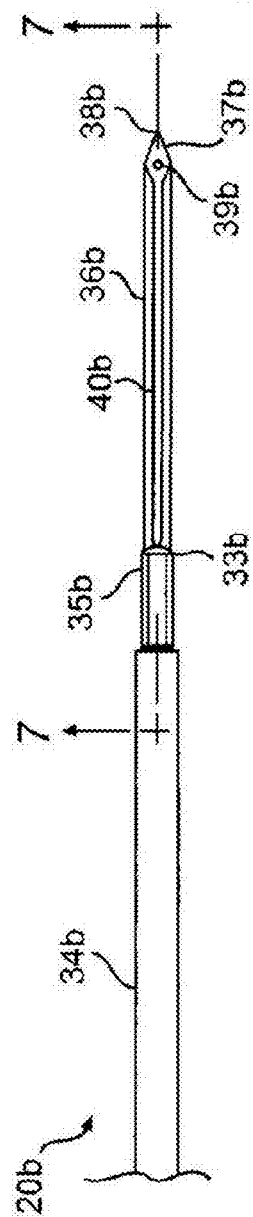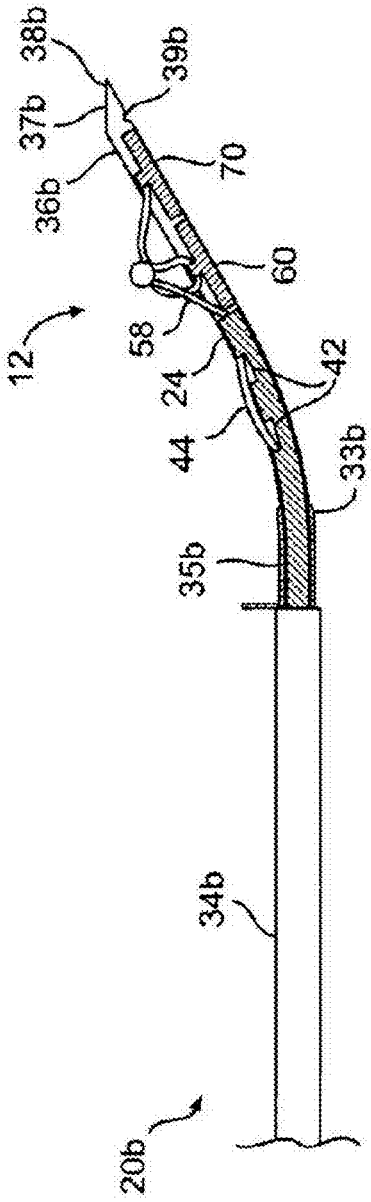

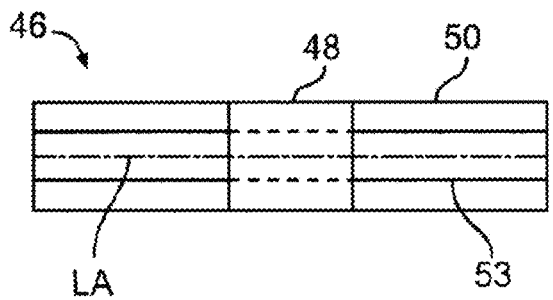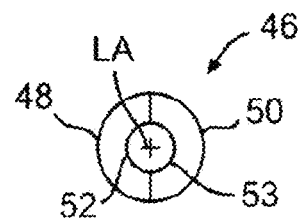
FIG. 9  FIG. 10
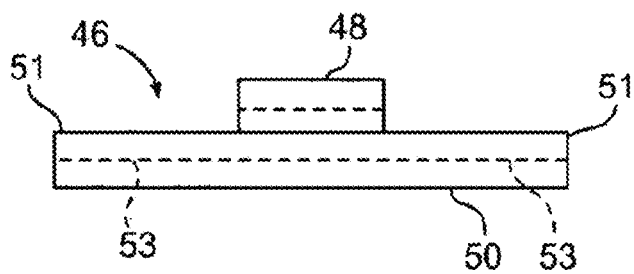
FIG. 11
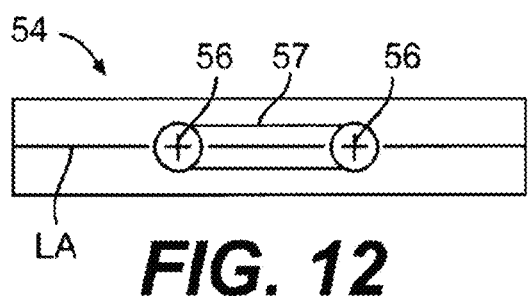
FIG. 12  FIG. 13
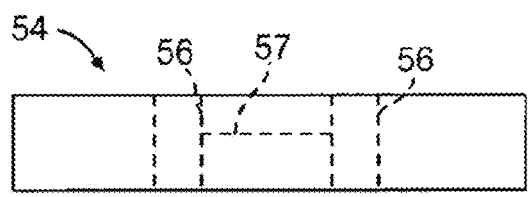
FIG. 14

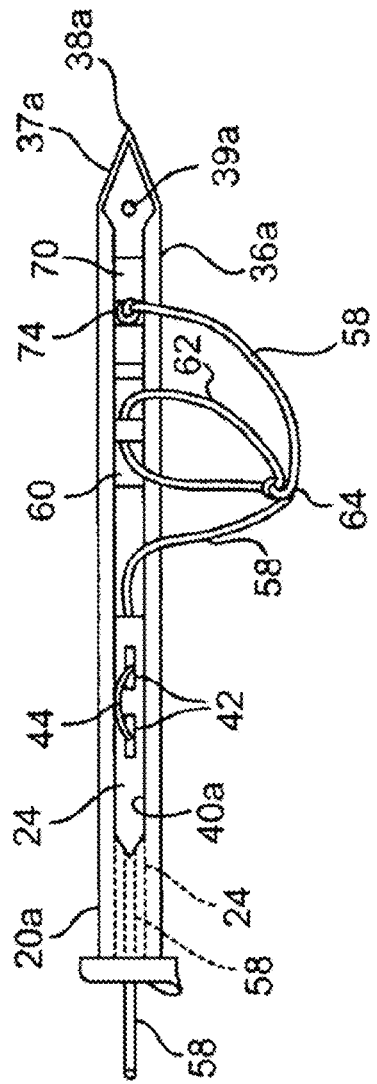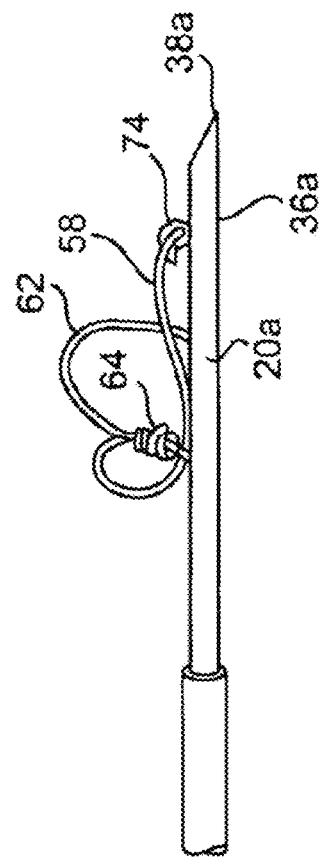

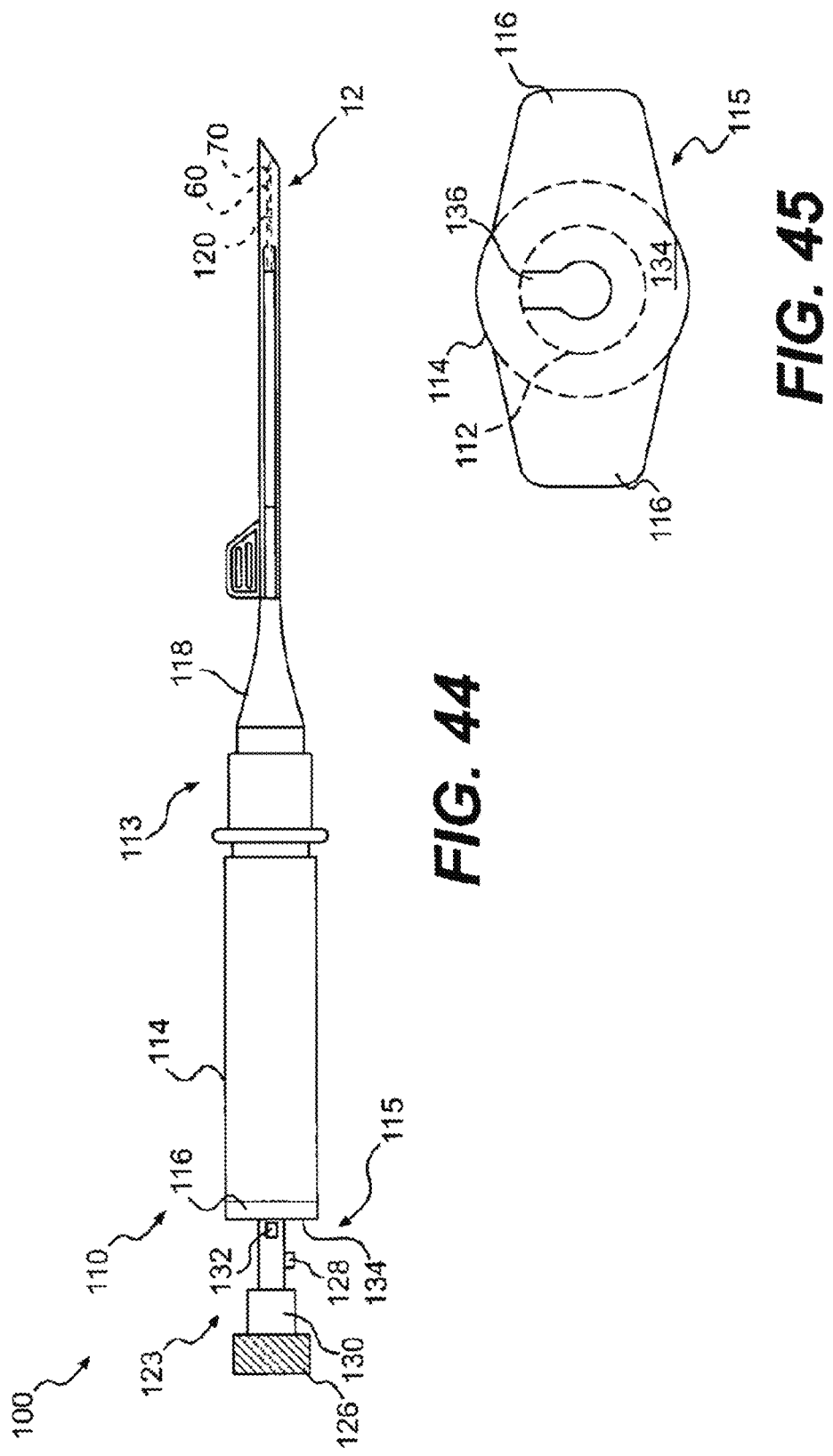

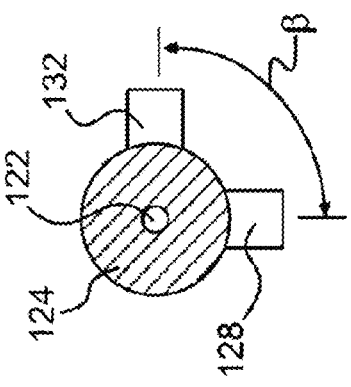
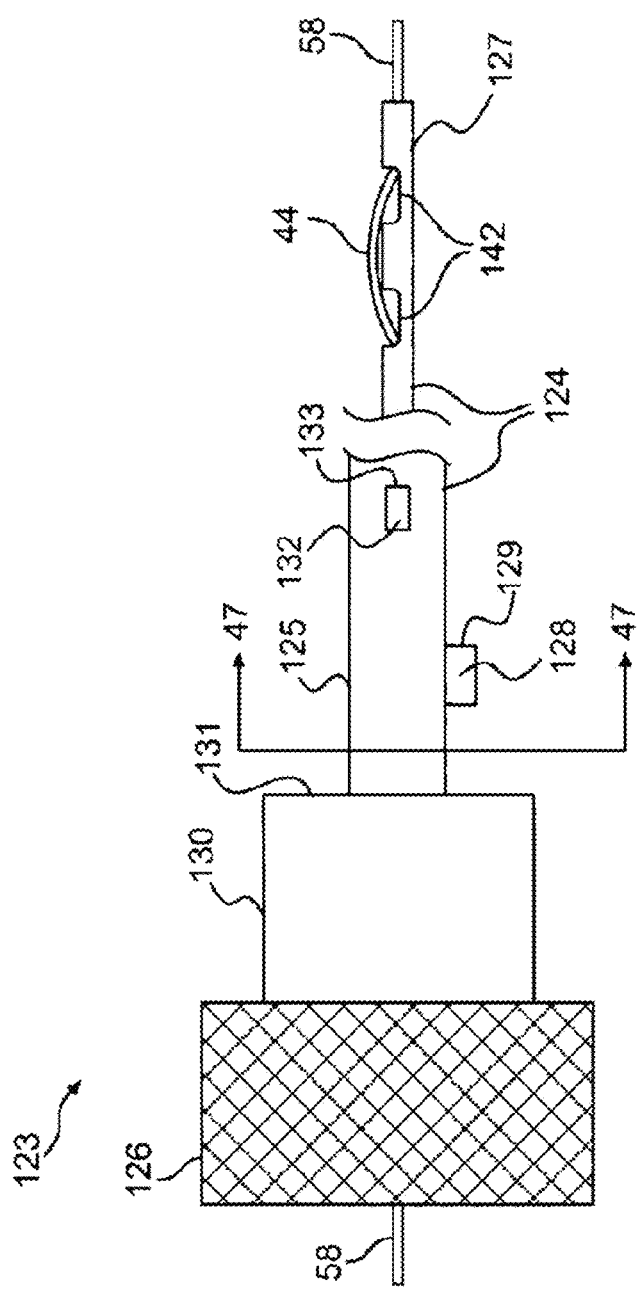

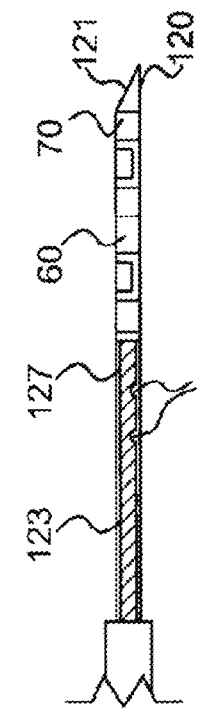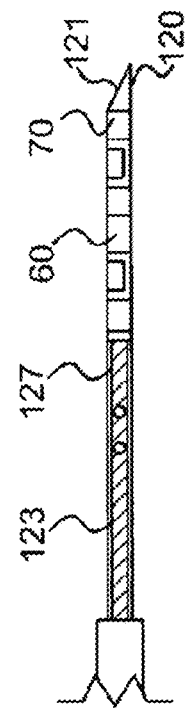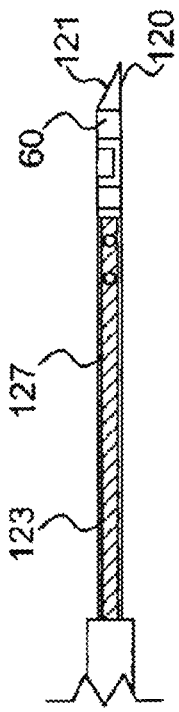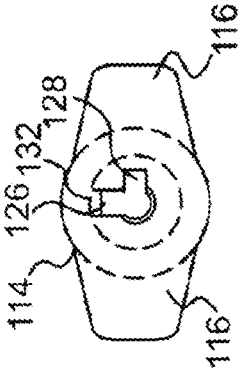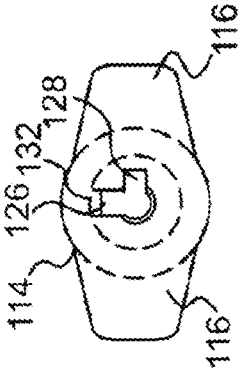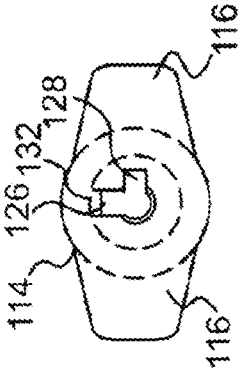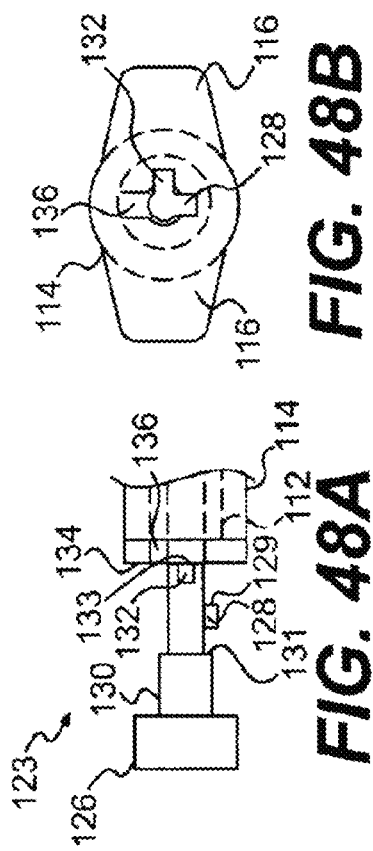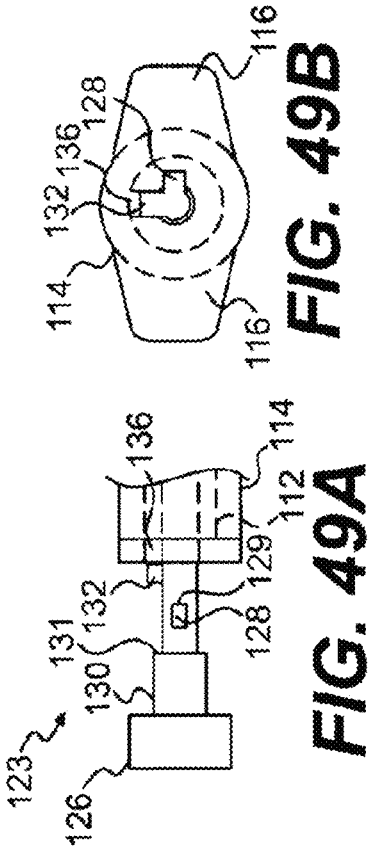

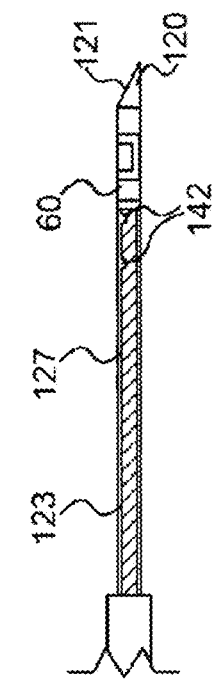 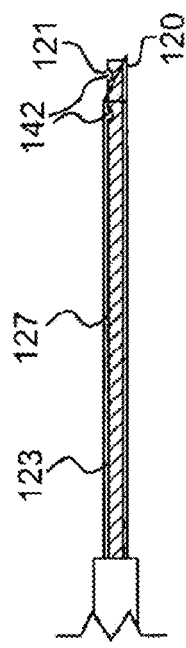 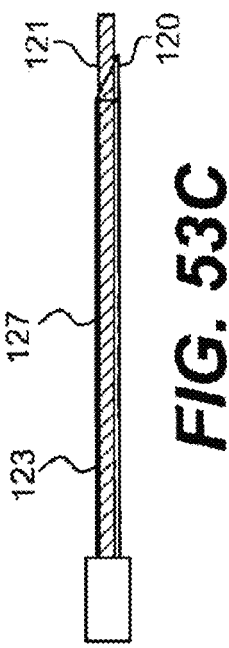
FIG. 51C  FIG. 52C  FIG. 53C
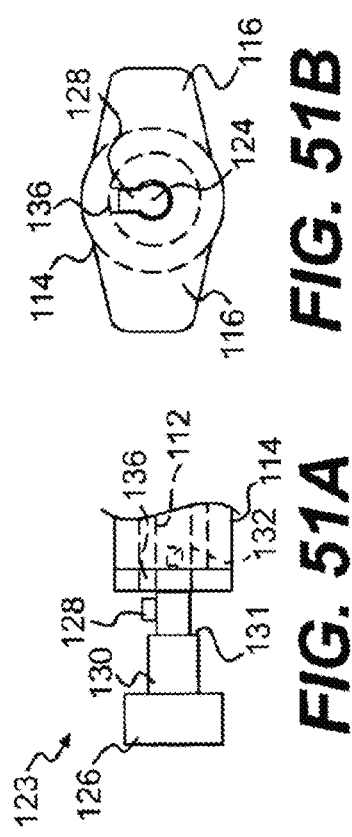 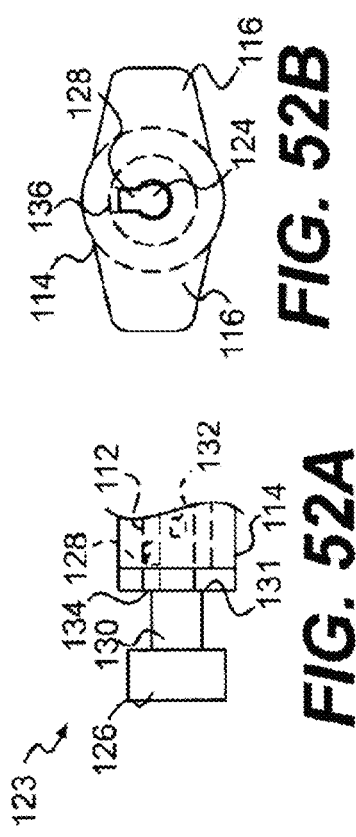 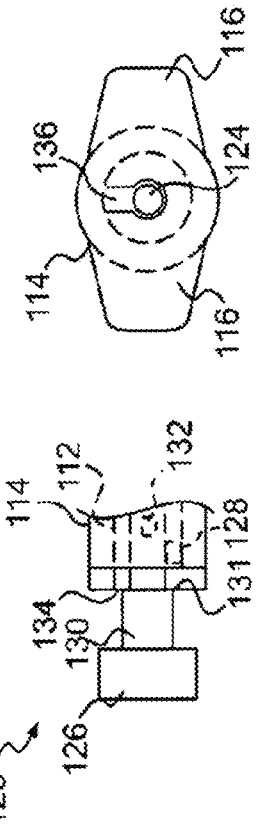
FIG. 51B  FIG. 52B  FIG. 53B
FIG. 51A  FIG. 52A  FIG. 53A

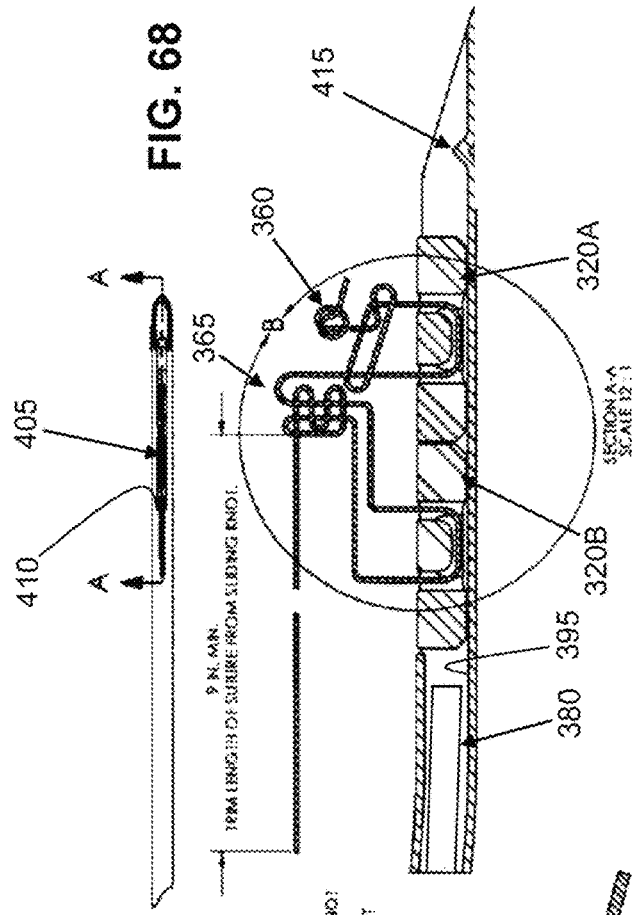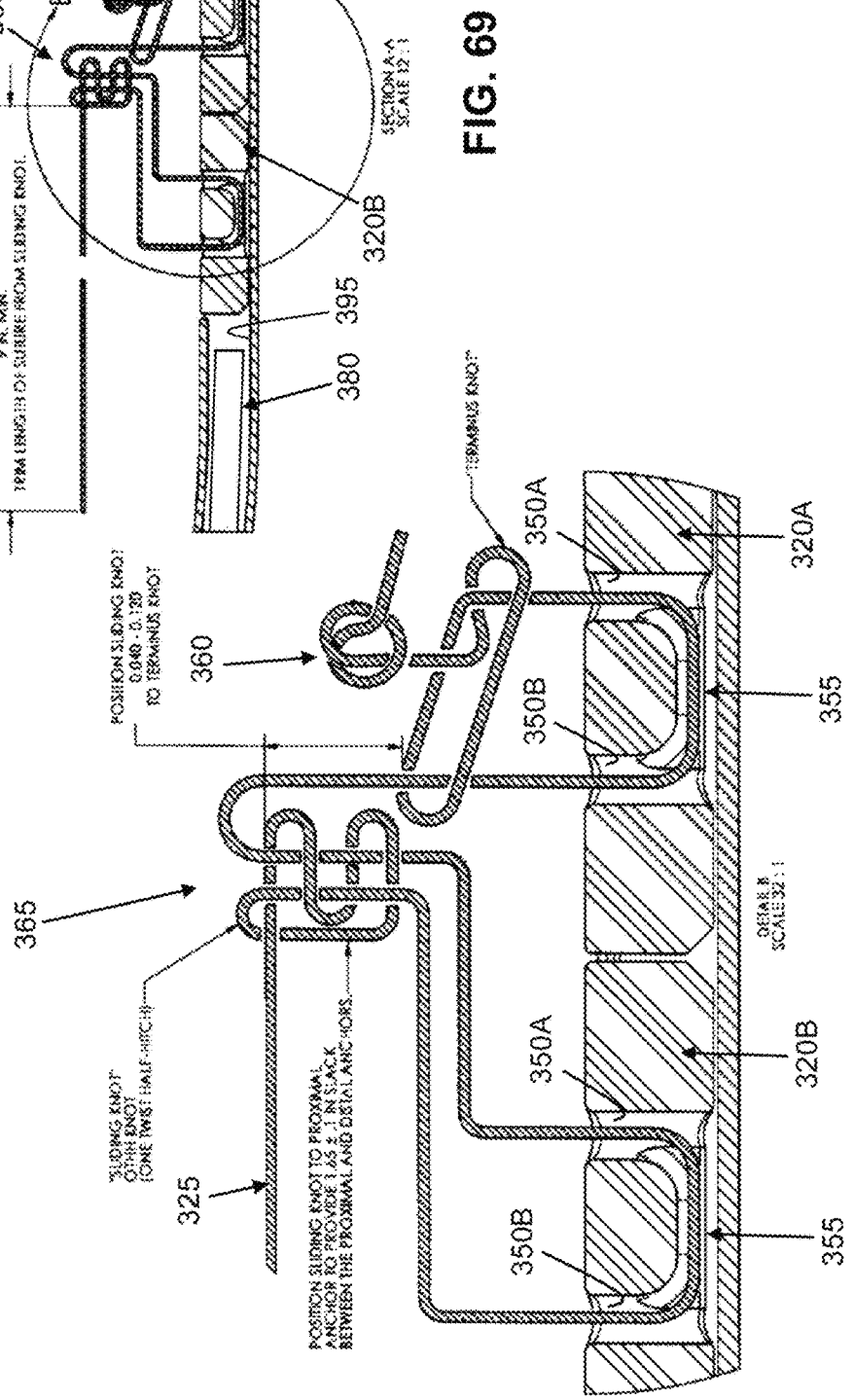

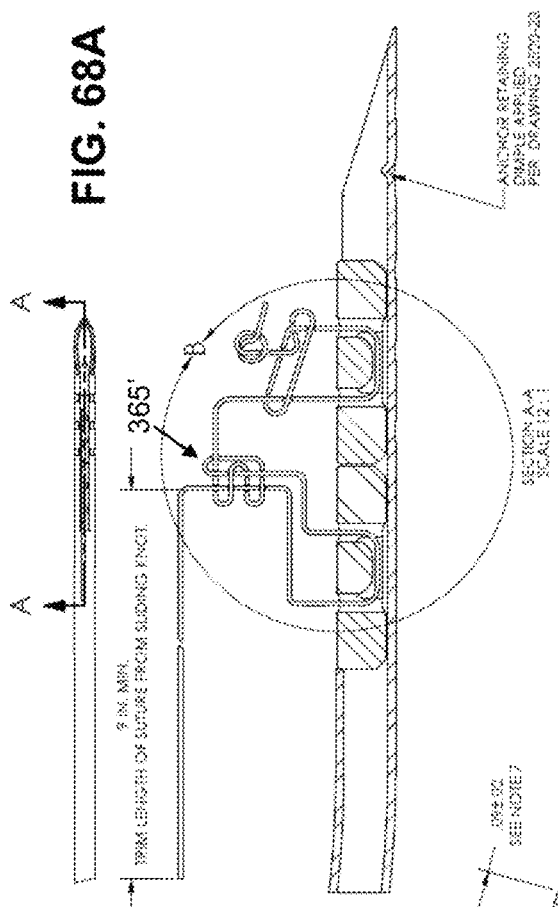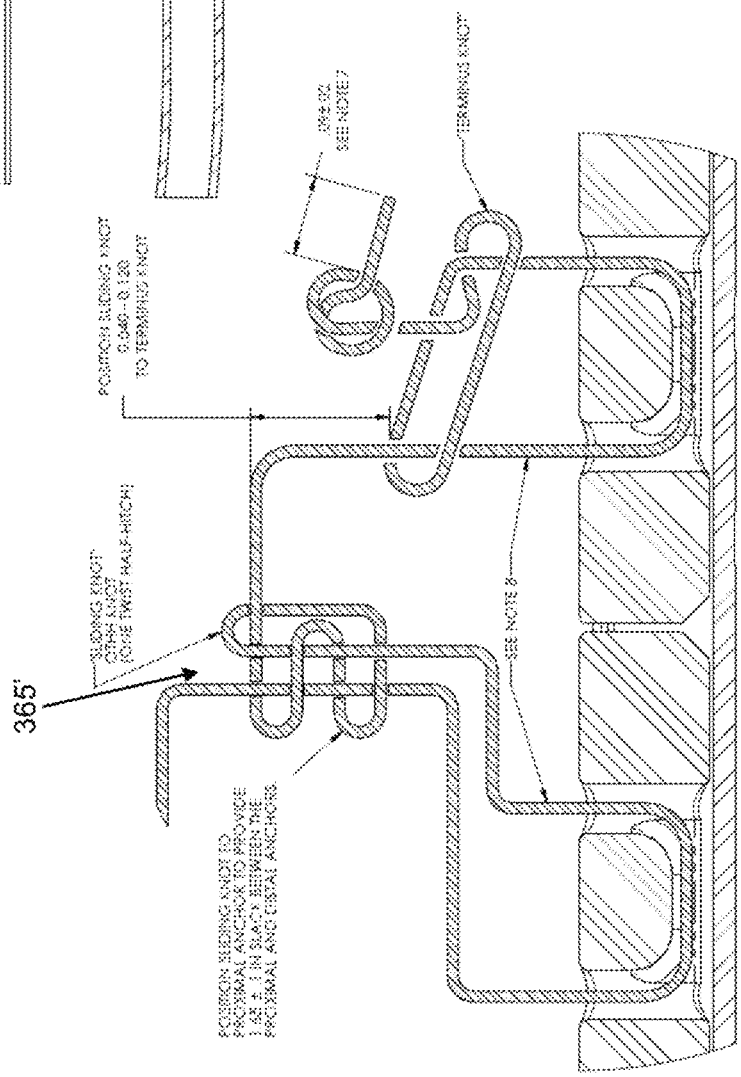

SYSTEMS AND METHODS FOR ALL-INSIDE SUTURE FIXATION FOR IMPLANT ATTACHMENT AND SOFT TISSUE REPAIR

CROSS-REFERENCE TO RELATED APPLICATIONS

The present application is a continuation of U.S. patent application Ser. No. 15/604,071, filed on May 24, 2017, which claims the benefit of the filing date of U.S. Provisional Patent Application No. 62/341,744 filed May 26, 2016, and U.S. Provisional Patent Application No. 62/370,167 filed Aug. 2, 2016, the disclosures of which are hereby incorporated herein.

FIELD OF THE INVENTION

The present invention relates generally to a system and method for reducing or bringing into close approximation, generally referred to as re-approximation herein, pieces of torn or damaged soft tissue to facilitate tissue repair and healing, and/or for attaching an implant during soft tissue repair, such as in meniscal repair or replacement. More particularly, the present invention relates to a system and method for an all-inside suture fixation device and method designed for the placement of surgical anchors.

BACKGROUND OF THE INVENTION

There are current instruments and systems on the market for use in repairing torn or damaged soft tissue, such as a torn meniscus. However, such devices have various drawbacks. For example, current systems on the market utilize needles and implants that have a comparatively large cross-section which damage the tissue during implantation. Further, such systems can be difficult to use in that an operator, such as a surgeon, must utilize higher forces than should be required to position the needle and implant the anchors. Such systems include the FAST-FIX™ and RAPIDLOC™.

Similarly, such devices are used in procedures for surgical attachment of a soft tissue implant in a joint, such as an autograft, allograft, or xenograft tissue or other compatible tissues and/or devices. Such implants may be bioresorbable and/or non-resorbable, synthetic and/or non-synthetic. One example of a bioresorbable implant is the CMI™ (Ivy Sports Medicine LLC (a division of Stryker Orthopedics), Redwood City, Calif.), a collagen-based meniscus implant, the surgical attachment of which can involve techniques that are difficult to master. The above-mentioned systems similarly have limitations in these procedures because, in their delivery of anchors to attach an implant to the meniscal rim, they may cause unnecessary destruction to the implant. The needle used to pass the anchor through an implant and through the meniscal rim punctures the implant in a manner that may lead to tearing of the implant matrix.

There is a need, therefore, for a dimensionally smaller device that employs a needle and anchors that are less destructive on surrounding tissue and/or an implant, if present. Further, there is a need for a system that is more user-friendly and adaptable for each surgeon's particularities and surgical setup.

BRIEF SUMMARY OF THE INVENTION

One embodiment of the present invention includes a system for repairing a meniscus, including a suture assembly including a first anchor, a second anchor, and a length of suture connecting the first anchor and the second anchor, the suture including a slide knot along its length between the first anchor and the second anchor, and an inserter, the inserter including a needle having a longitudinal extending bore and an open distal end, the bore being configured to receive the first anchor and the second anchor, a housing operatively connected to a proximal end of the needle, the housing having a lumen and a slot, the slot including a first portion, a second portion, a first shoulder and a second shoulder, and a pusher configured to rotate and slide within the lumen of the housing and the longitudinal extending bore of the needle, the pusher having an extension extending through the slot and configured to be maneuverable through the first portion and second portion and engageable with the first shoulder and second shoulder.

In another embodiment, the present invention includes an instrument for repairing a meniscus including a needle having a longitudinal extending bore and an open distal end, a housing operatively connected to a proximal end of the needle, the housing having a lumen, a slot including a first portion, a second portion, a first shoulder and a second shoulder, and a first grip and a second grip, and a pusher configured to rotate and slide within the lumen of the housing and the longitudinal extending bore of the needle, the pusher having an extension extending through the slot and configured to be maneuverable through the first portion and second portion and engageable with the first shoulder and second shoulder.

In a further embodiment, the present invention includes a system for repairing a meniscus, including a suture assembly including a first anchor, a second anchor, and a flexible suture connecting the first anchor and the second anchor, the flexible suture including a slide knot between the first anchor and the second anchor, and an inserter, including a needle having a longitudinal extending bore and an open distal end, the bore being configured to receive the first anchor and the second anchor, a housing operatively connected to a proximal end of the needle, the housing having a lumen, a pusher configured to rotate and slide within the lumen of the housing and the longitudinal extending bore of the needle, and a sheath releasably secured to the housing by a press-fit engagement and having a lumen, the needle being positionable within the lumen.

BRIEF DESCRIPTION OF THE DRAWINGS

Features of the invention are shown in the drawings, in which like reference numerals designate like elements. The drawings form part of this original disclosure, in which:

FIG. 2 is a top view of an embodiment of a needle of the system of FIG. 1;

FIG. 3 is a side view of the needle of FIG. 2;

FIG. 4 is a cross-sectional view taken along line 4-4 in FIG. 2;

FIG. 5 is a side view of another embodiment of the needle for the system of FIG. 1;

FIG. 6 is a top view of the needle of FIG. 5;

FIG. 7 is a cross-sectional view taken along line 7-7 in FIG. 6;

FIG. 9 is a top view of an anchor of a suture of the system of FIG. 1;

FIG. 10 is an end view of the anchor of FIG. 9;

FIG. 11 is a side view of the anchor of FIG. 9;

FIG. 12 is a top view of another embodiment of an anchor of the suture for the system of FIG. 1;

FIG. 13 is an end view of the anchor of FIG. 12;

FIG. 14 is a side view of the anchor of FIG. 12;

FIG. 30 is a top view of the needle with the suture loaded therein;

FIG. 31 is a side view of the needle of FIG. 30;

FIG. 44 is a side view of another embodiment of a system for all-inside suture fixation for implant attachment and soft tissue repair of the present invention;

FIG. 45 is a proximal end view of a body portion of the system of FIG. 44;

FIG. 46 is a side view of an embodiment of a pusher of the system of FIG. 44;

FIG. 47 is a cross-sectional view of the pusher taken along line 47-47 in FIG. 46;

FIG. 48A is a side view of a proximal end of the pusher of FIG. 46 in a first position relative to the body portion;

FIG. 48B is the proximal end view of the body portion with a portion of the pusher in the first position of FIG. 48A;

FIG. 48C is a side view of a needle of the system of FIG. 44 and a distal end of the pusher, with the pusher in the first position of FIG. 48A;

FIG. 49A is a side view of the proximal end of the pusher of FIG. 46 in a second position relative to the body portion;

FIG. 49B is the proximal end view of the body portion with a portion of the pusher in the second position of FIG. 49A;

FIG. 49C is a side view of the needle and the distal end of the pusher, with the pusher in the second position of FIG. 49A;

FIG. 50A is a side view of the proximal end of the pusher of FIG. 46 in a third position relative to the body portion;

FIG. 50B is the proximal end view of the body portion with a portion of the pusher in the third position of FIG. 50A;

FIG. 50C is a side view of the needle and the distal end of the pusher, with the pusher in the third position of FIG. 50A;

FIG. 51A is a side view of the proximal end of the pusher of FIG. 46 in a fourth position relative to the body portion;

FIG. 51B is the proximal end view of the body portion with a portion of the pusher in the fourth position of FIG. 51A;

FIG. 51C is a side view of the needle and the distal end of the pusher, with the pusher in the fourth position of FIG. 51A;

FIG. 52A is a side view of the proximal end of the pusher of FIG. 46 in a fifth position relative to the body portion;

FIG. 52B is the proximal end view of the body portion with a portion of the pusher in the fifth position of FIG. 52A;

FIG. 52C is a side view of the needle and the distal end of the pusher, with the pusher in the fifth position of FIG. 52A;

FIG. 53A is a side view of the proximal end of the pusher of FIG. 46 in a sixth position relative to the body portion;

FIG. 53B is the proximal end view of the body portion with a portion of the pusher in the sixth position of FIG. 53A;

FIG. 53C is a side view of the needle and the distal end of the pusher, with the pusher in the sixth position of FIG. 53A;

FIGS. 60-70A are schematic views showing further details of the anchor assembly of the system of FIGS. 54-59, wherein the terminus knot and the slip knot are shown in schematic form in FIG. 60 for clarity of illustration, and further wherein certain variations of the terminus knot and the slip knot are shown in line drawings in FIGS. 61, 68-70 and 68A-70A;

DETAILED DESCRIPTION

U.S. patent application Ser. No. 13/410,501, filed Mar. 2, 2012, U.S. patent application Ser. No. 11/501,235, filed Aug. 9, 2006, U.S. patent application Ser. No. 11/348,467, filed Feb. 7, 2006, and U.S. Provisional Patent Application Ser. No. 60/650,131, filed Feb. 7, 2005, are hereby incorporated herein by reference as if fully set forth herein.

Figure 1:
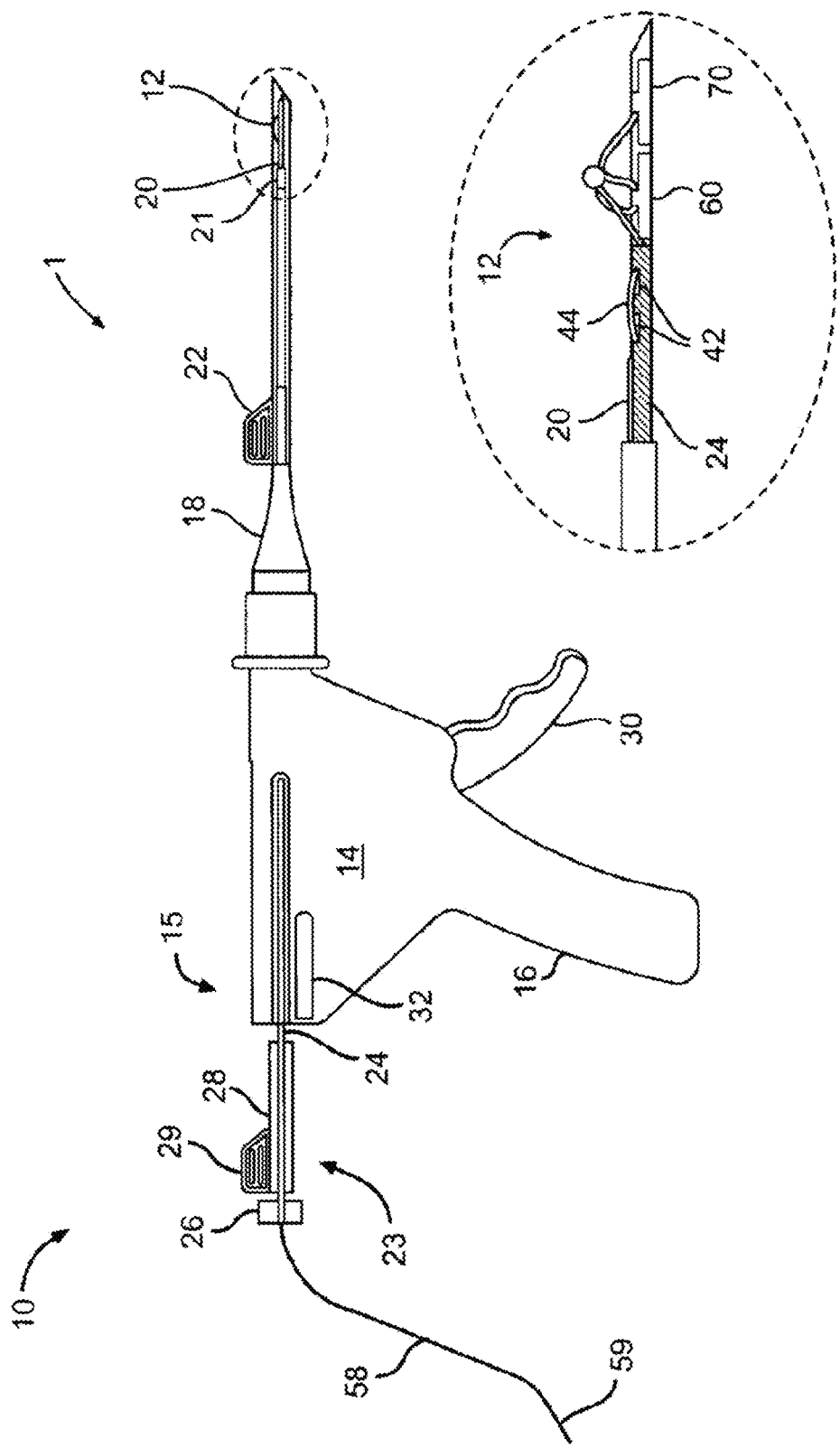
FIG. 1 is a side view of an embodiment of a system for all-inside suture fixation for implant attachment and soft tissue repair of the present invention.

A system 1 for repairing soft tissue, such as for example a meniscus, according to an embodiment of the present invention is illustrated in FIG. 1. The system 1 includes an applicator 10 that is constructed and arranged to deploy a suture 12 to soft tissue, such as the meniscus. The suture 12 generally includes a flexible length of suture material 58 and includes a pair of anchors 60, 70 positioned thereon. The suture 12 will be discussed in greater detail below.

The applicator 10 includes a body portion 14 that defines a handle 16 that is configured to be grasped by the user. The body portion 14 of the applicator 10 receives a cannula 18 that extends from the body portion 14 in a direction that is away from the handle 16. The body portion 14 and cannula 18 may be constructed and arranged like those described and shown in U.S. Pat. No. 5,928,252, which is incorporated herein by reference in its entirety. Because the inner workings of the body portion 14 are not related to the present invention, they are not described in detail herein.

The applicator 10 also includes a needle 20 that is connected to a distal end of the cannula 18. Of course, the needle 20 may be considered to be a part of the cannula 18 itself. The needle 20 will be described in greater detail below. The applicator 10 also includes a pusher 23 that includes a hollow rod 24 that extends through the body portion 14, the cannula 18, and is slidingly received by the needle 20. A knob 26 is attached to one end of the rod 24 and a spacer 28 with a tab 29 is disposed between the knob 26 and a proximal end 15 of the body portion 14 so that the movement of the knob 26 relative to the body portion 14 and, hence, movement of the rod 24 relative to the needle 20, may be limited to prevent premature deployment of one of the anchors 60 prior to the placement of the other anchor 70, as described in further detail below. A trigger 30 is connected to and extends from the body portion 14, as shown in FIG. 1. The trigger 30 is configured to manually control the advancement of the rod 24 within the cannula 18. A side lever 32 is connected to the body portion so as to be pivotable thereon. Operation of the side lever 32 will be discussed in greater detail below.

As shown in FIG. 1, a depth penetration limiter 21 is placed over the distal end of the cannula 18 so as to partially cover the needle 20. The limiter 21 provides the user with a visualization of the depth of the needle 20 in the tissue to avoid neurovascular injury. An outer sheath 22 is placed over the limiter 21 to aid in the insertion of the cannula 18 into the incision already created in the patient. The outer sheath 22 may be designed to partially surround the limiter 21 so that the user may still see at least a portion of the limiter 21 when the needle 20 is being inserted into the incision. The outer sheath 22 is removed by the user once the cannula 18 has been inserted into the incision site.

One embodiment of a needle 20a that may be used as the needle 20 in FIG. 1 is shown in FIGS. 2-4. As shown, the needle 20a includes a sleeve 34a that is attached to the cannula 18 at a proximal end. The needle 20a also includes a distal end 36a that is connected to the sleeve 34a and is constructed and arranged to be inserted into a meniscus or a tissue. The distal end 36a is substantially straight and includes a point 38a for piercing the meniscus or tissue and a slot 40a, which allows for the flexible length 58 of the suture 12 to extend out of the needle 20a. As shown in the Figures, the distal end 36a of the needle 20a also includes a cutting surface 37a that is constructed and arranged to cut excess suture 12, which will be described in greater detail below.

As shown in FIGS. 2-4, a cutting sheath 35a that at least partially surrounds the distal end 36a may also be provided. In the illustrated embodiment, the cutting sheath 35a completely surrounds the circumference of the distal end 36a. In other embodiments, the cutting sheath 35a may only partially surround the distal end 36a. The cutting sheath 35a is configured to be slidable relative to the distal end 36a so that it may be moved longitudinally along the distal end 36a toward the point 38a, and then moved back again toward the sleeve 34a. The cutting sheath 35a may include a tab that extends outward from the needle 20a so that the user may manipulate the cutting sheath 35a via the tab. As shown, the cutting sheath 35a includes at least one cutting surface 33a that is constructed and arranged to cut excess suture 12, which will be described in greater detail below.

As shown in FIG. 4, the distal end 36a is configured to hold the pair of anchors 60, 70 of the suture 12. The needle 20a may include a dimple 39a located near the point 38a to assist in seating the anchors 60, 70 prior to deployment of the anchors 60, 70 from the needle 20a, as will be described in greater detail below. The needle 20a may be manufactured from, for example stainless steel, and is sized to withstand insertion through the implant and the meniscus substantially without bending or budding.

Another embodiment of a needle 20b that may be used as the needle 20 in the applicator 10 is shown in FIGS. 5-7. As shown, the needle 20b includes a sleeve 34b that is attached to the cannula 18 at a proximal end. The needle 20b also includes a distal end 36b that is connected to the sleeve 34b and is constructed and arranged to be inserted into a meniscus or a tissue. The distal end 36b is curved such that it extends at an angle α relative to the sleeve 34b. The angle α may be about 15-45 degrees, and for example, about 30 degrees. The distal end 36b also includes a point 38b for piercing the meniscus or tissue and a slot 40b, which allows for portions of the suture 12 to extend out of the needle 20b. The distal end 36b of the needle 20b also includes at least one cutting surface 37b that is constructed and arranged to cut excess suture 12.

As shown in FIGS. 5-7, a cutting sheath 35b that at least partially surrounds the distal end 36b may also be provided. In the illustrated embodiment, the cutting sheath 35b completely surrounds the circumference of the distal end 36b. In other embodiments, the cutting sheath 35b may only partially surrounds the distal end 36b. The cutting sheath 35b is configured to be slidable relative to the distal end 36b so that it may be moved longitudinally along the distal end 36b toward the point 38b, and back again to the sleeve 34b. The cutting sheath 35b may include a tab that extends outward from the needle 20b so that the user may manipulate the cutting sheath 35b via the tab. As shown, the cutting sheath 35b includes a cutting surface 33b that is constructed and arranged to cut excess suture 12.

As shown in FIG. 7, the distal end 36b is also configured to hold the pair of anchors 60, 70. The needle 20b may also include a dimple 39b located near the point 38b to assist in seating the anchors 60, 70 prior to deployment. Like the needle 20a of FIGS. 2-4, the needle 20b may be manufactured from, for example, stainless steel, and is sized to withstand insertion through the implant and the meniscus substantially without bending or buckling.

Figure 8:
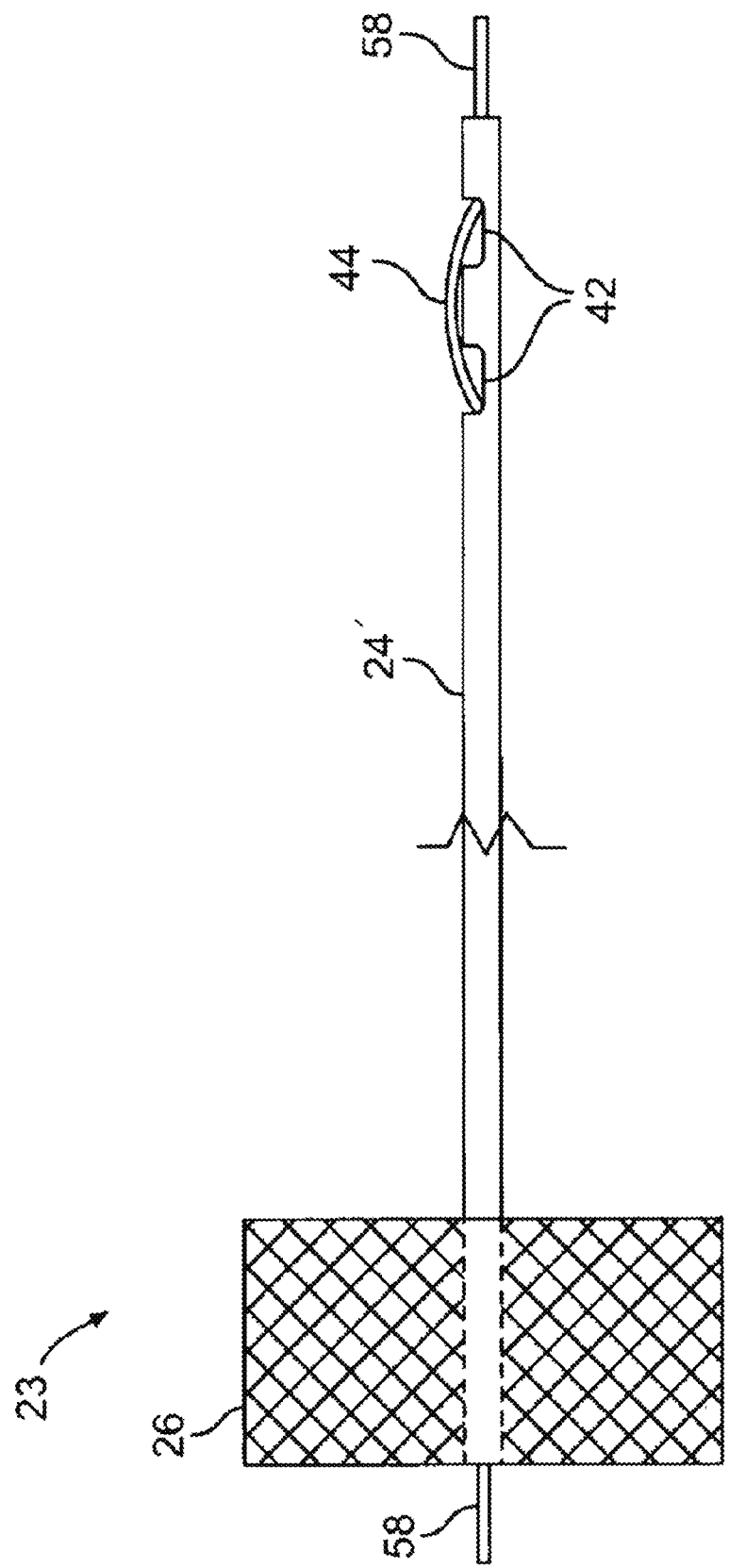
FIG. 8 is a side view of a pusher of the system of FIG. 1.

An embodiment of the pusher 23 is shown in greater detail in FIG. 8. The rod 24 is hollow and is configured to receive the flexible length 58 of the suture 12 that extends away from the needle 20. The knob 26 includes a hole for receiving the rod 24, so that the flexible length 58 of the suture 12 may extend through the knob 26 as well. A distal portion of the rod 24 includes a pair of slots 42 that are configured to allow the flexible length 58 of the suture 12 to be threaded out of the rod 24 via one slot 42 (the distal slot) and back into the rod 24 via the other slot 42 (the proximal slot), as represented by an exposed portion 44 of the flexible length 58 of the suture 12. This threading of the suture 12 properly aligns the exposed portion 44 relative to the rod 24 to facilitate the cutting of the suture 12, which will be described in further detail below. As shown in FIG. 7, the rod 24 may be flexible so that it may be used with the embodiment of the needle 20b described above.

FIGS. 9-11 illustrated an embodiment of an anchor 46 that may be used as the anchors 60, 70 of the suture 12. As shown, the anchor 46 includes a tab 48 that extends upward from a body 50. The body 50 has opposing ends 51 that are substantially perpendicular to a longitudinal axis LA of the anchor 46. A hole 52 that is centered on the longitudinal axis LA extends through the body 50 and the tab 48 where the body 50 and tab 48 are connected. Otherwise, the body 50 includes a hollowed out half-cylinder 53 at portions where the tab 48 is not connected. The anchor 46 may be made out of any material desired such as, polymer, for example polyether ether ketone (PEEK), or a bioabsorbable polymer, for example poly(L-lactide).

Another embodiment of an anchor 54 for use in the suture 12 of the system 1 is shown in FIGS. 12-14. As shown, the anchor 54 is a solid rod with a pair of holes 56 that extend substantially perpendicularly through the longitudinal axis of the rod. The holes 56 are sized to receive a flexible portion of the suture 12. A recessed channel 57 is located between the holes 56 to seat the flexible length 58 of the suture 12. Like the anchor 46, the anchor 54 may be made out of any material desired such as, polymer, for example polyether ether ketone (PEEK), or a bioabsorbable polymer, for example poly(L-lactide).

In another embodiment of an anchor that may be used as one or both of the anchors 60, 70 of the suture 12, the anchor may include at least one barb that is formed from or connected to a main body portion of the anchor. The barb may be constructed and arranged to be biased to an orientation in which a free end of the barb extends away from the body, yet is oriented such that the free end is near the body when suitable pressure is applied to the barb. The use of such an anchor with the system 1 will be described in greater detail below.

Unless otherwise indicated herein, further discussions of the anchors 60, 70 will be for the anchor 46 illustrated in FIGS. 9-11, although it is understood that the anchor 54 of FIGS. 12-14 may be used with slight modifications to the language used to describe the assembly of the suture 12. Such modifications would be readily appreciated by one of skill in the art and are therefore not described herein.

Figure 15:
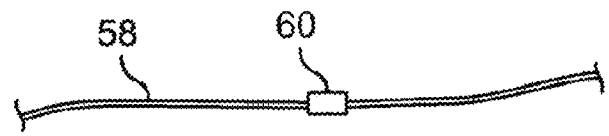
FIG. 15 is a view of an anchor threaded onto a suture of the system of FIG. 1.
Figure 16:
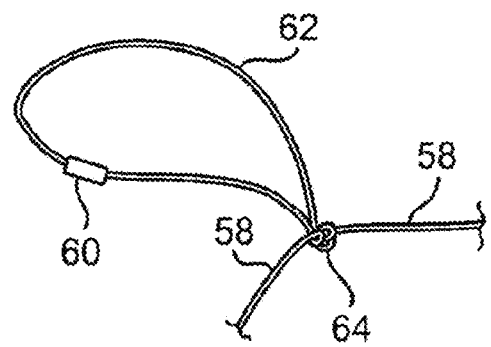
FIG. 16 is a view of the anchor and suture of FIG. 15 with a loop and a self-locking slide knot formed in the suture.

FIGS. 15-23 show the various stages of an embodiment of assembling the suture 12 of the system 1 of FIG. 1. FIG. 15 shows the flexible length 58 of the suture 12 with one anchor 60 threaded thereon. FIG. 16 shows a loop 62 and a knot 64 that closes the loop 62, with the anchor 60 being located within the loop 62. The knot 64 may be a self-locking slide knot. Methods for tying a self-locking slide knot are described in, for example, "A New Clinch Knot," Weston, P. V., Obstetrics & Gynecology, Vol. 78, pp. 144-47 (1991); "Physical Properties of Self Locking and Conventional Surgical Knots," Israelsson, L. A., et al., European Journal of Surgery, Vol. 160, No. 6-7, pp. 323-27 (1994); "Nicky's Knot—A New Slip Knot for Arthroscopic Surgery," De Beer, J. F., et al., Arthroscopy: The Journal of Arthroscopic and Relate Surgery, Vol. 14, No 1, pp. 109-110 (1998); "The Giant Knot: A New One-Way Self-Locking Secured Arthroscopic Slip Knot," Fleega, B. A., et al., Arthroscopy: The Journal of Arthroscopic and Relate Surgery, Vol. 15, No 4, pp. 451-52 (1999); "Arthroscopic Knot Tying Techniques," Nottage, W. M., et al., Arthroscopy: The Journal of Arthroscopic and Relate Surgery, Vol. 15, No 5, pp. 515-521 (1999); "The SMC Knot—A New Slip Knot With Locking Mechanism," Kim, S., et al., Arthroscopy: The Journal of Arthroscopic and Relate Surgery, Vol. 16, No 5, pp. 563-65 (2000); "Technical Note: A 'New' Arthroscopic Sliding Knot," Field, M. H., et al., Orthopedic Clinics of North America, Vol. 32, No. 3, pp. 525-26 (2001); "Arthroscopic Knot Tying," Kim, S., et al., Techniques in Shoulder & Elbow Surgery, Vol. 4, No. 2, pp. 35-43 (2003); "The PC Knot: A Secure and Satisfying Arthroscopic Slip Knot," Pallia, C. S., Arthroscopy: The Journal of Arthroscopic and Relate Surgery, Vol. 19, No 5, pp. 558-560 (2003); and "The Tuckahoe Knot: A Secure Locking Slip Knot," Wiley, W. B., et al., Arthroscopy: The Journal of Arthroscopic and Relate Surgery, Vol. 20, No 5, pp. 556-59 (2004), all of which are incorporated herein by reference in their entireties.

Figure 17:
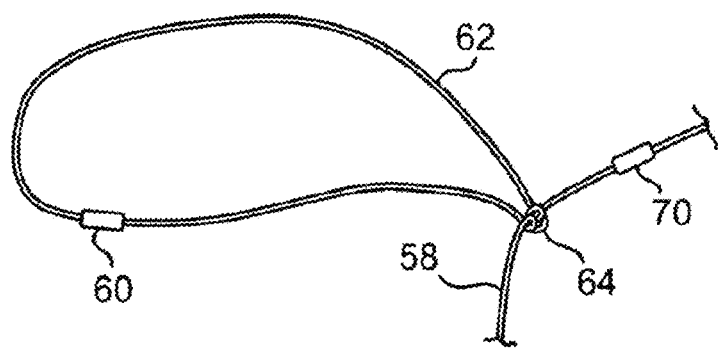
FIG. 17 is a view of the anchor and suture of FIG. 16 with a second anchor positioned on the suture.
Figure 18:
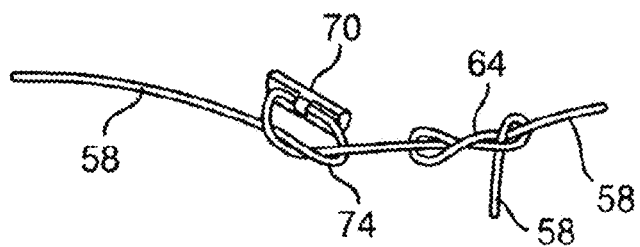
FIG. 18 is a partial view of the second anchor and suture of FIG. 17.

Once the self-locking slide knot 64 has been tied, another anchor 70 is slid onto the flexible length 58 until it is located approximately 7 mm from the knot 64, as shown in FIG. 17 (note that the Figures are not necessarily drawn to scale). This distance is only meant to be an example and is not intended to be limiting in any way. The flexible length 58 of the suture 12 is tied off with one hitch knot 74 on the anchor 70, as shown in FIG. 18.

Figure 19:
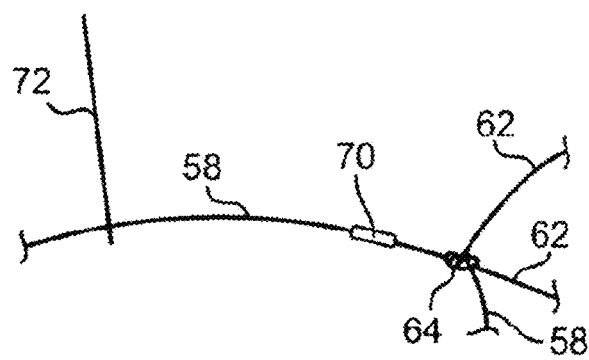
FIG. 19 is a partial view of the second anchor and suture of FIG. 17 with a needle threaded on the suture.
Figure 20:
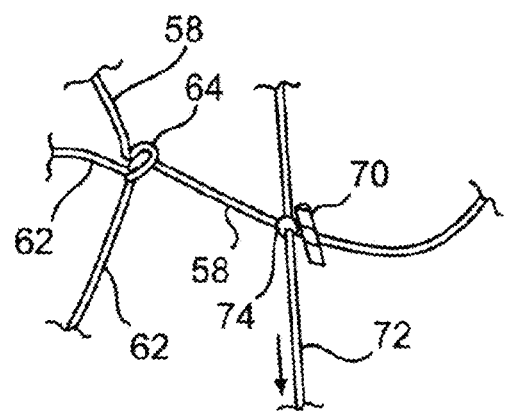
FIG. 20 is a partial view of the needle threaded on the suture and passing through the center of the suture at the second anchor.
Figure 21:
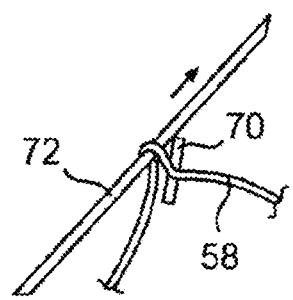
FIG. 21 is a partial view of the needle passing through the center of the suture at the second anchor a second time.
Figure 22:
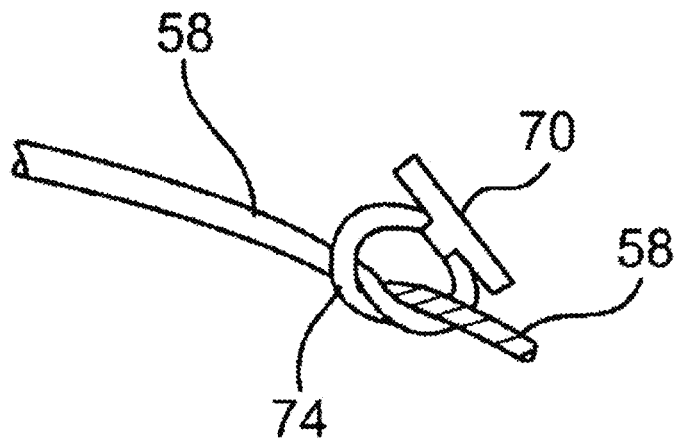
FIG. 22 is a view of the anchor with a knot securing it to the suture.
Figure 23:
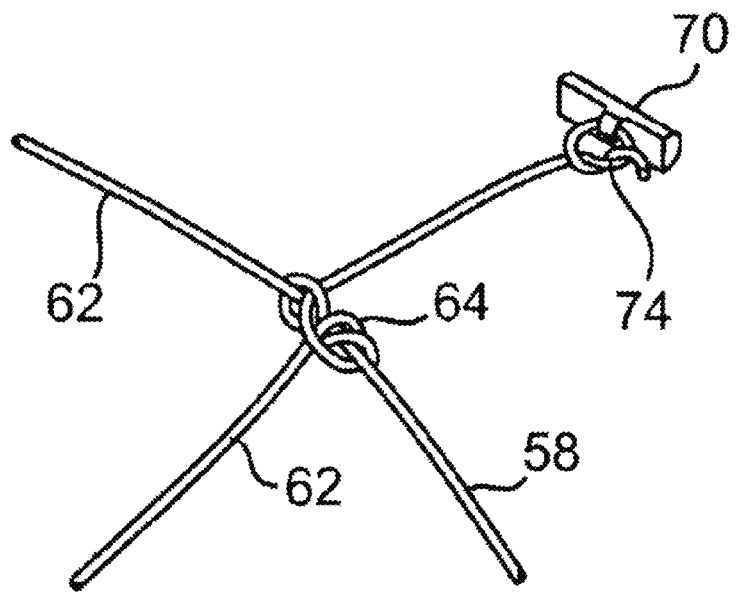
FIG. 23 is a partial view of the suture and the second anchor at one end thereof.
Figure 26:
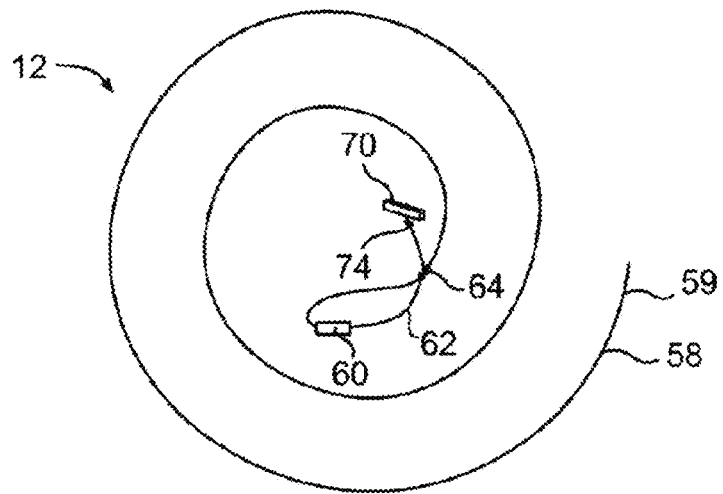
FIG. 26 is a view of the suture and anchor configuration of the system of FIG. 1.

Next, as shown in FIG. 19, a needle 72 is threaded with the remainder of the flexible length 58. The end of the flexible length 58 with the needle 72 is passed through the center of the suture of the hitch knot twice to hold the hitch knot 74 in place, as shown in FIGS. 20 and 21. As shown in FIG. 22, the excess flexible length 58 is cut, leaving approximately 2 mm as a tail. Finally, as shown in FIG. 23, the tip of the flexible length 58 may be melted to prevent fraying of the suture 12. An assembled suture 12 before it is loaded into the applicator 10 is shown in FIG. 26.

Figure 24:
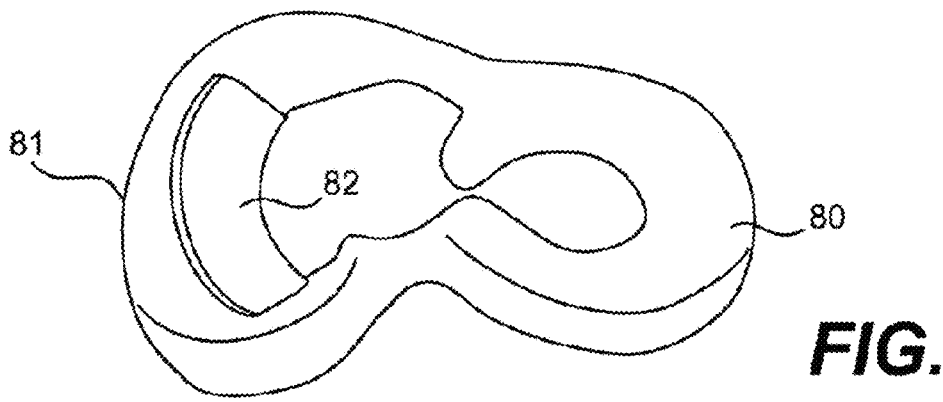
FIG. 24 is a perspective view of a meniscus with an implant positioned on the meniscus.

FIG. 24 shows a damaged meniscus 80 having a rim 81, and an implant 82 positioned adjacent the damaged part of the meniscus 80. The implant 82 may be any type of implant 82 suitable for such meniscus repair. For example, the implant 82 includes collagen. In an embodiment, the implant 82 includes the CMI, a collagen-based meniscus implant.

Figure 25:
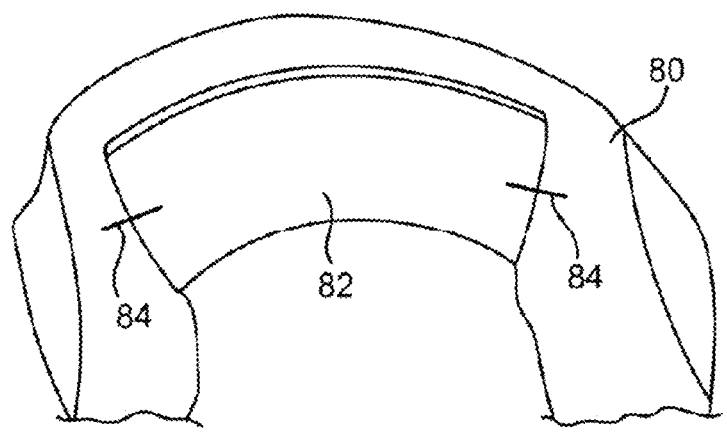
FIG. 25 is a view of the implant after it has been secured to the remaining surrounding soft tissue, such as meniscus.

The implant 82 illustrated in the Figures has already been cut to the appropriate size. Both ends of the implant 82 may be temporarily stapled or sutured using conventional means to hold the implant 82 in place while it is being secured to the meniscus 80. FIG. 25 shows a pair of staples 84, or sutures, holding the implant 82 in place.

Figure 27:
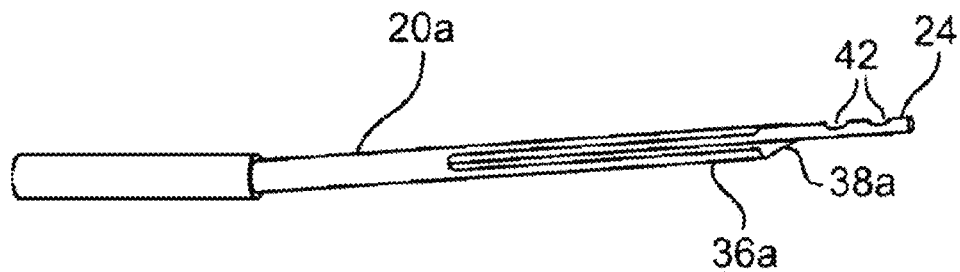
FIG. 27 is a top view of the needle with the pusher extended therefrom.

To load the suture 12 into the applicator 10, the cannula 18, with the needle 20a attached, is inserted into the body portion 14 of the applicator 10. In this embodiment, the needle 20a of FIGS. 2-4 is shown. However, it is understood that the needle 20b may also be used in the same way. The illustrated and described embodiments are not intended to be limiting in any way. While holding down the side lever 32 with a finger or a thumb, the rod 24 of the pusher 23 is inserted by the user into the proximal end 15 of the body portion 14 until the end of the rod 24 extends past the point 38a of the needle 20a with the slots 42 facing upward, as shown in FIG. 27.

Figure 28:
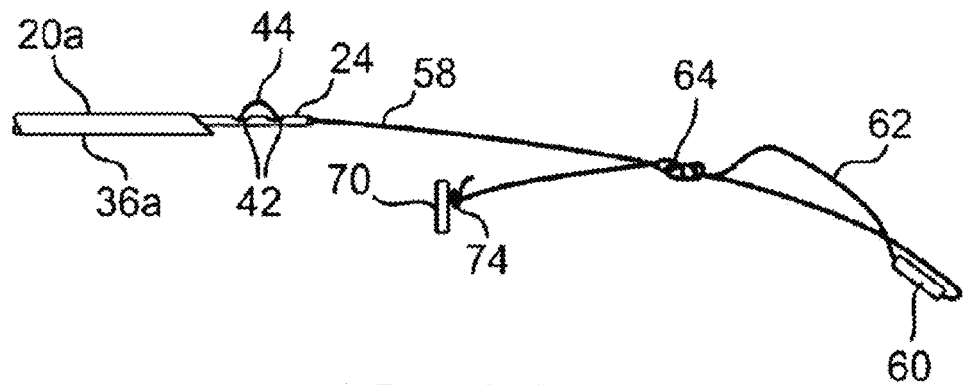
FIG. 28 is a side view of the suture being threaded into the pusher and the needle.
Figure 29:
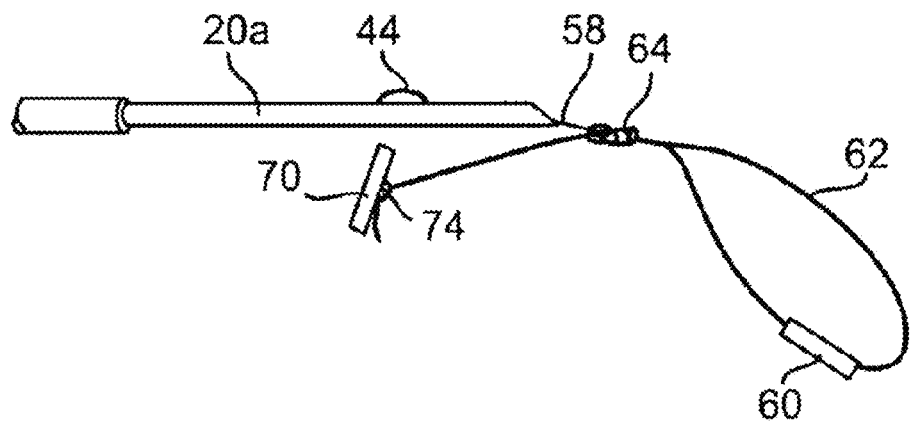
FIG. 29 is a side view of the suture further being threaded into the pusher and the needle.

Next, as shown in FIG. 28, an end 59 of the suture 12 that is opposite the anchor 70 is threaded though the rod 24 of the pusher 23 at the distal end 36a of the needle 20a. The end 59 of the suture 12 is laced through the distal end of the rod 24, pulled out of the rod 24 at the distal slot 42, threaded back into the rod 24 at the proximal slot 42, thereby leaving the exposed portion 44 outside of the rod 24. The end 59 of the suture 12 may extend several inches outside the pusher 23 beyond the proximal end 15 of the body portion 14 of the applicator 10 so that the user may grasp the suture 12 during the implant attachment procedure, which will be described below. Once the suture 12 has been loaded into the applicator 10, the user then presses the side lever 32 and retracts the pusher 23 back into the needle 20a, as shown in FIG. 29, to locate the slots 42 and the exposed portion 44 of the suture 12 before the proximal end of the needle slot 40a, as shown in FIG. 30. The anchor 60 is inserted into the distal end 36a of the needle 20a, and is followed by the anchor 70, as shown in FIGS. 30 and 31. The end 59 of the flexible length 58 that extends out of the pusher 23 at the proximal end 15 of the body portion 14 of the applicator 10 may be pulled so that the knot 64 is generally located on a side of the anchor 60 that is opposite the other anchor 70, as shown in FIG. 31 After the anchors 60, 70 are loaded into the cannula 18, a portion of the flexible length 58 may extend outside of the cannula 18 via the slot 40a of the needle 20a, as shown in FIGS. 30 and 31. In this arrangement, the pulling of the trigger 30 causes the anchor 70, the anchor 60, and the knot 64 to be deployed in that order.

Once the system 1 is assembled, the user places the spacer 28 between the knob 26 and the proximal end 15 of the body portion 14 so that the advancement of the anchor 60 will be limited until the placement of the anchor 70 is complete. The user then inserts the depth penetration limiter 21 and the outer sheath 22 over the distal end of the cannula 18 so as to cover the needle 20 during insertion of the needle 20 into the incision site. Once the needle 20 has been inserted into the incision site, the outer sheath 22 may be removed from the cannula 18. Of course, the use of the spacer 28, the outer sheath 22, and the depth penetration limiter 21 should be considered optional. The illustrated embodiment is not intended to be limiting in any way.

The user may then advance the anchors 60, 70 until the anchor 70 is located near the point 38a of the needle 20a, without extending out of the needle 20a. The dimple 39a may be used to assist with the placement of the anchor 70. In embodiments where the dimple 39a is used, the user should feel a slight resistance to the advancement of the anchor 70, which signals the user to stop advancing the pusher 23. Of course, the use of the dimple 39a should be considered to be optional. The illustrated embodiment is not intended to be limiting in any way.

Figure 32:
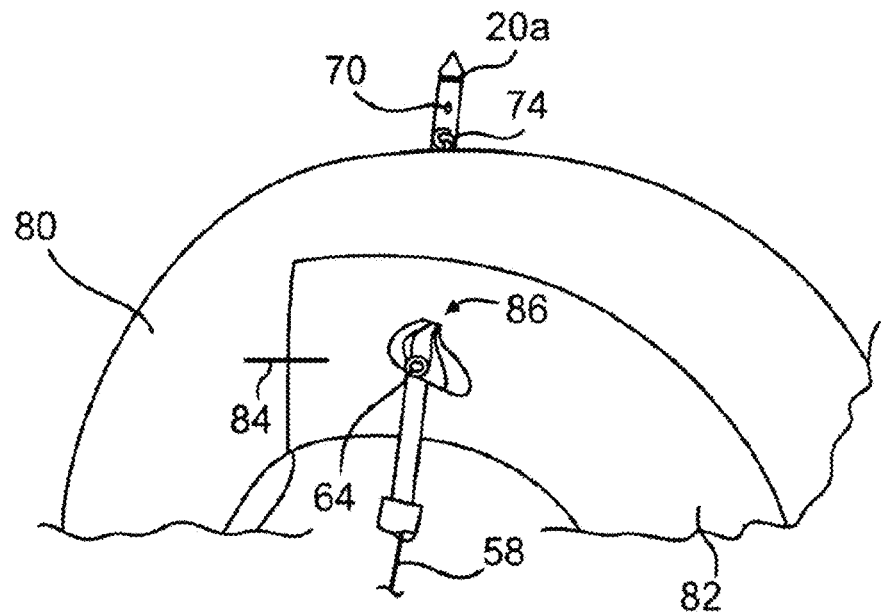
FIG. 32 is a top view of the needle of the system of FIG. 1 piercing the implant and meniscus of FIG. 25 at a first location.
Figure 33:
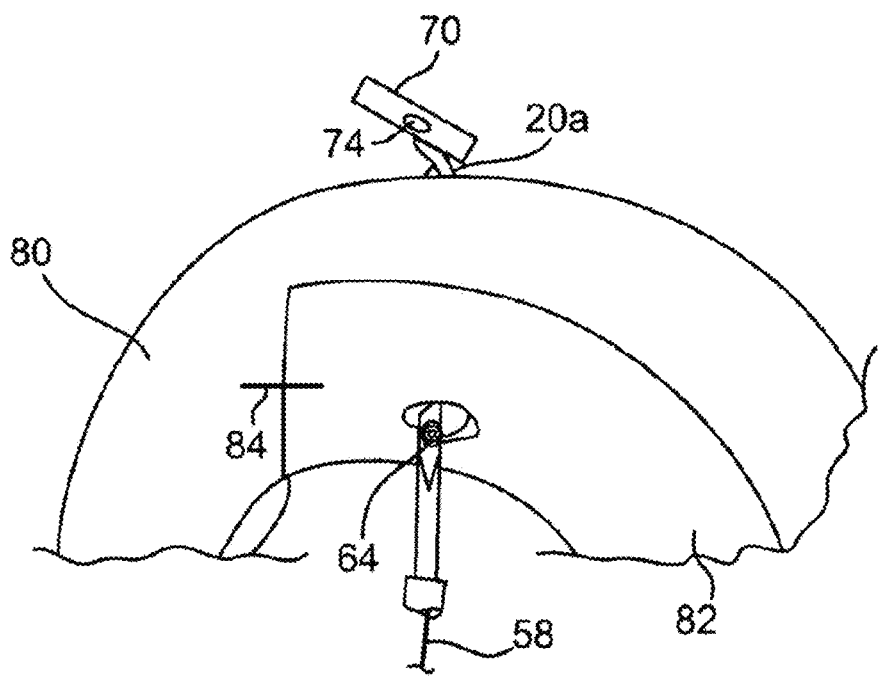
FIG. 33 is a top view of the needle of FIG. 32 after the first anchor has been deployed from the needle with the pusher.

While griping the handle 16 and the trigger 30 on the applicator 10, the user inserts the needle 20a into a patient at an incision site so that the needle 20a may then be inserted through the implant 82 and through the meniscus 80 at a first location 86, for example near the center of the implant 82, to a side opposite the insertion site, as shown in FIG. 32. The user should be sure that the hitch knot 74 on the anchor 70 has passed through the meniscus 80, as shown in FIG. 32. In an embodiment, the user then advances the pusher 23 via the trigger 30 until the anchor 70 is pushed outside the needle 20a, as shown in FIG. 33. The user should be careful to not advance the pusher 23 further to avoid the premature deployment of the anchor 60. The use of the spacer 28 assists in preventing the premature deployment of the anchor 60. In addition to, or in lieu of the spacer 23, the dimple 39a that is located near the point 38a of the needle 20a may also be used to provide the user with tactile feedback that the anchor 60 has been advanced to its proper pre-deployment position.

Figure 34:
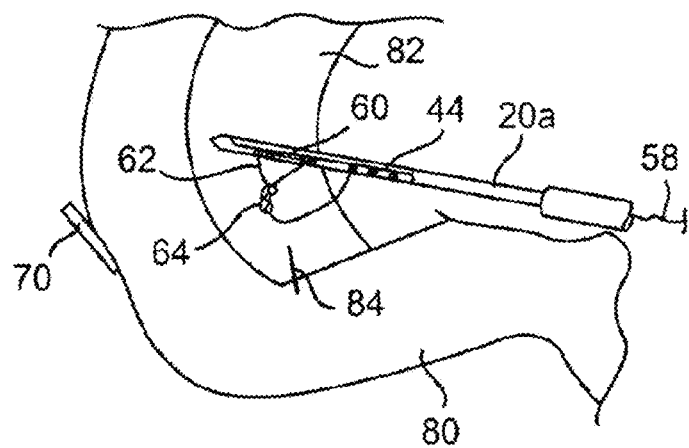
FIG. 34 is a perspective view of the needle of FIG. 32 after it has been pulled back through the meniscus and implant.

As shown in FIG. 34, the user then retracts the needle 20a slowly from the meniscus 80 and the implant 82, leaving the anchor 70 behind on the opposite side of the meniscus 80. The anchor 60 will remain inside the needle 20a. If the user hasn't already done so, the user next advances the anchor 60 until the anchor 60 is located near the point 38a of the needle 20a. Again for embodiments that include the dimple 39a, the dimple 39a may be used to guide the user to correctly position the anchor 60.

Figure 35:
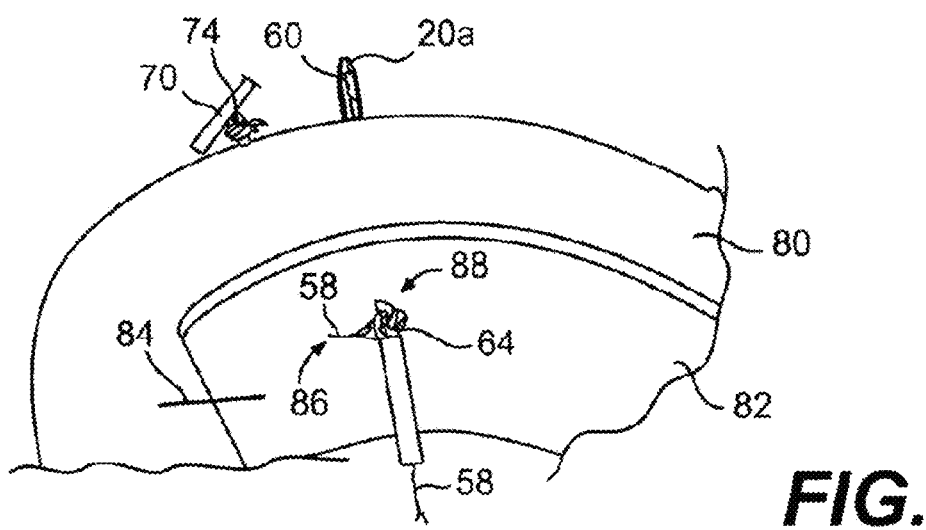
FIG. 35 is a top view of the needle of FIG. 32 piercing the implant and remaining surrounding soft tissue, such as meniscus, of FIG. 25 at a second location.
Figure 36:
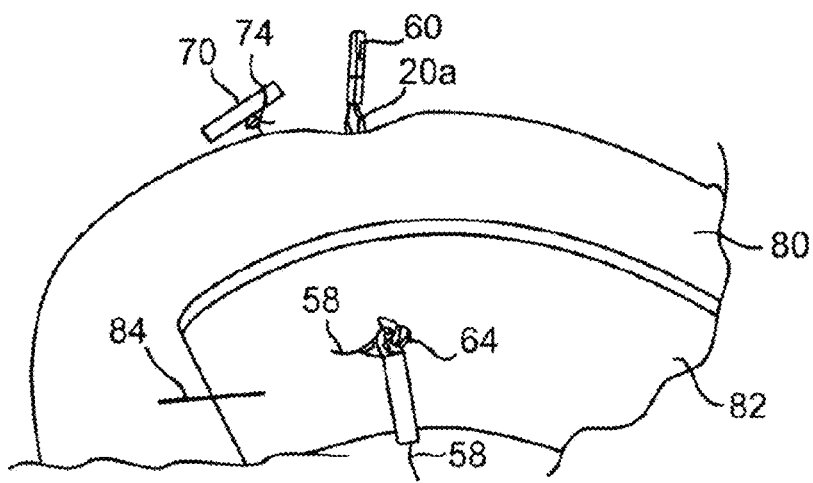
FIG. 36 is a top view of the needle of FIG. 35 after the second anchor has been deployed from the needle with the pusher.
Figure 37:
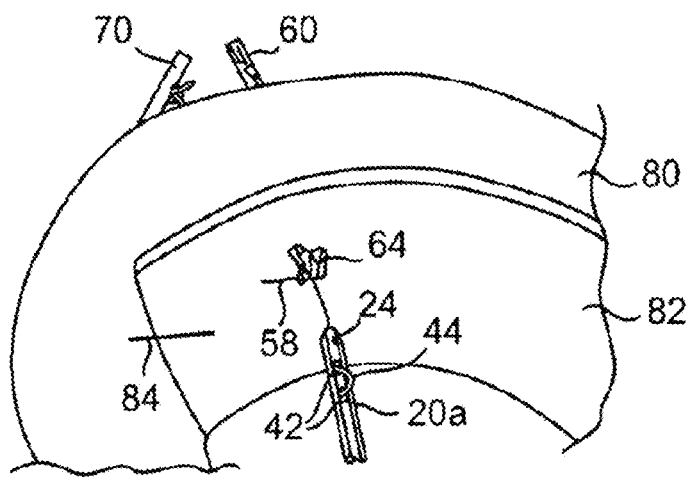
FIG. 37 is a top view of the needle of FIG. 35 after is has been pulled back through the meniscus and implant.

While gripping the handle 16 and the trigger 30 on the applicator 10, the user inserts the needle 20a though the implant 82 and through the meniscus 80 at a second location 88, which may be for example near the first location 86, until the center of the anchor 60 is outside the opposite side of the meniscus 80, as shown in FIG. 35. If the user hasn't already done so, the user next removes the spacer 28 from the rod 24 by grasping the tab 29 and pulling the spacer 28 away from the rod 24. The user then advances the pusher 23 until the anchor 60 is pushed outside the needle 20a, as shown in FIG. 36. The user then retracts the needle 20a, thereby leaving the anchor 60 on the opposite side of the meniscus 80, as shown in FIG. 37.

Figure 38:
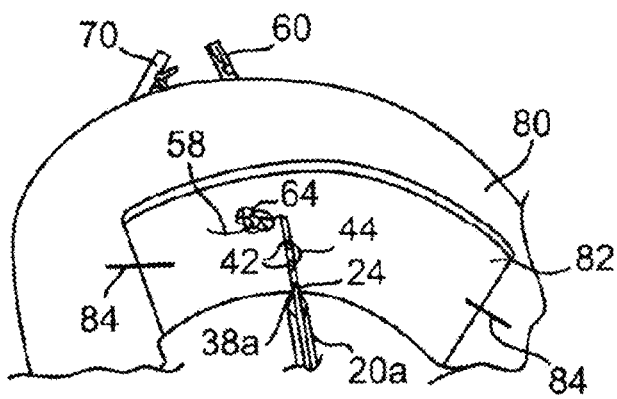
FIG. 38 is a top view of the needle of FIG. 37 with the pusher extended out of the needle.
Figure 39:
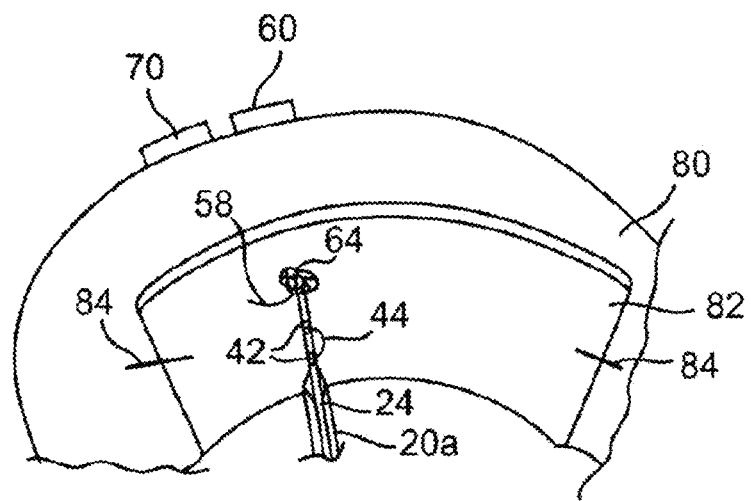
FIG. 39 is a top view of the needle of FIG. 38 with the pusher pushing the knot against the implant.
Figure 40:
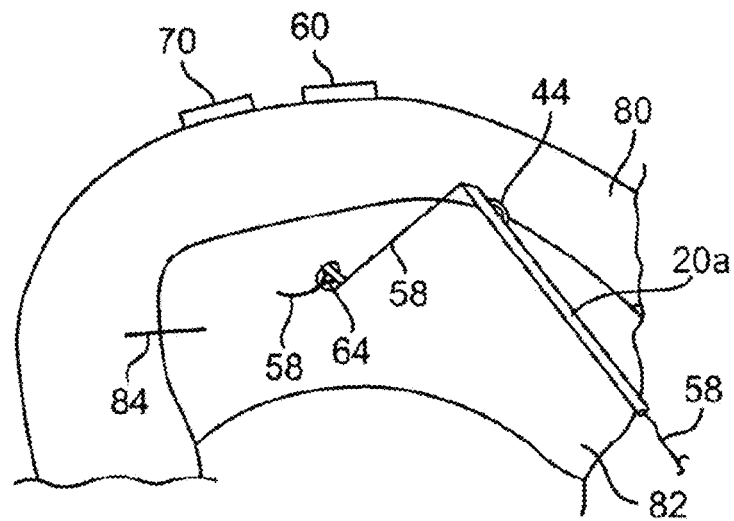
FIG. 40 is a top view of the needle of FIG. 39 after it has been pulled back following knot pushing and suture tensioning.

Having deployed both anchors 60, 70, the user may then advance the pusher 23 via the trigger 30 so that the rod 24 extends approximately 1 cm beyond the point 38a of the needle 20a, as shown in FIG. 38. While gripping the handle 16 and the trigger 30 of the applicator 10, the user then holds the tip of the rod 24 against the knot 64 and pushes the knot 64 to the surface of the implant 82, being careful not to push the knot 64 through the implant 82. The user continues to grip the handle 16 and the trigger 30 while gently pulling on the end 59 of the flexible length 58 of the suture 12 at the proximal end 15 of the body portion 14 of the applicator 10 until slack in the suture 12 is taken up, and the anchors 60, 70 sit flat against the meniscus 80, as shown in FIGS. 39 and 40.

Figure 41:
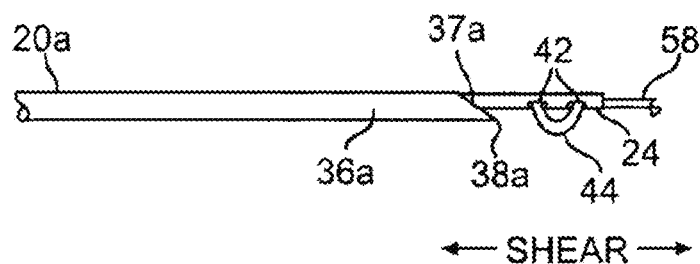
FIG. 41 is a side view of the needle of FIG. 40 with the suture exposed to the needle cutting surface.
Figure 43:
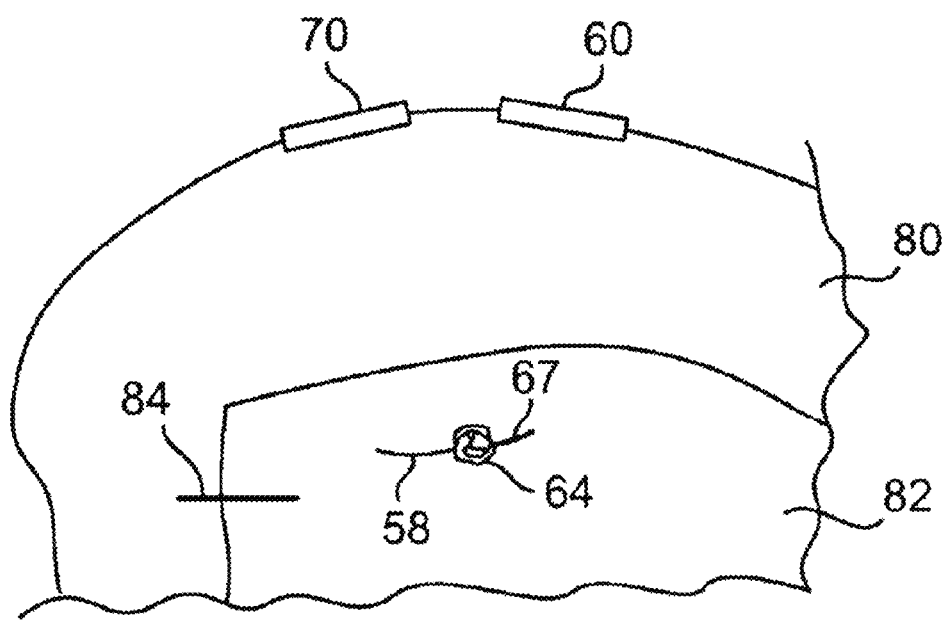
FIG. 43 is a top view of the repaired meniscus with the suture tightly in place.

With the knot 64 now secured, the user may extend the rod 24 of the pusher 23 out of the needle 20a approximately 1 cm. The user may then rotate the pusher 23 up to approximately 180 degrees, or until the slots 42 and the exposed portion 44 of the suture 12 are positioned to come into contact with the cutting surface 37a when the pusher 23 is pulled back toward the proximal end 15 of the body portion 14 of the applicator 10, as shown in FIG. 41. Holding the end 59 of the flexible length 58 that extends out of the proximal end 15, the user may shear the exposed portion 44 of the suture 12 against the cutting surface 37a by sliding the pusher 23 longitudinally against the cutting surface 37a, as shown in FIG. 41, thereby leaving a short tail 67 near the knot 64, as shown in FIG. 43. The pusher 23 may have to be moved back and forth against the cutting surface 37a before the suture 12 is fully cut.

Figure 42:
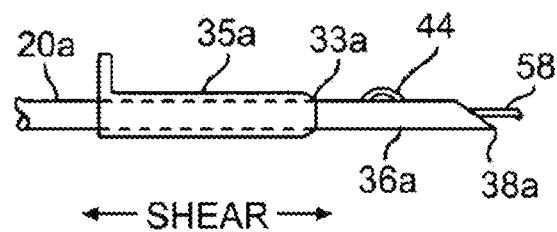
FIG. 42 is a side view of another embodiment of the needle of FIG. 40 with the suture exposed to a cutting surface on a cutting sheath.

In another embodiment, after the knot 64 is secured, while holding the end 59 of the flexible length 58 that extends out of the proximal end 15, the user may shear the exposed portion 44 of the suture 12 against the cutting surface 33a by sliding the cutting sheath 35a along the distal end 36a and toward the point 38a of the needle 20a, as shown in FIG. 42, thereby leaving a short tail 67 near the knot 64, as shown in FIG. 43. The cutting sheath 35a may have to be moved back and forth along the distal end of the needle 20a before the suture 12 is fully cut.

The aforementioned system 1 and method provide an all-inside suture fixation to the implant and meniscus, because the needle 20a of the applicator 10 has not been removed from the patient's body between the deployment of the anchor 70, the pushing of the knot 64, and the cutting of the excess flexible length 58 of the suture 12. This may be beneficial to the patient because it may reduce the time the applicator 10 is in the patient's body, and allows for a single, small entry point of the needle 20a, at the incision, into the patient's body.

The user may then repeat the steps shown in FIGS. 32-43 for any remaining sutures 12 that are needed to complete the fixation of the implant 82 to the meniscus 80. Generally, it may take three or more sutures 12 to secure the implant 82.

Of course, in alternative embodiments, the user may remove the body portion 14 of the applicator 10 and pusher 23 from the cannula 18, and trim the excess flexible length 58 of the suture 12 with scissors, or some other cutting device. The illustrated embodiments are not intended to be limiting in any way.

Also, in alternative embodiments, one or both of the anchors 60, 70 may be the anchor described above that includes one or more barbs. This allows the user to advance the pusher 23 via the trigger 30 only until a distal end of the anchor is located adjacent the point of the needle 20 in an orientation in which the barb is no longer engaged by the wall of the needle 20. When the anchor is in this position, the wall of the needle 20 is no longer exerting pressure on the barb, thereby allowing the barb to be biased outward and away from the body of the anchor. The barb may then be used to engage the anchor with the meniscus 80 so that when the user pulls the needle 20 back through the meniscus 80 and the implant 82, the entirety of the anchor will pull out of the needle 20 without further advancement of the pusher 23.

It is also contemplated that the needle 20 may be designed such that the tab 48 on the anchor 46 may be used to engage the anchor 46 with the meniscus 80 before the anchor 46 exits the needle 20. This allows the entirety of the anchor 46 to be pulled out of the needle 20 when the needle 20 is pulled back through the meniscus 80, rather than pushing the entirety of the anchor 46 out of the needle 20 with the pusher 23, as described in the embodiments above.

Although the above-described procedure was in the context of attaching an implant to a meniscus with needle penetration of the implant and the meniscus in a substantially horizontal stitch, a substantially similar procedure may be used for the placement of other types of stitches, such as vertical and oblique, as would be appreciated by one of skill in the art. The illustrated and described embodiments should not be considered to be limiting in any way.

In addition, although the above-described procedure was in the context of attaching an implant to a meniscus, a substantially similar procedure may be used to repair soft tissue, as would be appreciated by one of skill in the art. The illustrated and described embodiments should not be considered to be limiting in any way. For example, to repair a tear in the meniscus 80 with the suture 12, the needle 20 may be inserted through the meniscus 80 a first location near the tear. The first anchor 70 of the suture 12 may then be delivered to an opposite side of the meniscus 80, and the needle 20 retracted from the meniscus 80, without pulling out of the body. The needle may then be inserted through the meniscus 80 at a second location on an opposite side of the tear as the first location. The second anchor 60 of the suture 12 may then be delivered to the opposite side of the meniscus 80. Once the second anchor 60 is in the proper position, the user may then push the knot 64 to a surface of the meniscus 80 to tighten the suture. The excess of the flexible length 58 of the suture 12 may then be cut with any of the cutting methods described above.

In another embodiment, illustrated in FIGS. 44-52C, a system 100 for repairing a meniscus is provided. The system 100 includes an applicator 110 that is constructed and arranged to deploy the suture 12, which includes the flexible length 58 and the two anchors 60, 70, as described above, to the meniscus. In this embodiment, the applicator 110 includes a body portion 114 that is configured to be grasped by the user. As shown in FIGS. 44 and 45, the body portion 114 includes a pair of extensions 116 at a proximal end 115 of the body portion 114. Each of the extensions 116 is constructed and arranged to engage a finger of the user such that the body portion 114 is may be held in between the fingers in a similar way that a syringe is typically held.

As illustrated in FIG. 44, the body portion 114 of the applicator 110 receives a cannula 118 that extends from a distal end 113 of the body portion 114 in a direction that is away from the proximal end 115. The cannula 118 may be constructed and arranged like the cannula 18 described and illustrated above, and in U.S. Pat. No. 5,928,252, which is hereby incorporated by reference in its entirety, and may be connected to the body portion 114 in a similar manner.

The applicator 110 also includes a needle 120 that has a cutting surface 121 at a distal end thereof. The needle 120 is connected to a distal end of the cannula 118 so that it is operatively connected to the distal end 113 of the body portion 114. Of course, the needle 120 may be considered to be a part of the cannula 118 itself. The needle 120 may be of the same design as the needle 20a discussed above. As such, details of the needle 120 will not will be described in further detail. Instead, reference should be made to the needle previously described and illustrated.

The applicator 110 also includes a pusher 123. The pusher 123 includes a rod 124 (shown in FIG. 46) that extends through a central lumen 112 of the body portion 114, a central bore (not shown) of the cannula 118, and is slidingly received by the needle 120. A knob 126 is attached to one end of the rod 124 and is configured to be grasped by the user so that the user may manipulate the rod 124, as described in further detail below. As shown in FIG. 46, the rod 124 includes proximal end 125 and a distal end 127, which has a smaller diameter than the diameter of proximal end 125, as illustrated. The distal end 127 is configured to include a pair of slots 142 that are similar to the slots 42 discussed above. A central bore 122 extends through the rod 124 and the knob 126 so that the flexible length 58 of the suture 12 may be threaded through the slots 142, through the rod 124, and through the knob 126, as shown in FIG. 46.

As illustrated in FIG. 46, the pusher 123 includes a first projection 128 that projects from the rod 124 and defines a first stop surface 129 on one side thereof. The first projection 128 may be configured as a square or rectangular tab, or may be in the shape of a cylinder. The illustrated embodiment is not intended to be limiting in any way. The knob 126 of the pusher 123 includes a stopper portion 130 that is connected to the rod 124 and defines a second stop surface 131. The pusher 123 also includes a second projection 132 that projects from the rod 124 and defines a third stop surface 133 on one side thereof. The second projection 130 is axially spaced from the first projection 128 and is axially located between the first projection 128 and the distal end 127 of the rod 124.

As shown in FIG. 47, the second projection 130 is also radially spaced from the first projection 128. The radially spacing is defined by angle β, and in the illustrated embodiment, the angle β is about 90 degrees. It is contemplated that the angle β may be in the range of about 10 degrees to about 370 degrees, as will be appreciated in the discussion below. The illustrated embodiment is not intended to be limiting in any way.

As shown in FIG. 45, the body portion 114 defines an outer surface 134 at its proximal end that is configured to engage the stop surfaces 129, 131, 133 described above as the pusher 123 is moved to different positions relative to the body portion 114 and needle 120. The body portion 114 also includes an opening 136, shown in the Figures to be shaped as a keyhole, that is axially connected to the central lumen 112 and is constructed and arranged to receive the first projection 128 and the second projection 130 of the pusher 123, as discussed in further detail below. The arrangement of the opening 136 in the proximal end 115 of the body portion 114 is such that the pusher 123 should be in the proper orientation relative to the body portion 114 in order for the pusher 123 to move toward the needle 120 in an axial direction. Once the first projection 128 or the second projection 130 has passed through the opening, the respective projection 128, 130 is then located within the central lumen 112 of the body portion 114. The central lumen 112 is sized to allow the projections 128, 130 to rotate with the rod 124 about a central axis. However, when one of the projections 128, 130 is positioned within the opening 136, the rod 124 will be prevented from rotating.

FIGS. 48A-53C illustrate portions of the system 100 during different stages of repairing a meniscus or other soft tissue. As shown in FIGS. 48A-C, the pusher 123 is disposed in a first orientation and first axial position relative to the body portion 114 and the needle 120. In this orientation and position, the third stop surface 133 is engaged with the outer surface 134 of the body portion 114 such that pressure applied to the knob 126 toward the body portion 114 will not cause the pusher 123 to move in an axial direction. This allows the first anchor 70 to stay within the needle 120, as shown in FIG. 48C, even if pressure is applied to the pusher 123 via the knob 126. This may allow the user to apply pressure to the applicator 110 via the knob 126 as the needle 120 is initially inserted through the implant 82 and meniscus 80, as described above. For example, the user may hold the body portion 114 and engage the extensions 116 with two fingers, while applying pressure to the knob 126 with a thumb, like a syringe.

Once the needle 120 is in the proper location for the discharge of the first anchor 70, the user may rotate the pusher 123, via the knob 126, to a second orientation, which is 90 degrees from the first orientation, as shown in FIGS. 49A-C. This orientation aligns the second projection 132 of the pusher 123 with the opening 136 of the body portion 114, as shown in FIG. 49B. Because the pusher 123 has not yet been moved axially, the first anchor 70 is still located in the needle 120, as shown in FIG. 49C.

The user may then apply pressure to the pusher 123 in an axial direction via the knob 126 until the first surface 129 of the first projection 128 engages the outer surface 134 of the body portion 114, as shown in FIG. 50A. At this position, the second projection 132 has passed all the way through the opening 136 of the body portion 114 such that is in the central lumen 112. As shown in FIG. 50C, the first anchor 70 has been discharged by the pusher 123 out of the needle 120. Other aspects of the discharge of the anchor 70 are discussed above and shown in FIG. 33.

As discussed above and shown in FIGS. 34 and 35 with reference to the needle 20a, the user may then pull the needle 120 in a similar manner so that it clears the meniscus 80 and the implant 82, and then insert the needle through the implant 82 and the meniscus 80 at a second location. Once the distal end of the needle 120 is in the location where the second anchor 60 should be discharged, the user may then rotate the pusher 123 to a third orientation, as shown in FIGS. 51A-C, which is 90 degrees from the second orientation, and 180 degrees from the first orientation. At this orientation, the first protrusion 128 is aligned with the opening 136, and the second anchor 60 is still located within the needle 120.

The user may then apply pressure to the pusher 123 via the knob 123 until the second stop surface 131 of the stopper 130 engages the outer surface 134 of the body portion 114, as shown in FIGS. 52A-B. As illustrated, in this position, the first projection 128 has passed all of the way through the opening 136 and is in the central lumen 112 of the body portion 114. As shown in FIG. 52C, the second anchor 60 has been discharged from the needle 120 by the pusher 123. Other aspects of the discharge of the second anchor 60 are discussed above and shown in FIG. 36. As discussed above and shown in FIGS. 37-40, the knot 64 of the suture 12 may then be pushed against the implant 82, although in this embodiment, the distal end 127 of the rod 124 of the pusher 123 is used to push the knot 64 rather than the rod 24 shown in FIGS. 37-40. Once the knot 64 has been tightened and any slack is taken out of the flexible length 58 of the suture 12, the pusher 123 may be rotated out of the third orientation, as shown in FIGS. 52A-C so as to shear the flexible length 58 of the suture 12 against the cutting surface 121 of the needle 120. Once the flexible length 58 has been cut, the applicator 110 may be pulled out of the body. The applicator 110 may then be disposed of, or, if desired, may be cleaned, sterilized, and used again.

In another embodiment, as illustrated in FIGS. 54-59, there is provided a system 305 which generally comprises an anchor assembly 310 for use in securing together two or more objects within the body of a patient (e.g., as in re-approximating soft tissue portions or securing an implant to soft tissue), and an inserter 315 for deploying anchor assembly 310 within the body of a patient. Note that in FIGS. 54-59, portions of anchor assembly 310 (i.e., the terminus knot and the slip knot, which will be hereinafter discussed) are shown in schematic form for clarity of illustration.

Figure 60:
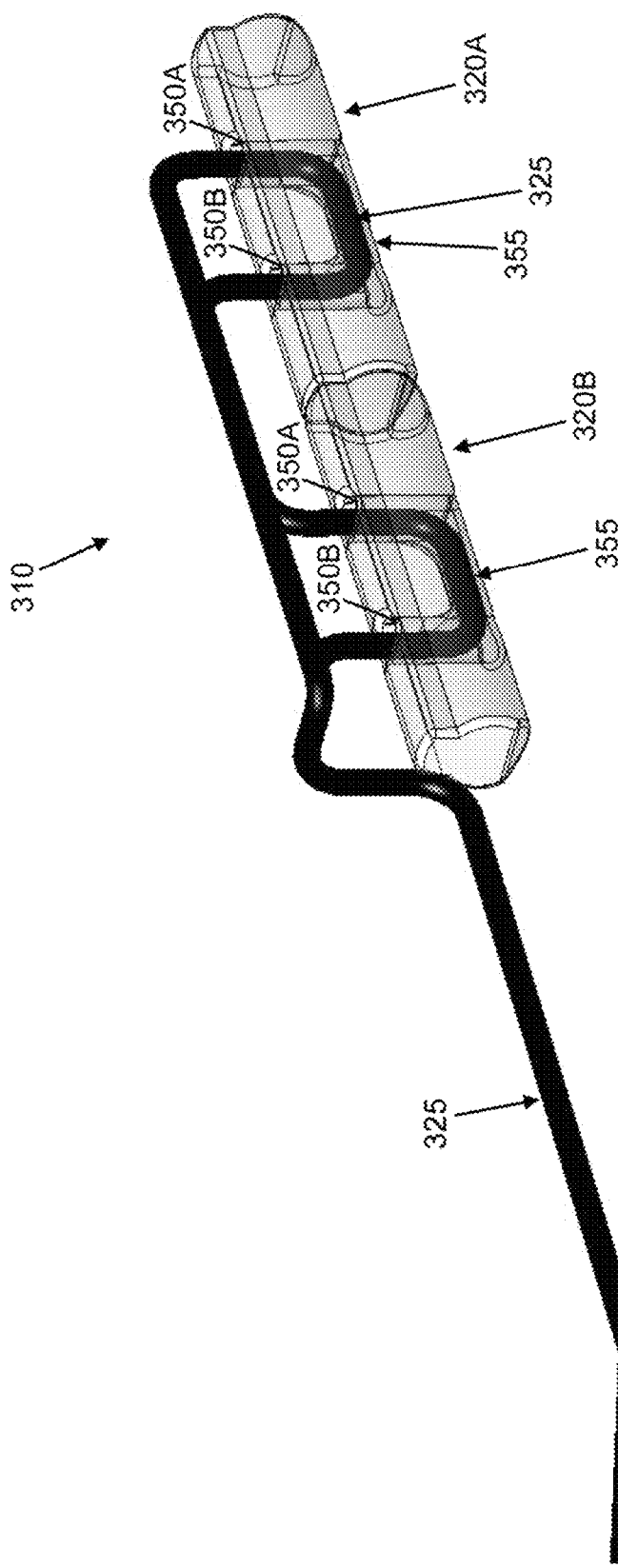
Figure 61:
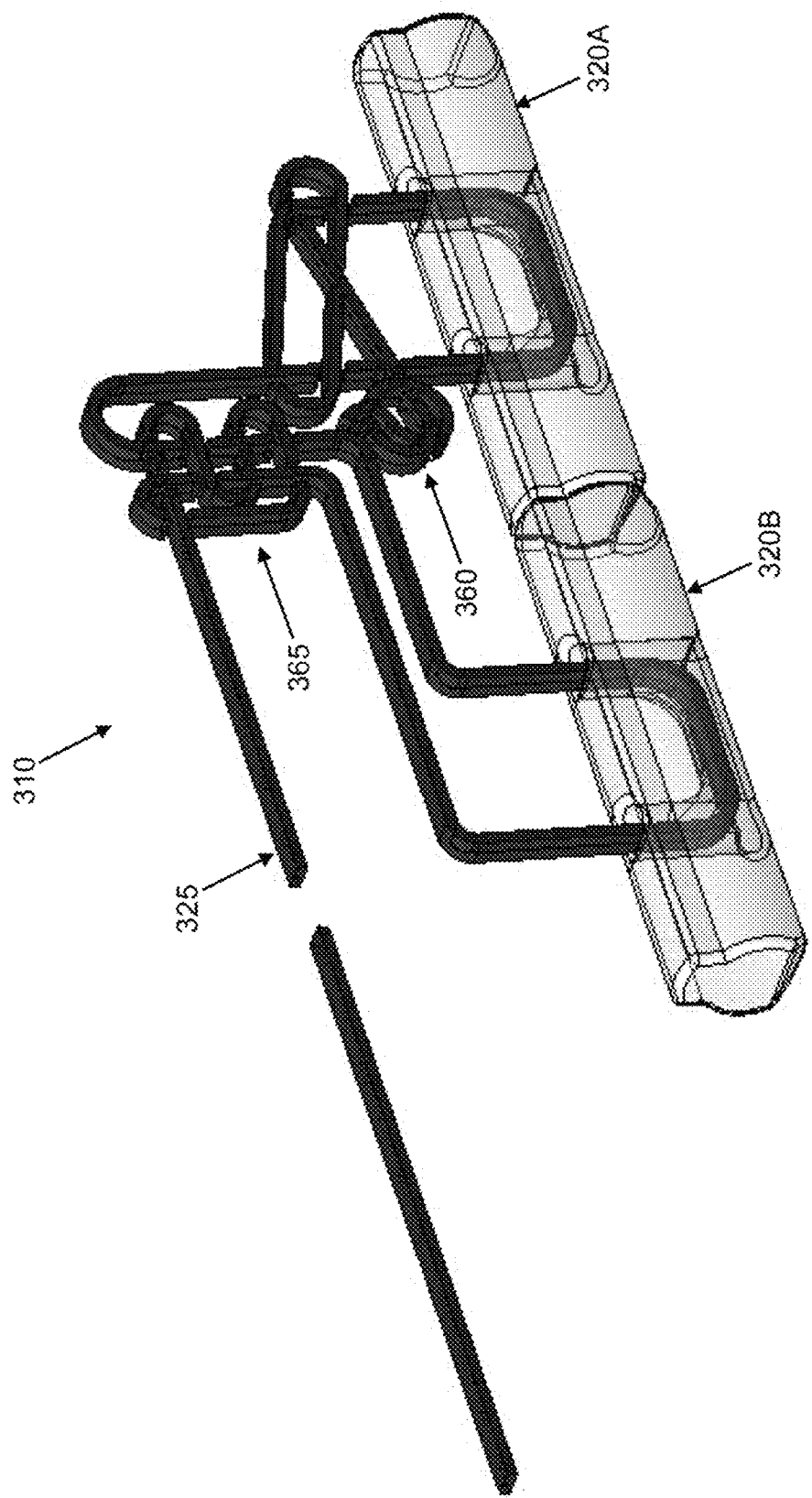
Figure 62:
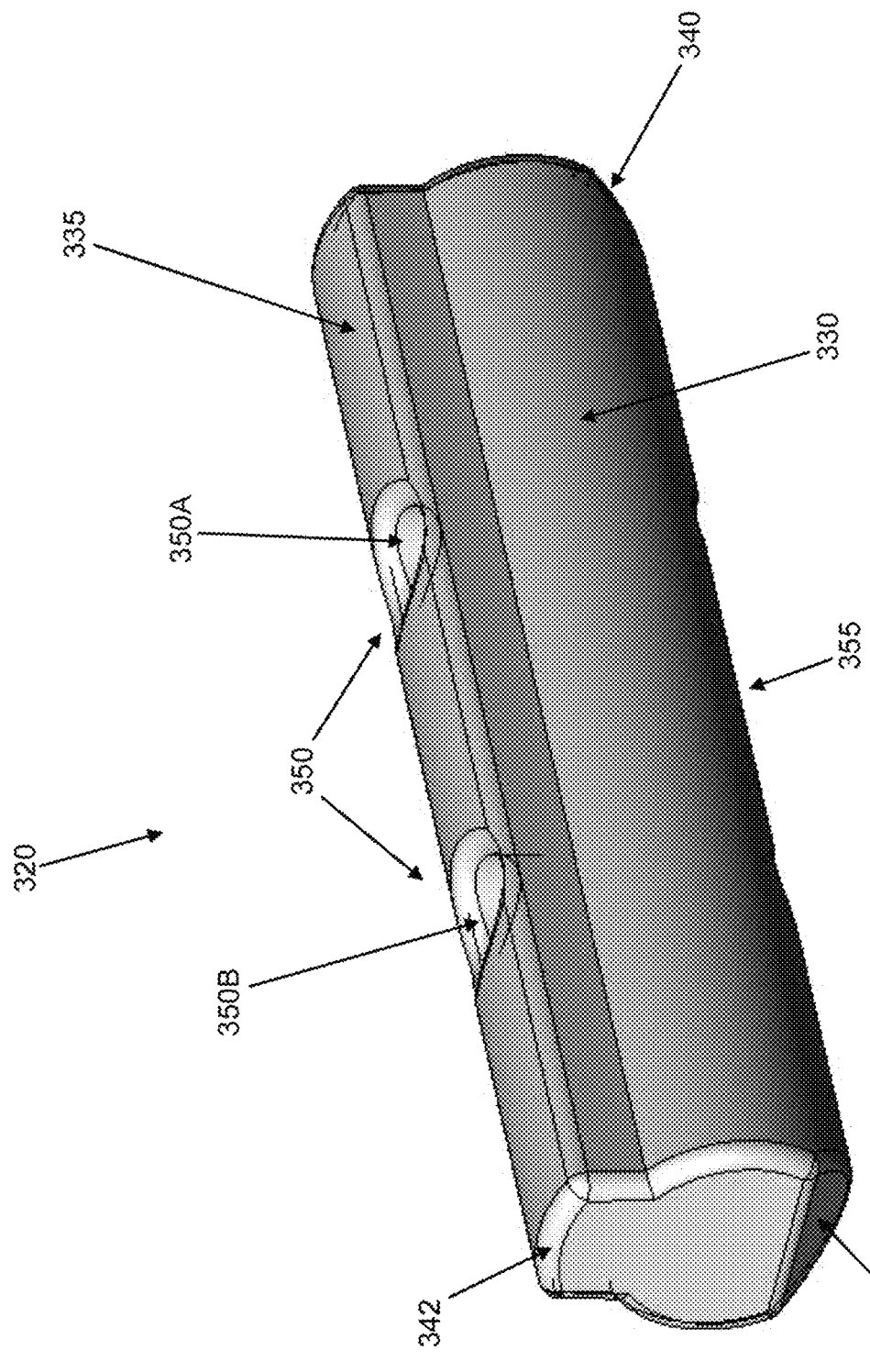
Figure 63:
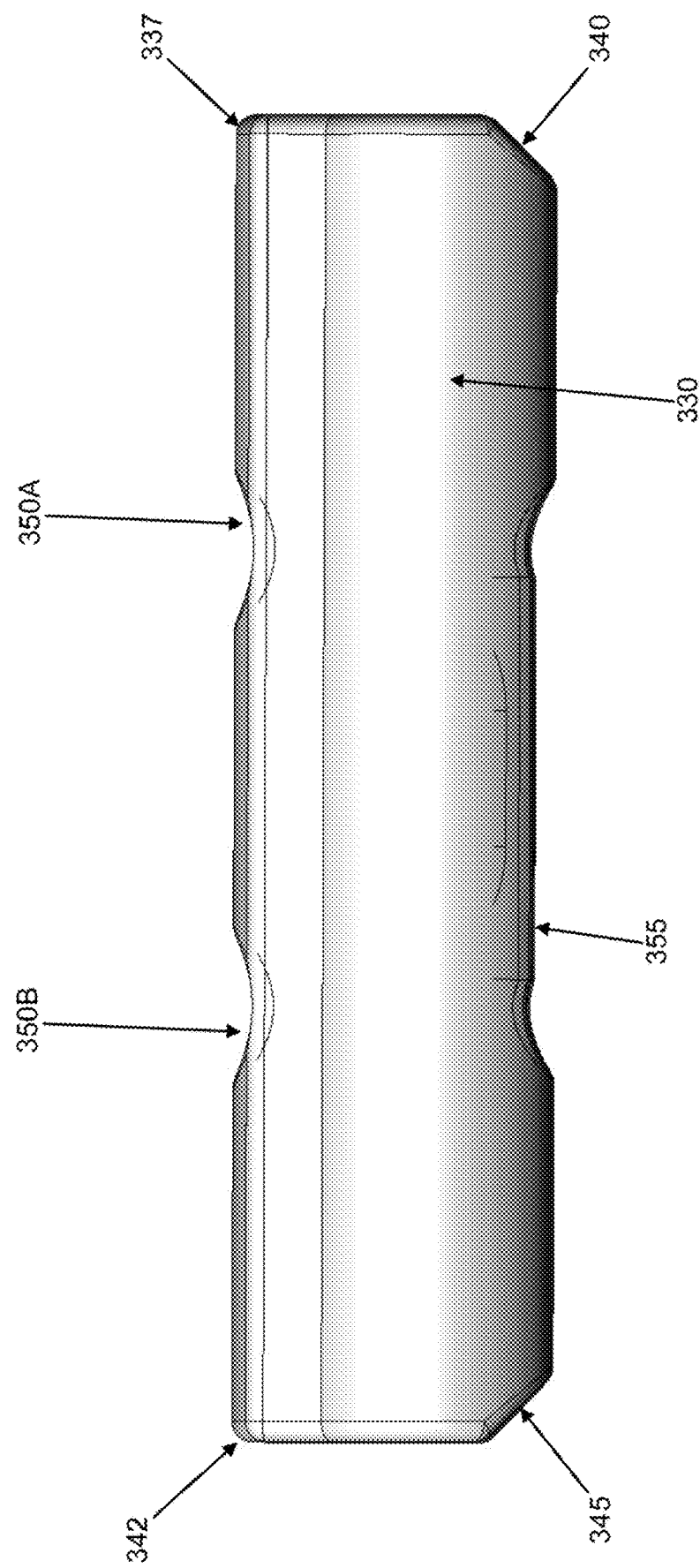
Figure 64:
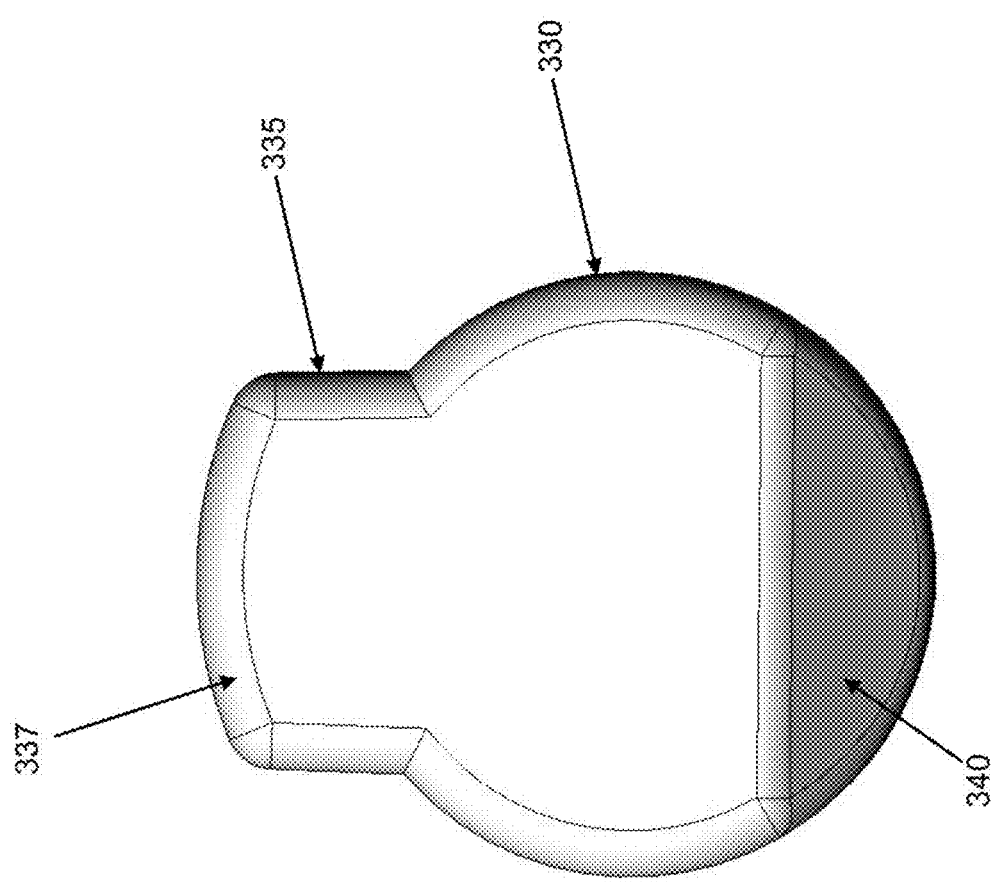
Figure 65:
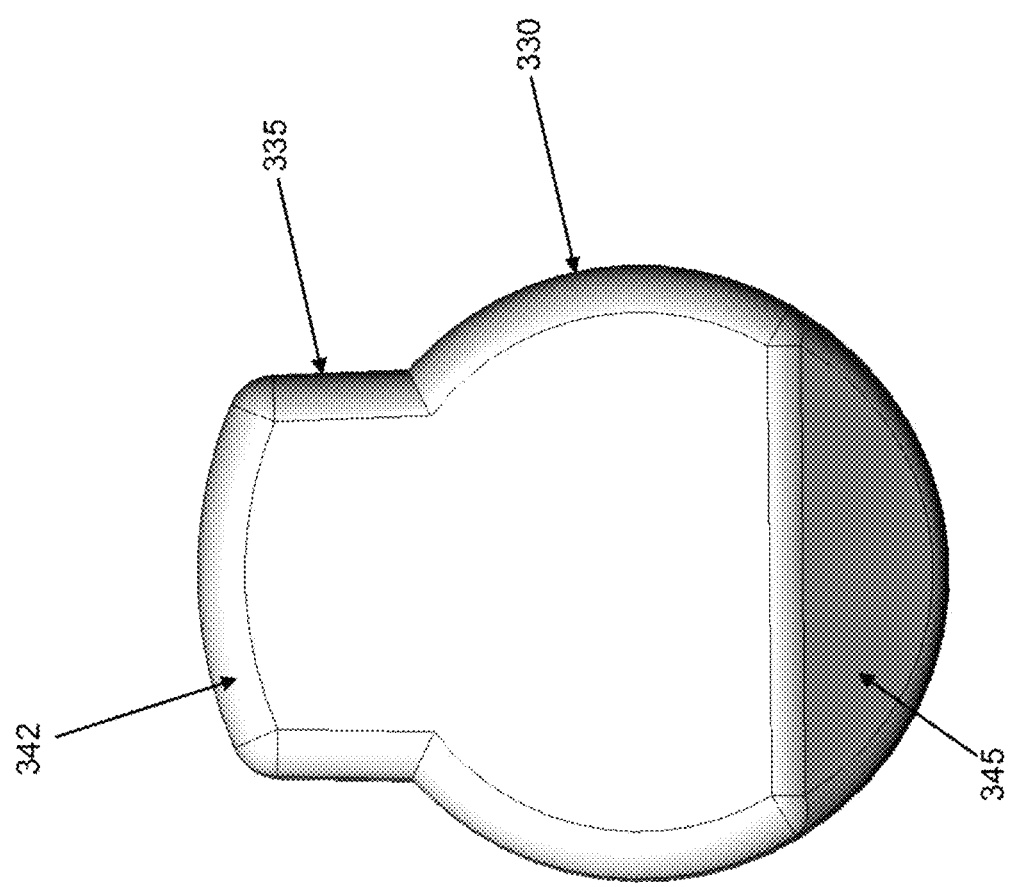
Figure 66:
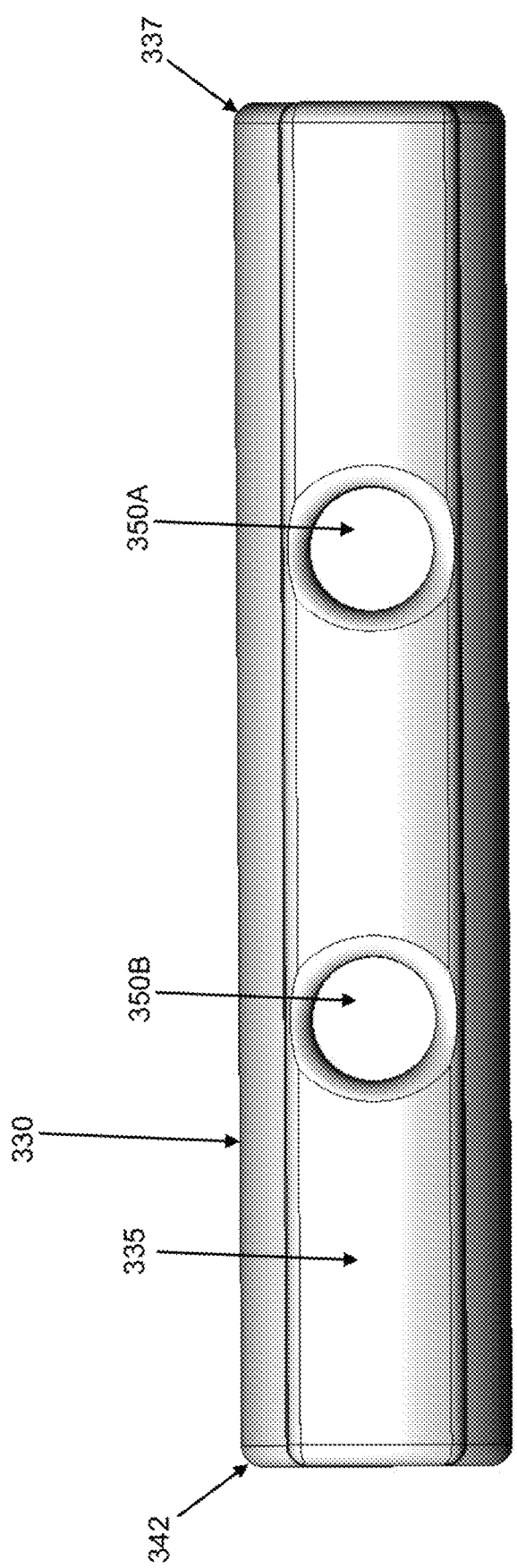

Anchor assembly 310 is shown in further detail in FIGS. 60 and 61. Anchor assembly 310 generally comprises a pair of anchors 320 (i.e., a distal anchor 320A and a proximal anchor 320B) and a suture 325 for adjustably connecting together the pair of anchors 320 (i.e., distal anchor 320A and proximal anchor 320B). Note that in FIG. 60, portions of anchor assembly 310 (i.e., the terminus knot and the slip knot, which will be hereinafter discussed) are shown in schematic form for clarity of illustration, and in FIG. 61, the terminus knot and the slip knot (which will be hereinafter discussed) are shown in one exemplary embodiment.

The pair of anchors 320 (i.e., distal anchor 320A and proximal anchor 320B) are illustrated as being identical to one another and are shown in greater detail in FIGS. 62-67. More particularly, anchors 320 comprise generally cylindrical bodies 330 having upraised portions 335. The distal ends of anchors 320 comprise a rounded leading edge 337, and generally cylindrical bodies 330 may be beveled or chamfered at 340. The proximal ends of anchors 320 comprise a rounded trailing edge 342, and generally cylindrical bodies 330 may be beveled or chamfered at 345. Rounded edges 337, 342 help facilitate smooth passage of anchors 320 along the shaft of inserter 315 and through soft tissue, and minimize trauma to the tissue, as will hereinafter be discussed. Bevels 340, 345 may facilitate passage of anchors 320 along the shaft 370 of inserter 315, as will hereinafter be discussed.

Figure 67:
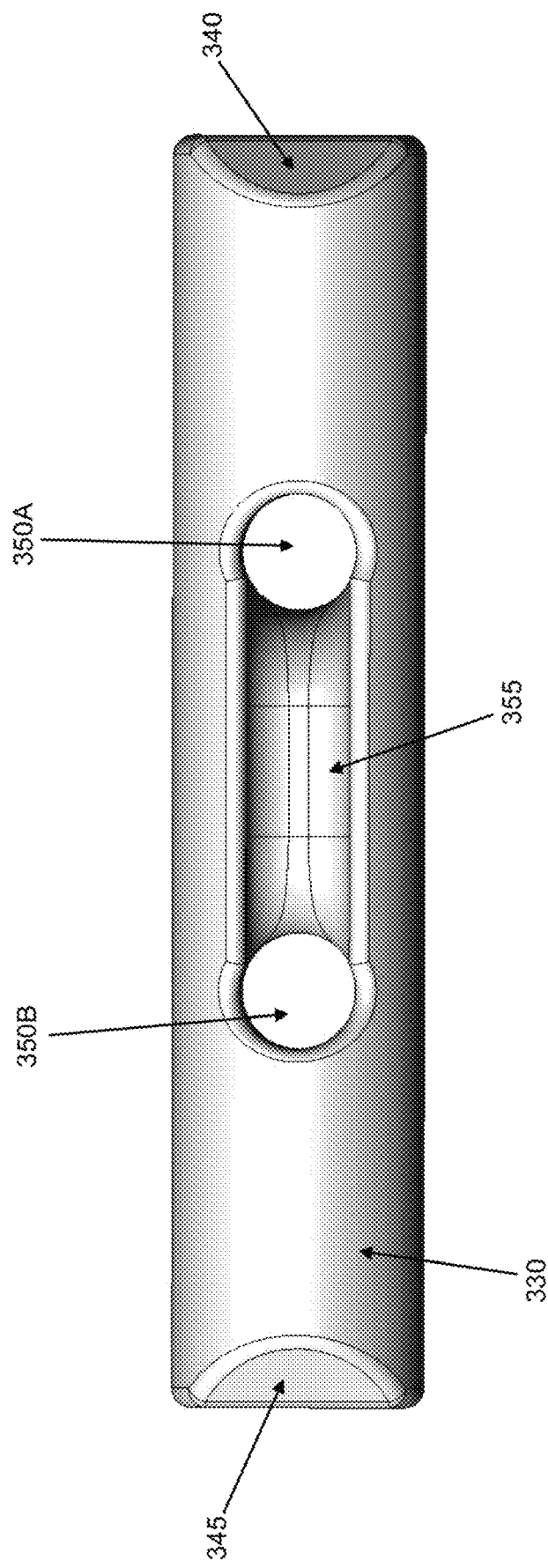
Figure 71:
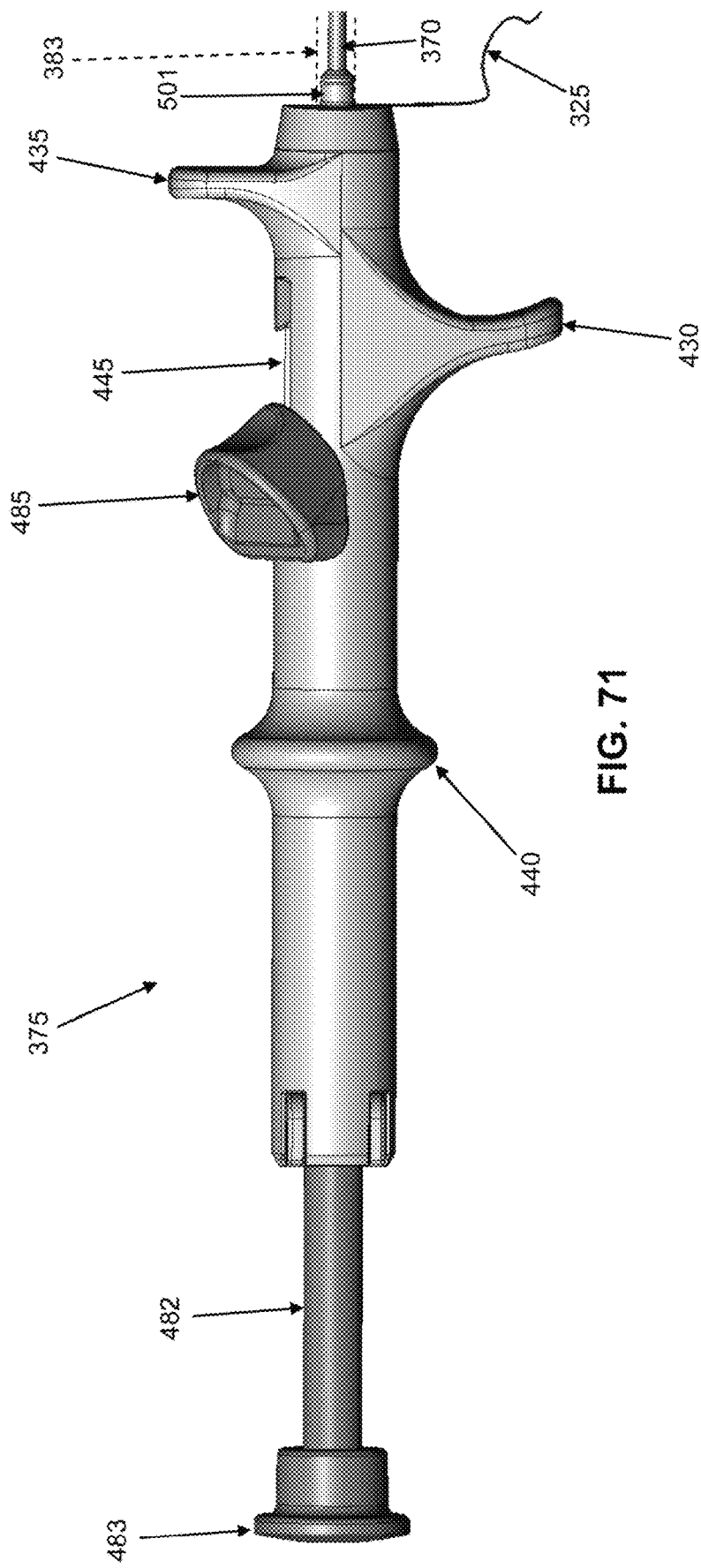
FIGS. 71-75 are schematic views showing further details of the inserter of the system of FIGS. 54-59, specifically the proximal portions of the inserter.
Figure 72:
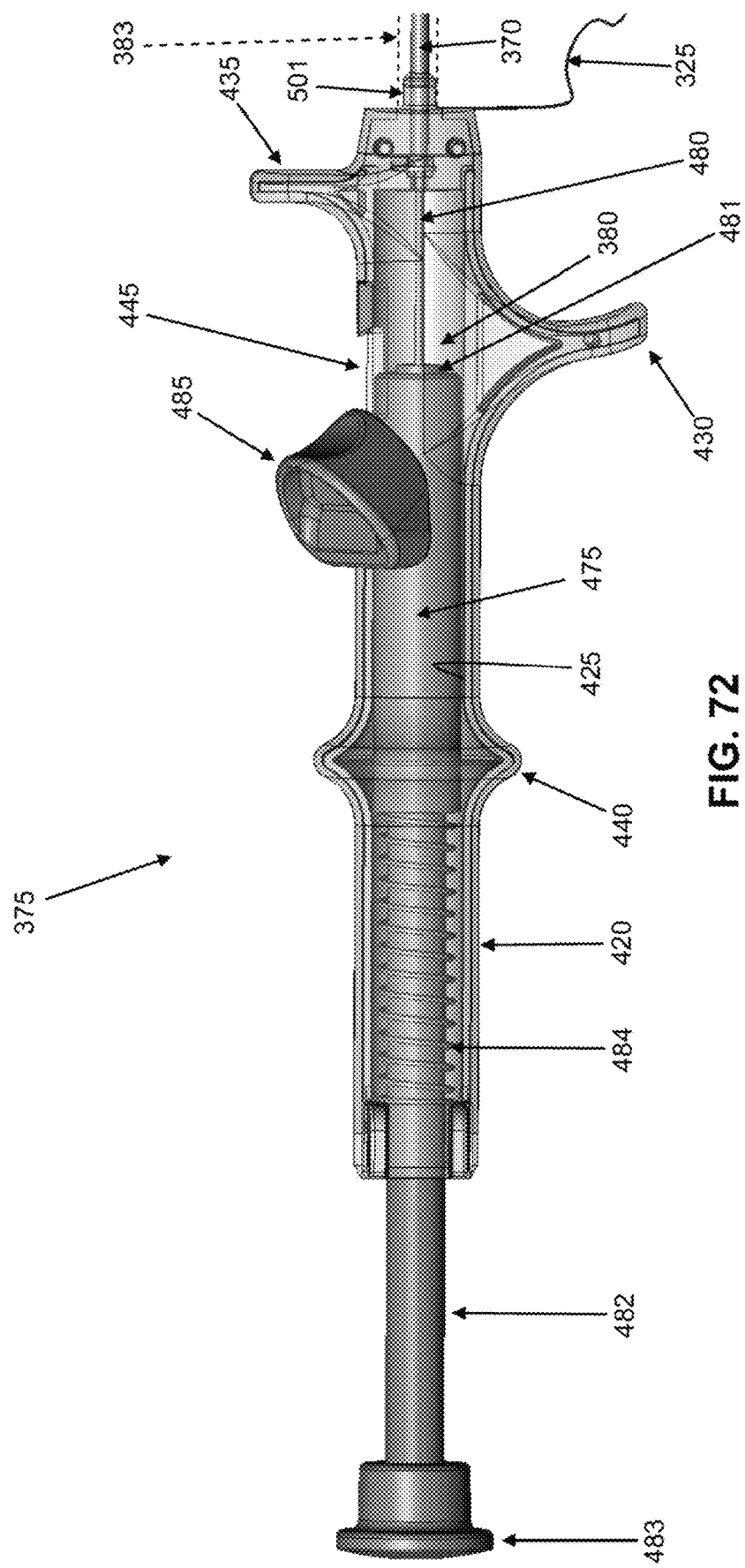
Figure 73:
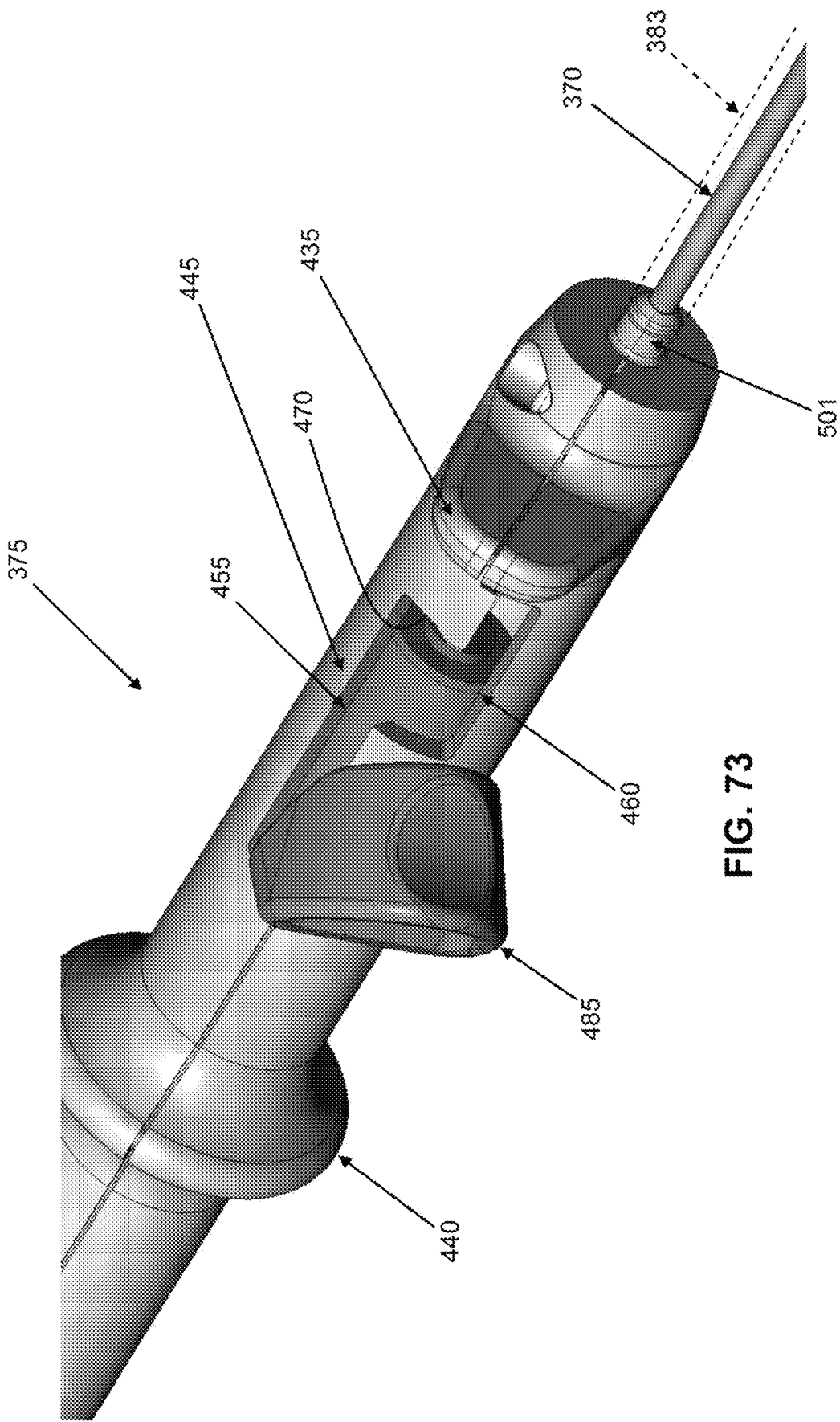
Figure 74:
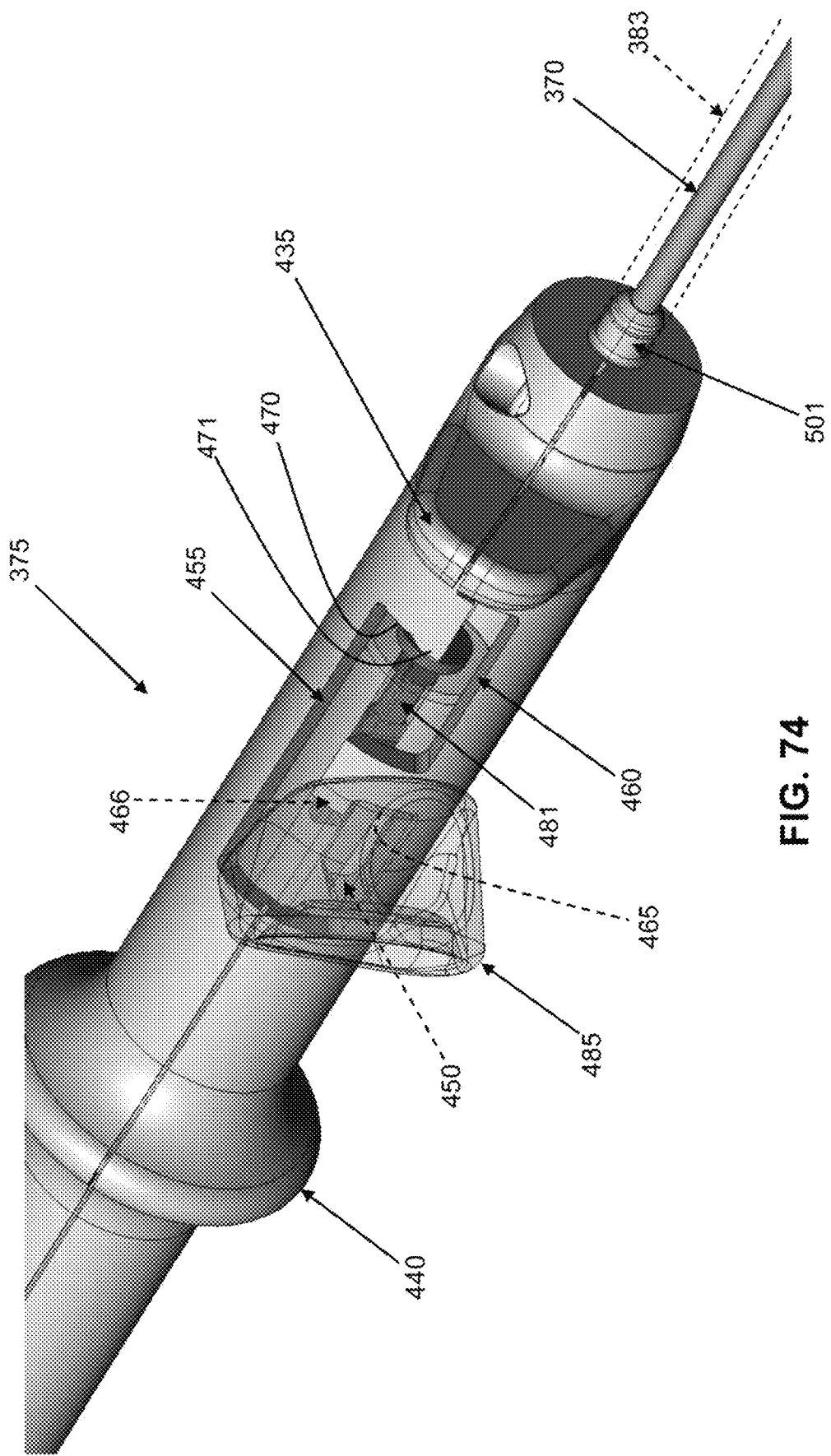
Figure 75:
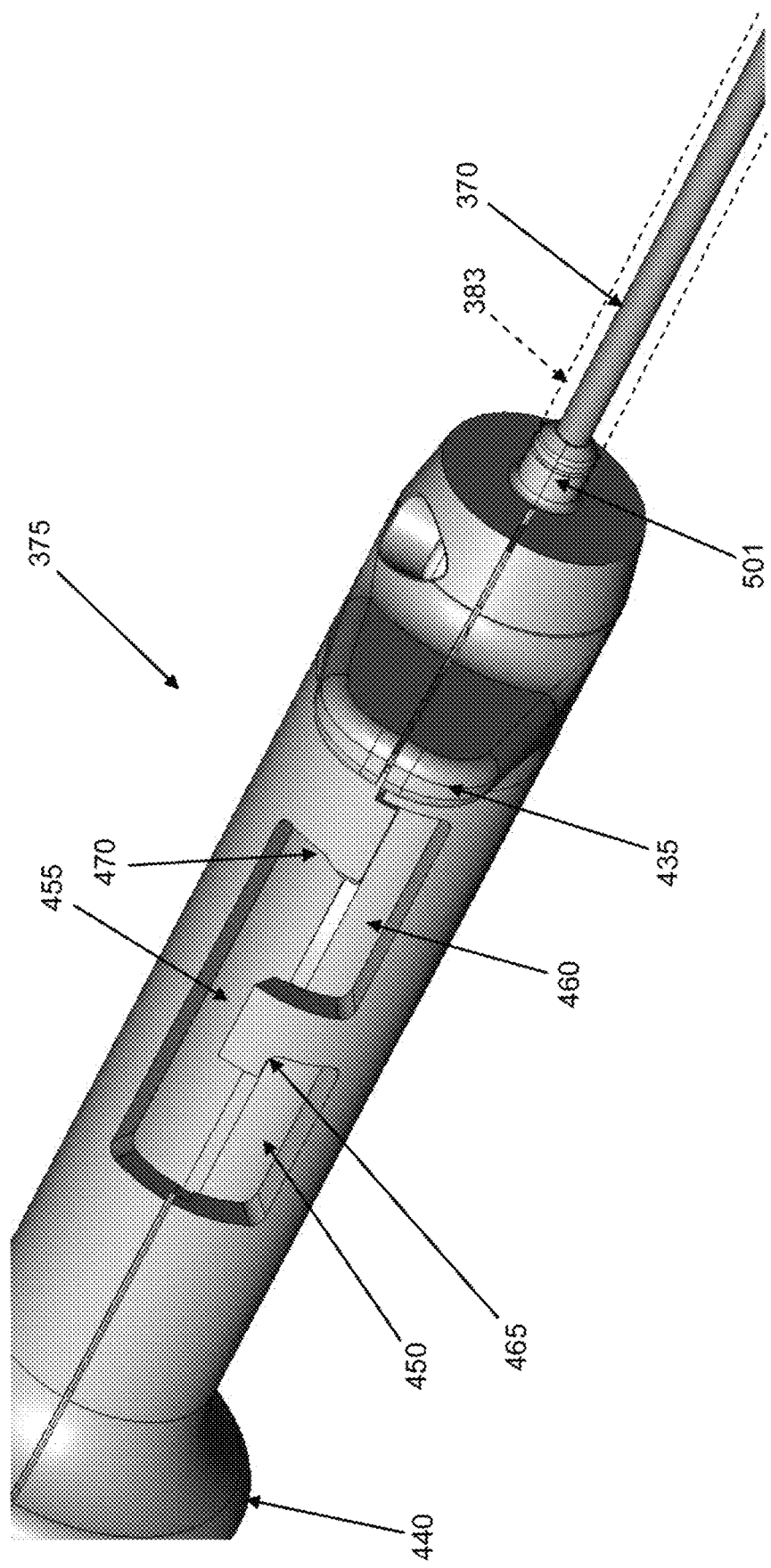

A pair of bores 350 (i.e., a distal bore 350A and a proximal bore 350B) extend through generally cylindrical bodies 330 and upraised portions 335 of anchors 320. Bores 350 are sized to slidably receive suture 325 therethrough, as will hereinafter be discussed. As illustrated in FIG. 67, A slot 355 connects the lower ends of bores 350 (i.e., distal bore 350A and proximal bore 350B) to one another. Slot 355 is sized so that when suture 325 is received in slot 355, suture 325 does not extend beyond the outer perimeter of generally cylindrical bodies 330. As a result, when anchors 320 are disposed within the lumen of the shaft of inserter 315 (see below), suture 325 will not cause any vertical displacement of anchors 320 within the lumen of the shaft.

As seen in FIGS. 61 and 68-70, suture 325 is attached to anchors 320 by passing suture 325 down distal bore 350A of distal anchor 320A, proximally along slot 355 in distal anchor 320A, up proximal bore 350B of distal anchor 320A, down distal bore 350A of proximal anchor 320B, proximally along slot 355 in proximal anchor 320B, up proximal bore 350 of proximal anchor 320B and then proximally along inserter 315.

Figure 59:
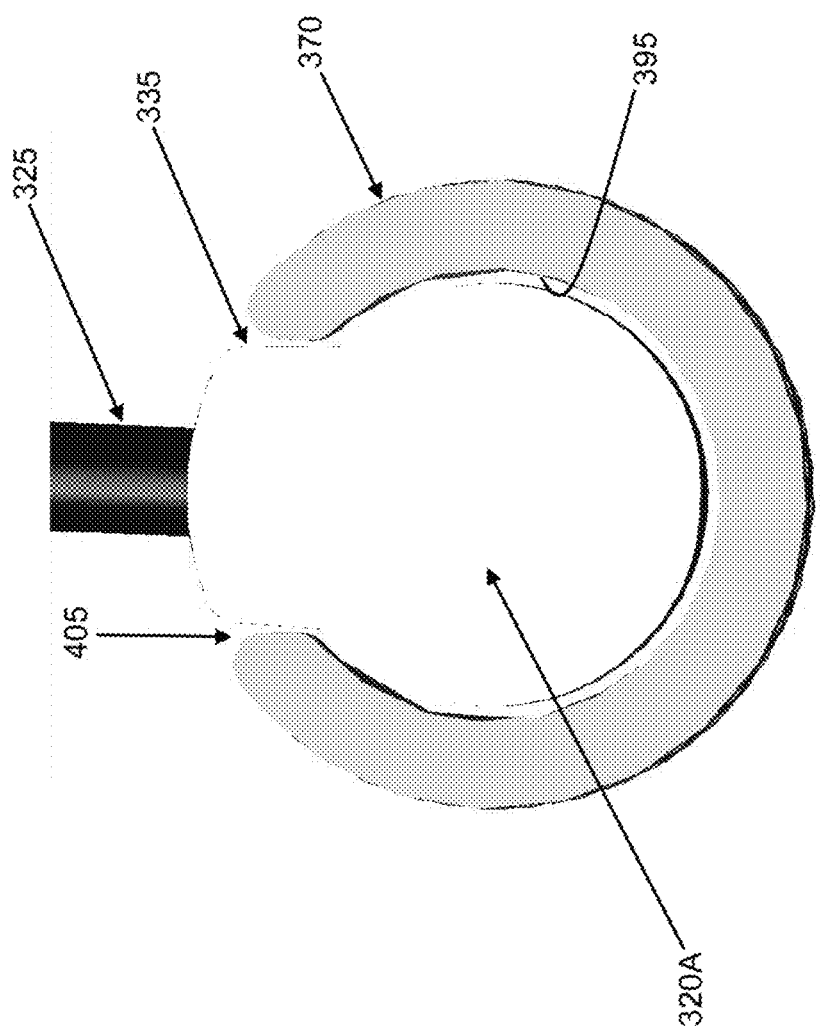

Note that by providing anchors 320 with upraised portions 335, and by routing suture 325 vertically through anchors 320 so that the suture passes through both cylindrical bodies 330 and upraised portions 335, anchors 320 have increased material adjacent to the suture so as to provide greater strength to the construct. Further, such a suture routing also separates the suture from the edges of slot 405, as illustrated in FIG. 59, which may minimize the risk of abrasion of the suture 325 by contact on the edges of slot 405. However, the upraised portion 335 is not so tall as to extend beyond slot 405, and thus the shape of anchor 320 provides for high strength while still maintaining a low profile to minimize trauma to the soft tissue and/or implant during implantation.

The distal end of suture 325 is secured to distal anchor 320A. More particularly, and looking now at FIGS. 61 and 68-70, in one embodiment of the present invention, the distal end of suture 325 comprises a terminus knot 360 which is formed in the length of suture entering distal bore 350A of distal anchor 320A and the length of suture exiting proximal bore 350B of distal anchor 320A. Forming terminus knot 360 in this manner may provide a secure knot in the suture while also maintaining a low profile, particularly while the anchors are positioned within shaft 370. Such a low profile knot may provide improved tactile feedback for the surgeon during implantation as less force will be required to pass the knot through the tissue and/or implant. It should be appreciated that terminus knot 360 may be replaced/omitted by braiding, fusing or gluing the distal end of suture 325 to distal anchor 320A so as to secure the distal end of suture 325 to distal anchor 320A, and/or by forming the suture integral with distal anchor 320A.

Still looking now at FIGS. 61 and 68-70, a slip knot 365 is formed in suture 325 in the length of suture entering distal bore 350A of proximal anchor 320B and the length of suture exiting proximal bore 350B of proximal anchor 320B. Slip knot 365 is formed such that when anchors 320A, 320B have been appropriately deployed in the body of a patient, pulling on the proximal end of suture 325 locks the slip knot, whereby to set the expanse of suture extending between distal anchor 320A and proximal anchor 320B (and hence secure together two or more objects within the body of a patient, for example, re-approximating two portions of tissue or securing an implant to remaining tissue). In one embodiment of the invention, slip knot 365 may be a so-called one twist half hitch (OTHH) knot. Forming slip knot 365 in this manner may provide a secure knot in the suture. It should also be appreciated that "mirror" images of the terminus knot 360, and/or the slip knot 365, and/or combinations thereof may also be used. One such alternative slip knot is illustrated in FIGS. 68A-70A, where slip knot 365' is a mirror image of slip knot 365 (though all other features described as to FIGS. 68-70 apply equally to the same features illustrated in FIGS. 68A-70A).

Thus it will be seen that anchor assembly 310 comprises a distal anchor 320A, a proximal anchor 320B, and a suture 325 which connects together distal anchor 320A and proximal anchor 320B, with a terminus knot being formed at distal anchor 320A and a slip knot 365 (or 365') being formed between the anchors 320A, 320B.

Looking next at FIGS. 54-59 and 68-75, inserter 315 generally comprises a shaft 370, a handle 375 and a pushrod assembly 380 (see FIGS. 56, 58, 69 and 72). Inserter 315 may also include a sheath 383.

More particularly, shaft 370 generally comprises a hollow tube having a distal end 385 (FIG. 54), a proximal end 390 and a lumen 395 (FIG. 58) extending therebetween. Distal end 385 of shaft 370 terminates in a sharp point 400. A slot 405 (FIG. 68) is formed in distal end 385 of shaft 370 and terminates in a proximal shoulder 410.

Figure 58:
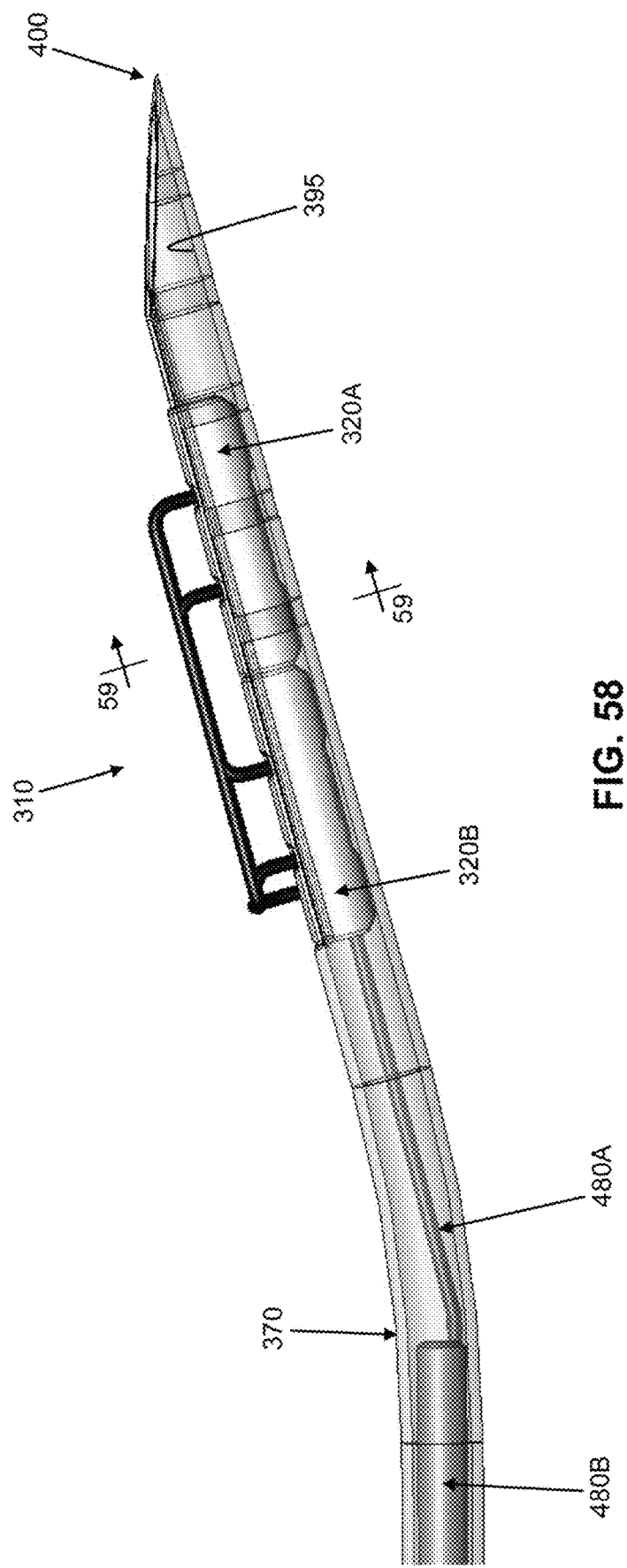

Shaft 370 is sized to slidably receive anchors 320 therein. More particularly, and as seen in FIGS. 58, 59 and 69, generally cylindrical bodies 330 of anchors 320 are slidably received within lumen 395 of shaft 370, with upraised portions 335 of anchors 320 being slidably received in slot 405 of shaft 370. Note that the disposition of upraised portions 335 of anchors 320 in slot 405 provides anchors 320 with a known disposition relative to shaft 370 and prevents anchors 320 from rotating relative to shaft 370 (and the remainder of inserter 315) when anchors 320 are disposed in shaft 370. Note also that, as seen in FIG. 59, upraised portions 335 of anchors 320 do not extend radially beyond the perimeter of shaft 370 (i.e., the outermost portions of anchors 320 are contained within an axial projection of the cross-section of shaft 370), so that upraised portions 335 of anchors 320 do not engage tissue as shaft 370 of inserter 315 is advanced through tissue. A dimple 415 (FIG. 69) may be formed in lumen 395 just proximal to sharp point 400. Dimple 415 provides nominal resistance to the passage of anchors 320 along lumen 395, such that anchors 320 cannot accidentally fall out of the distal end of shaft 370 and/or be accidentally forced out of the distal end of shaft 370 when inserter 315 is repositioned; at the same time, however, anchors 320 can be driven past dimple 415 and out of the distal end of shaft 370 with the force generated by pushrod assembly 380, as will hereinafter be discussed. It should be appreciated that dimple 415 also provides audible and/or tactile feedback to the surgeon which indicates when an anchor 320 is driven past dimple 415 (and out the distal end of shaft 370). Note that bevels 340 at the distal ends of anchors 320 facilitate passage of anchors 320 past dimple 415, and further may help to reduce potential trauma to the anchors themselves during passage past the dimple. Shaft 370 may be straight or curved, as desired.

Note that, inasmuch as shaft 370 is fixed to handle 375 and inasmuch as anchors 320 are fixed against rotation relative to shaft 370 (i.e., by virtue of upraised portions 335 of anchors 320 being disposed in slot 405 of shaft 370), the user will always know the rotational disposition of anchors 320, even when the distal end of shaft 370 is disposed at a remote location within the body, from the rotational disposition of handle 475.

Still looking now at FIGS. 54-59 and 68-75, handle 375 comprises a body 420 (FIG. 72) having a bore 425, a first grip 430, a second grip 435 and a third grip 440. Body 405 comprises a slot 445 (FIG. 75) having a first portion 450, a second portion 455 and a third portion 460. A first shoulder 465 is formed at the distal end of first portion 450 and separates first portion 450 from second portion 455, and a second shoulder 470 is formed at the distal end of second portion 455 and separates second portion 455 from third portion 460. The first shoulder 465 may also include a proximal projection 466 such that, due to the bias of spring 484, a button actuator 485 (and thus pusher 480, both discussed below)) would be trapped against first shoulder 465. Thus, such a position may be suitable for transport and packaging of inserter 315, as well as a beneficial pre-operative and starting position since the actuator and pusher can only be actuated by interaction of the surgeon or other user (e.g., by a proximal force on the actuator 485 or end cap 483 and proximal extension 482, as discussed below). Similarly, the second shoulder 470 may include a proximal ramp 471 which, similar to the proximal projection 466, may assist in seating the actuator 485 against the second shoulder 470 until the surgeon is ready to navigate to the third portion 460. The ramp 471 may be less severe of a shape as compared to projection 466, however, since the force from the spring is less, if not nonexistent, and there is less of a need to protect against movement of the actuator 485 due to this position occurring during mid-surgery, rather than during packaging and shipping. Instead, ramp 471 may be useful to provide a tactile response to the surgeon as the surgeon navigates slot 445 and reaches the third portion 460.

Pushrod assembly 380 generally comprises a cylinder 475 (FIG. 72) which is sized to be slidably received in bore 425 of body 420 of handle 375, a pusher 480 (FIGS. 56, 58, 69 and 72) which is secured to the distal end of cylinder 475 and is sized to be slidably received in lumen 395 of shaft 370, and an extension 482 (FIG. 72) which is secured to the proximal end of cylinder 475 and is sized to extend proximally out of body 420 of handle 375.

Pusher 480 may be formed of any material desired. For example, pusher 480 may be formed of superelastic Nitinol so that pusher 480 may both be naturally lubricious for ease of passing through shaft 370 and flex as it moves through a curved portion of shaft 370. If desired, pusher 480 may have a narrowed width at one or more portions along its length so as to further enhance flexibility. By way of example but not limitation, pusher 480 may comprise a distal component 480A (FIG. 58) formed out of a relatively thin Nitinol rod and a proximal component 480B formed out of a thicker Nitinol rod or a thicker, less flexible material (e.g., stainless steel). Pusher 480 may be secured to cylinder 475 by securing pusher 480 to another member (e.g., a connector 481, FIG. 72) which is itself secured to cylinder 475. Such a construction can be advantageous where the proximal end of pusher 480 is relatively thin (i.e., relative to cylinder 475) and made out of metal, and cylinder 475 is relatively wide (i.e., relative to the proximal end of pusher 480) and made out of plastic, since connector 481 can be of intermediate width (which makes it easier to secure to cylinder 475) and made out of metal, so that pusher 480 can be connected to connector 481 by crimping (e.g., by grinding a circumferential groove into the proximal end of pusher 480, and then crimping connector 481 onto the circumferential groove in pusher 480). In one example, the pusher 480 may have a "D"-shaped cross-section (not shown), which provides a flat surface on one side. This shape may provide for even further improved action of the pusher within shaft 370, particularly through any bend along the length of the shaft which could otherwise cause the pusher to crimp. The connection between pusher and connector 481 may also thus be "D"-shaped, which may provide an improved connection between the elements and inhibit rotation of the pusher relative to cylinder 475.

Extension 482 (FIG. 72) terminates in an end cap 483. A spring 484 is disposed within bore 425 of body 420, as illustrated the spring may be positioned coaxially over extension 482, and biases cylinder 475, and hence pusher 480, distally. A button actuator 485 is secured to cylinder 475 of pushrod assembly 380 and extends through slot 445 in body 420. If desired, button actuator 485 may be contoured (e.g., "cupped") and/or textured so as to facilitate engagement by the finger of a user during use (e.g., such as when the user is wearing a wet glove, etc.). Button actuator 485 allows the user to move cylinder 475 within body 420 (and hence pusher 480 within shaft 370) as will hereinafter be discussed.

More particularly, the thumb (or another finger) of a user can be used (in conjunction with spring 484) to step button actuator 485 through a series of motions within slot 445 in body 420, whereby to step pusher 480 through a series of motions within shaft 370 so as to provide controlled deployment of anchors 320 from the distal end of shaft 370. More particularly, by moving button actuator 485 from first portion 450 of slot 445 into (and along) second portion 455 of slot 445, and then moving button actuator 485 into (and along) third portion 460 of slot 445, pusher 480 will be stepped through a corresponding series of motions with shaft 370 so as to provide controlled deployment of anchors 320 from the distal end of shaft 370, as will hereinafter be discussed. Likewise, instead of actuator 485, extension 482 and end cap 483 may instead be engaged by a user's hand to step pusher 480 through the series of motions to provide controlled deployment of anchors 320. While spring 484 may not have sufficient force to actually perform the deployment of anchors 320, the spring biases actuator 485, and thus pusher 480, in a distal direction such that the spring force is in the same direction as the deployment actions of the user. As such, the user does not need to apply additional force during deployment of the anchors 320 to overcome the spring force (except when moving the actuator 485 away from engagement with the first and second shoulders 465, 470).

Figure 76:
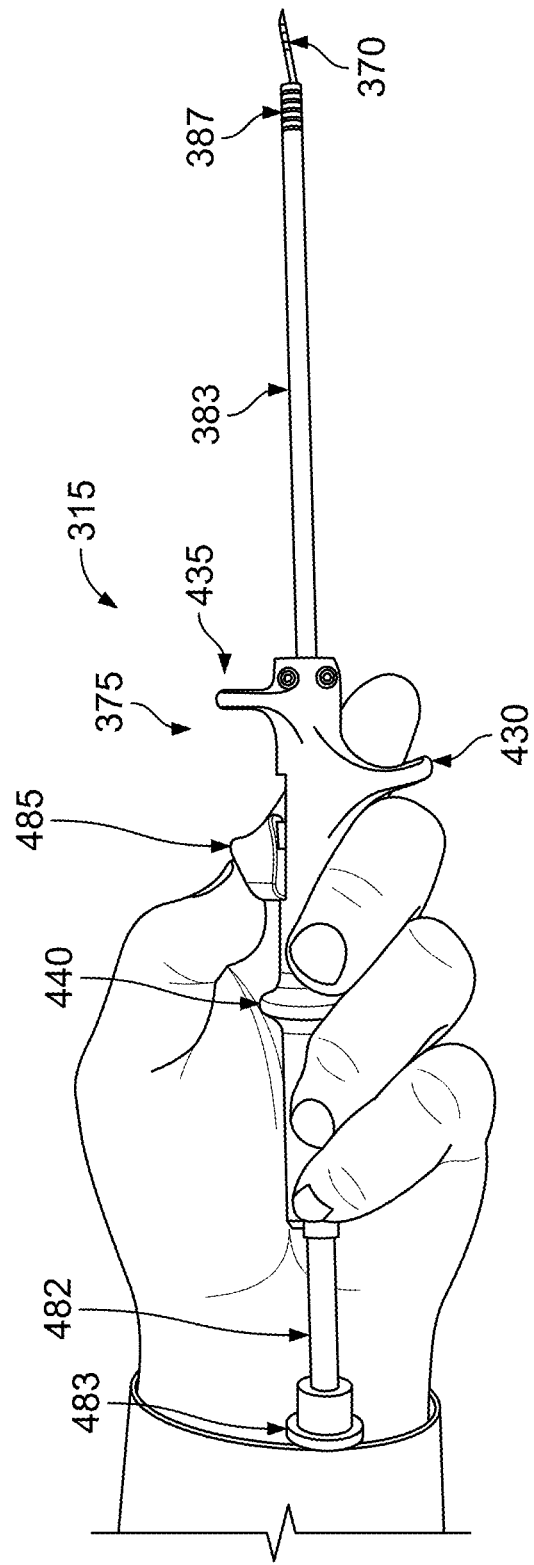
FIGS. 76-82 illustrate exemplary uses of the system of FIGS. 54-59.

Further, sheath 383 may be disposed over at least a portion of shaft 370. Sheath 383 comprises a distal end 490 (FIG. 54), a proximal end 495 and a lumen 500 extending therebetween. The lumen has a diameter sufficient for passage of shaft 370 therethrough, and in instances where, as illustrated, the shaft 370 includes a bend along its length, the lumen may have a diameter sufficient to allow passage of such a nonlinear shaft 370 therethrough. Sheath 383 may also have a length that is somewhat shorter than the length of shaft 370. Further, the sheath may be cut even shorter, if desired, by trimming a desired length of the distal portion of the sheath (see FIG. 76, cutting lines 387). In use, as discussed below, if the user determines preoperatively that a longer length of shaft 370 should be available for passage through the tissue or implant, the user can remove the sheath from the shaft 370 and trim the sheath at cutting lines 387, and then re-sheath the shaft 370 and continue with the procedure. The user may make this determination prior to use of the inserter 315 or by positioning the distal end of inserter 315 through the tissue or implant and determining whether the sheath should be shorter to provide for added length of shaft 370 extending distally from the sheath. Proximal end 495 of sheath 383 is releasably mounted to handle 375 (e.g., by fitting sheath 383 over an extension 501 formed on handle 375, such as by a press-fit engagement) such that the distal end of shaft 370 normally protrudes from the distal end of sheath 383. Sheath 383 may be selectively detached from handle 375 (e.g., dismounted from extension 501 of handle 375) and moved distally in order to temporarily cover the distal end of shaft 370 (e.g., while the distal end of system 305 is being advanced to a remote site within the body). Sheath 383 can then be returned proximally and re-mounted on extension 501 of handle 375, whereby to limit the depth that shaft 370 can penetrate tissue (i.e., before the distal end of sheath 383 contacts the tissue and prevents further distal movement of shaft 370). In one form of the invention, the distance between distal end 490 of sheath 383 and sharp point 400 of shaft 370 is 18 mm when sheath 383 is mounted on extension 501 of handle 375.

Figure 54:
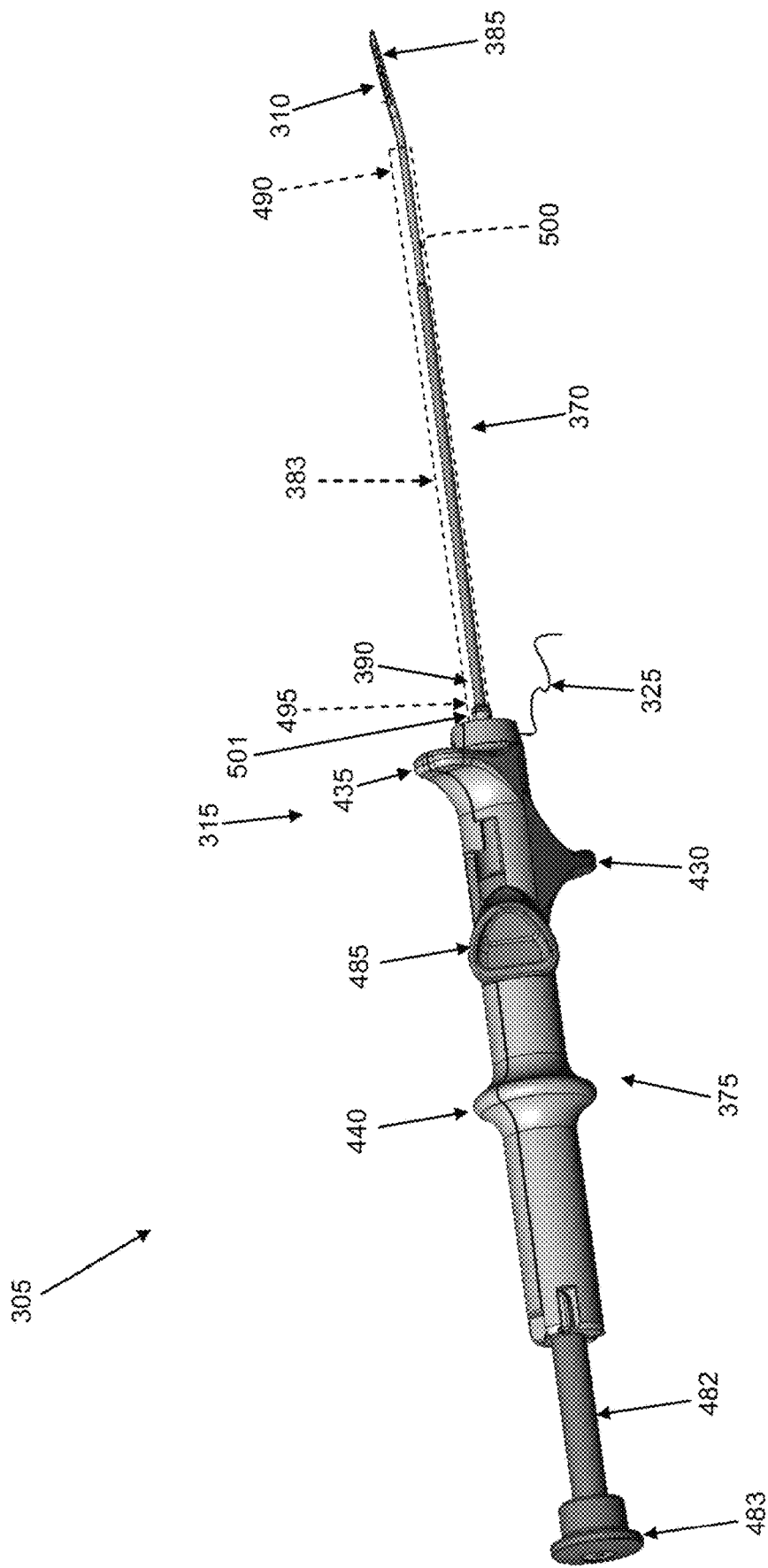
FIGS. 54 and 55 are schematic views showing an embodiment of a system formed in accordance with the present invention, wherein the system includes an anchor assembly and an inserter.
Figure 55:
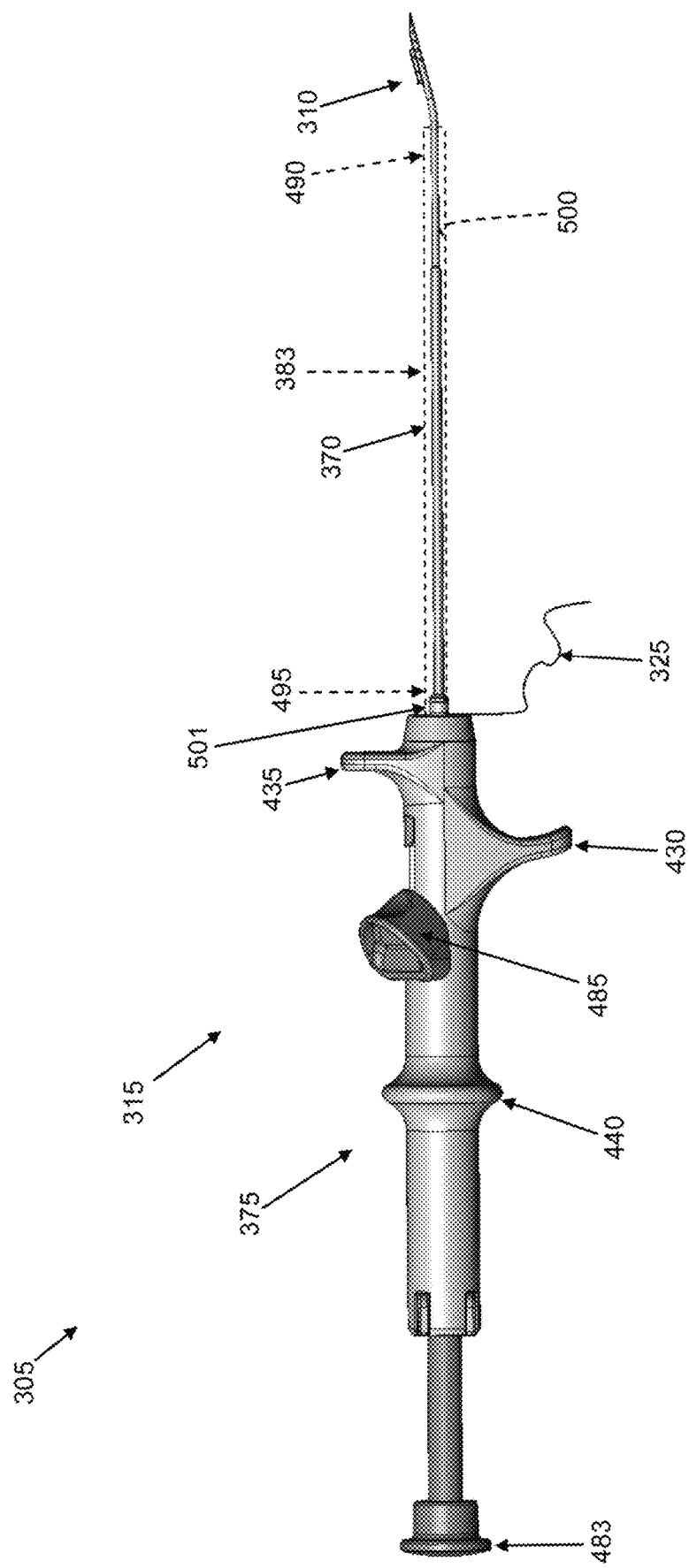
Figure 56:
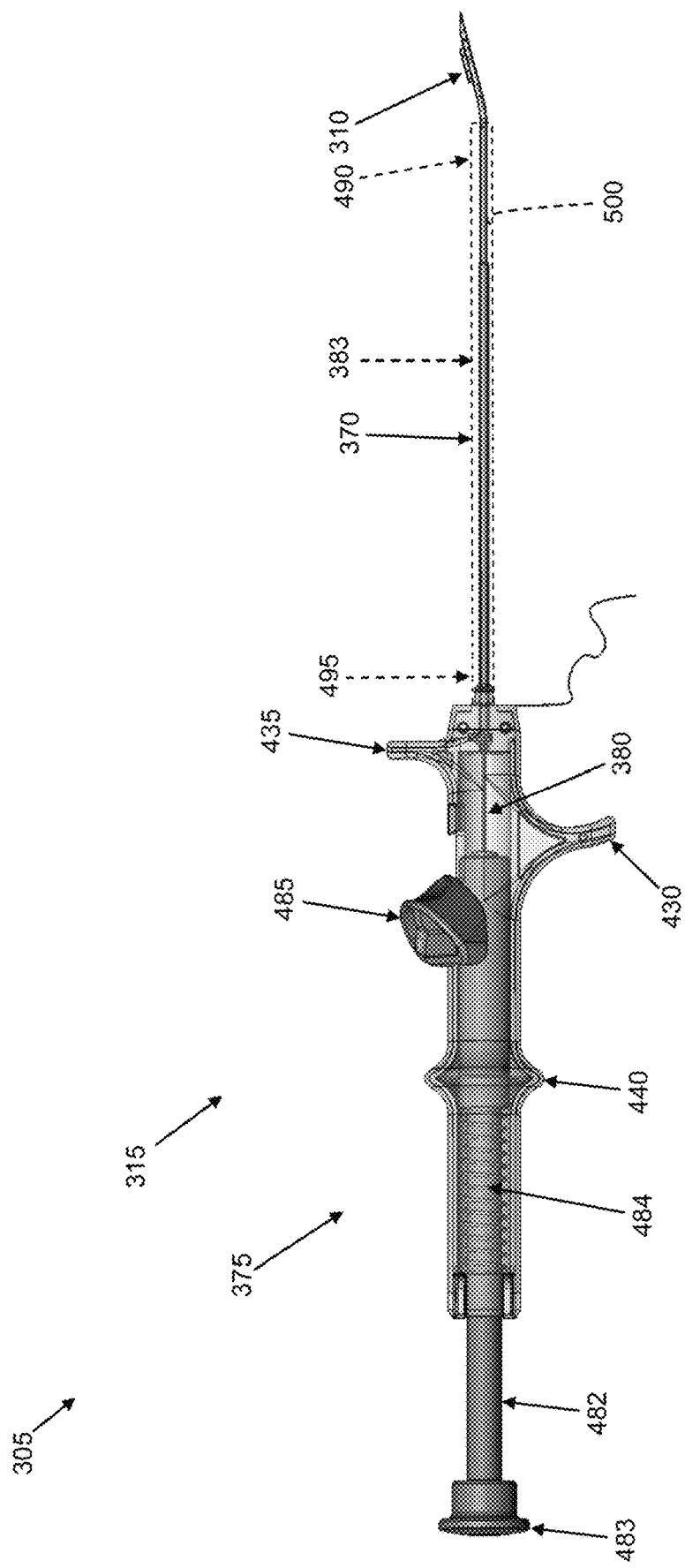
FIG. 56 is another illustration of the embodiment of FIGS. 54 and 55 where the housing of the inserter is transparent for ease of illustration.

In one embodiment of the invention, when anchor assembly 310 is mounted in the distal end of shaft 370, the free end of suture 325 extends out through slot 405 in shaft 370, enters lumen 500 of sheath 383, extends proximally through sheath 383, and out the proximal end 495 of sheath 383 (e.g., as illustrated in FIGS. 54-56). When sheath 383 is releasably mounted on extension 501 of handle 375, the proximal end of suture 325 may be releasably "pinched" between proximal end 495 of sheath 383 and handle 375, whereby to releasably hold the free end of suture 325 to inserter 315.

In use, in one embodiment, system 305 is initially in the state where button actuator 485 is disposed in first portion 450 of slot 445, with spring 484 urging cylinder 475 of pushrod assembly 380 distally towards first shoulder 465, and with first shoulder 465 preventing button actuator 485 from moving out of first portion 450 of slot 445. Anchors 320 of anchor assembly 310 are disposed in the distal end of shaft 370, just proximal to dimple 415. In this state, the distal end of pusher 480 is proximal to, or just engaging, the proximal end of proximal anchor 320B, and may not apply significant distally-directed force to proximal anchor 320B. Sheath 383 is disposed over shaft 370, with the proximal end of sheath 383 releasably secured to extension 501 of handle 375. With sheath 383 in this position, suture 325 extends proximally through lumen 500 of sheath 383 and, upon exiting the proximal end 495, can be pinched between the proximal end 495 of sheath 383 and handle 375.

Figure 57:
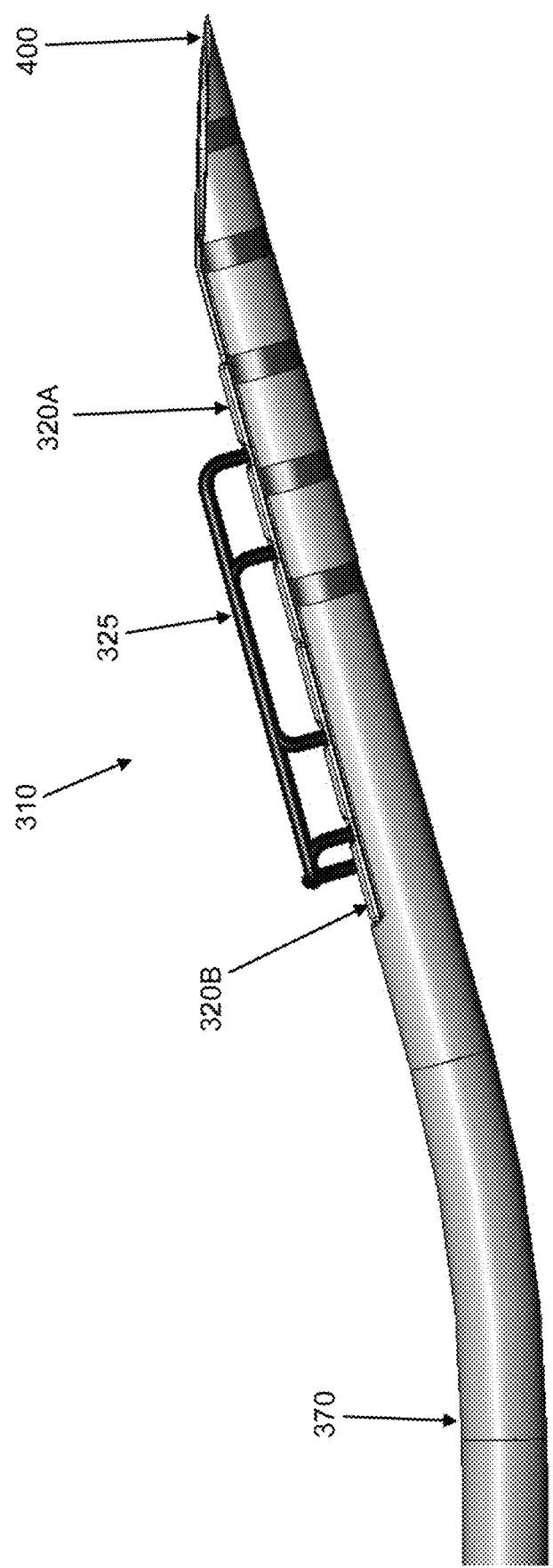
FIGS. 57-59 illustrate a schematic of the distal portion of the inserter and the anchor assembly and further wherein portions of the anchor assembly (i.e., the terminus knot and the slip knot) are shown in schematic form for clarity of illustration.

When anchors 320 are to be deployed in the body, sheath 383 can be advanced distally so as to cover the distal tip of shaft 375 (e.g., in order to prevent shaft 370 from getting caught on the tissue or causing damage to tissue or to limit the chance that portions of suture 325 extending through slot 405, as in FIGS. 57 and 58, could snag) while inserter 315 is advanced to an internal surgical site. If desired, inserter 315 may be advanced to an internal surgical site through a surgical cannula (e.g., a plastic arthroscopic cannula). Note that as the distal end of inserter 315 is advanced to the internal surgical site, with sheath 383 positioned distally and over sharp point 400 of shaft 370, it protects the surgical cannula and intervening tissue from the sharp point 400.

Once the distal end of inserter 315 has reached the internal surgical site, sheath 383, if positioned distally during insertion of inserter 315, is retracted proximally, e.g., so as to be re-seated on extension 501 of handle 375 (at this point, sheath 383 may or may not capture suture 325 to the proximal end of handle 375). Then inserter 315 is maneuvered such that the distal end of shaft 370 is passed through an object (e.g., tissue) at a first location, with the distal end of sheath 383 limiting the extent of distal advancement as the distal end of sheath 383 engages the object. Then button actuator 485 is advanced from first portion 450 of slot 445 into second portion 455 of slot 445, i.e., by pulling proximally on button actuator 485 (or end cap 483) against the power of spring 484 so as to cause button actuator 485 to clear first shoulder 465 and projection 466, rotating button actuator 485 (or end cap 483) circumferentially, and then advancing button actuator 485 (using either actuator 485 or end cap 483) distally along second portion 455 of slot 445 until button actuator 485 engages second shoulder 470. The user can either release the actuator 485 (or proximal extension 482) to allow the spring to force the actuator 485 distally through the second portion 455, or the user can control the movement of the actuator through the second portion 455. Either way, this action advances cylinder 475 distally such that pusher 480 contacts proximal anchor 320B and/or pushes proximal anchor 320B (and hence distal anchor 320A) distally, whereby additional distal force by the user deploys distal anchor 320A out of the distal end of shaft 360. Note that second shoulder 470 prevents button actuator 485 from advancing so far as to cause deployment of proximal anchor 320B from shaft 360.

At this point a slight proximal force may be applied to suture 325, whereby to snug proximal anchor 320A into position relative to the object (e.g., tissue) and to remove undesired slack from suture 375.

Shaft 370 is then withdrawn from the object (e.g., tissue), i.e., by moving inserter 315 proximally, inserter 315 is moved laterally (i.e., to any location other than the first location) to a second location relative to the object, and then the distal end of shaft 370 is advanced through the object (e.g., tissue) at the second location. Button actuator 485 is then advanced from second portion 455 of slot 445 into third portion 460 of slot 445, i.e., by pulling proximally on button actuator 485 (or end cap 483) so as to clear second shoulder 470 and ramp 471 (a distal spring force may or may not be present from spring 484 during this step), rotating button actuator 485 (or end cap 483) circumferentially, and then advancing button actuator 485 distally along third portion 460 of slot 445, until button actuator 485 engages the distal end of third portion 460 of slot 445. This action advances cylinder 475 distally, such that pusher 480 contacts proximal anchor 320B and deploys proximal anchor 320B out of the distal end of shaft 370. The third portion 460 dead-ends which may prevent the pusher from extending distally from shaft and damaging surrounding tissue.

Shaft 370 is then withdrawn from the object (e.g., tissue), i.e., by moving inserter 315 proximally, and then the proximal end of suture 325 is pulled proximally whereby to snug distal anchor 320B into position relative to the object (e.g., tissue) and to cinch slip knot 365, whereby to set the expanse of suture extending between distal anchor 320A and proximal anchor 320B. In this way anchors 320A, 320B can be used to hold two or more objects together within the body of a patient, such as in re-approximating soft tissue portions or securing an implant to soft tissue.

Figure 77:
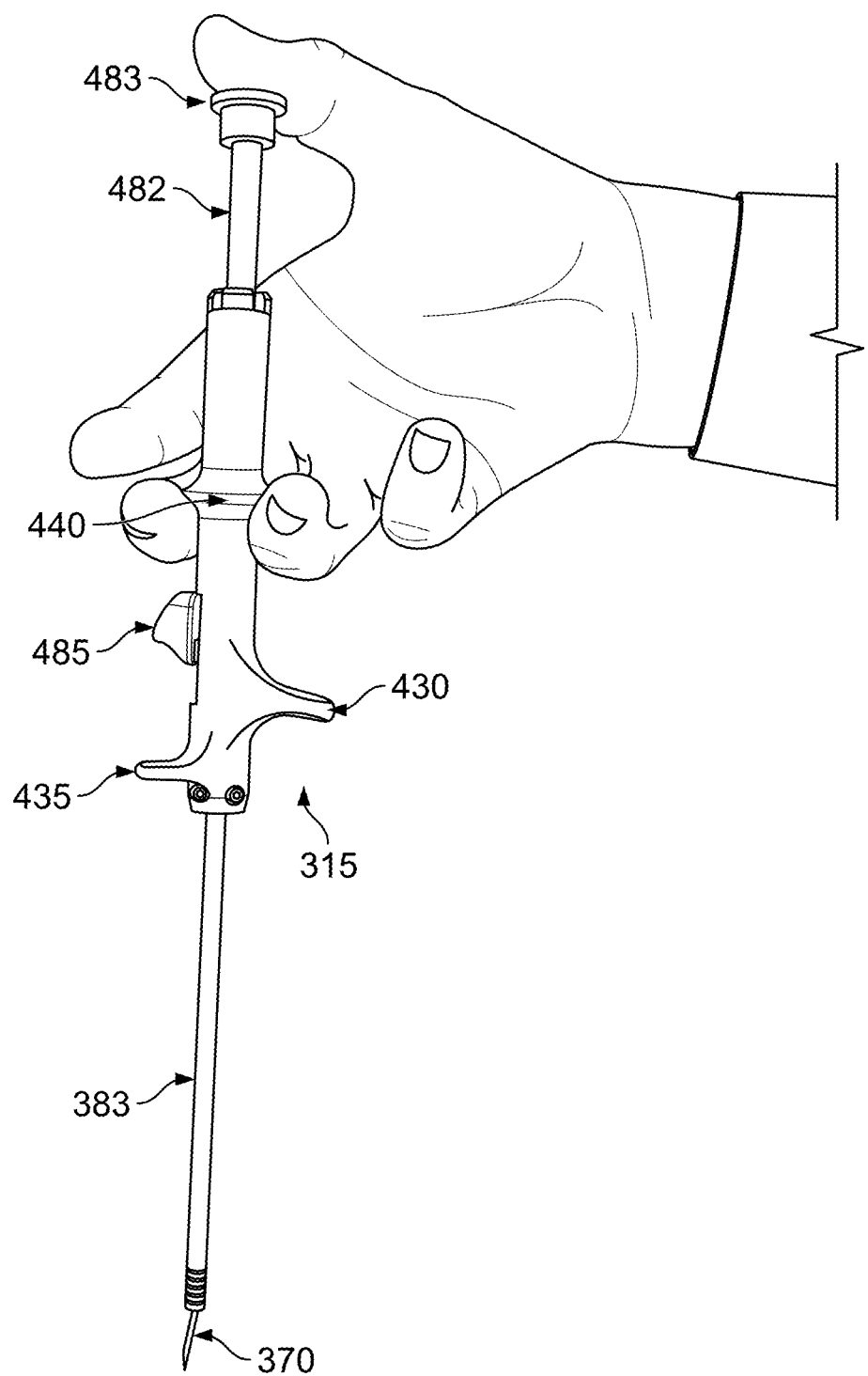

Significantly, with the present invention, the user has the option of holding (and actuating) inserter 315 with a variety of grips. By way of example but not limitation, and looking now at FIG. 76, the user may hold inserter 315 so that the index finger engages first grip 430, the thumb engages second grip 435 or button actuator 485, and/or the middle, ring and little finger wrap around the barrel of body 420 of handle 375. This manner of holding inserter 315 is somewhat analogous to the manner in which a user might hold a steak knife or a pool cue. Alternatively, in another example and looking now at FIG. 77, the surgeon may hold inserter 315 so that the middle and ring fingers engage third grip 440 and the thumb engages end cap 483. This manner of holding inserter 315 is somewhat analogous to the manner in which a user might hold a syringe.

Figure 78:
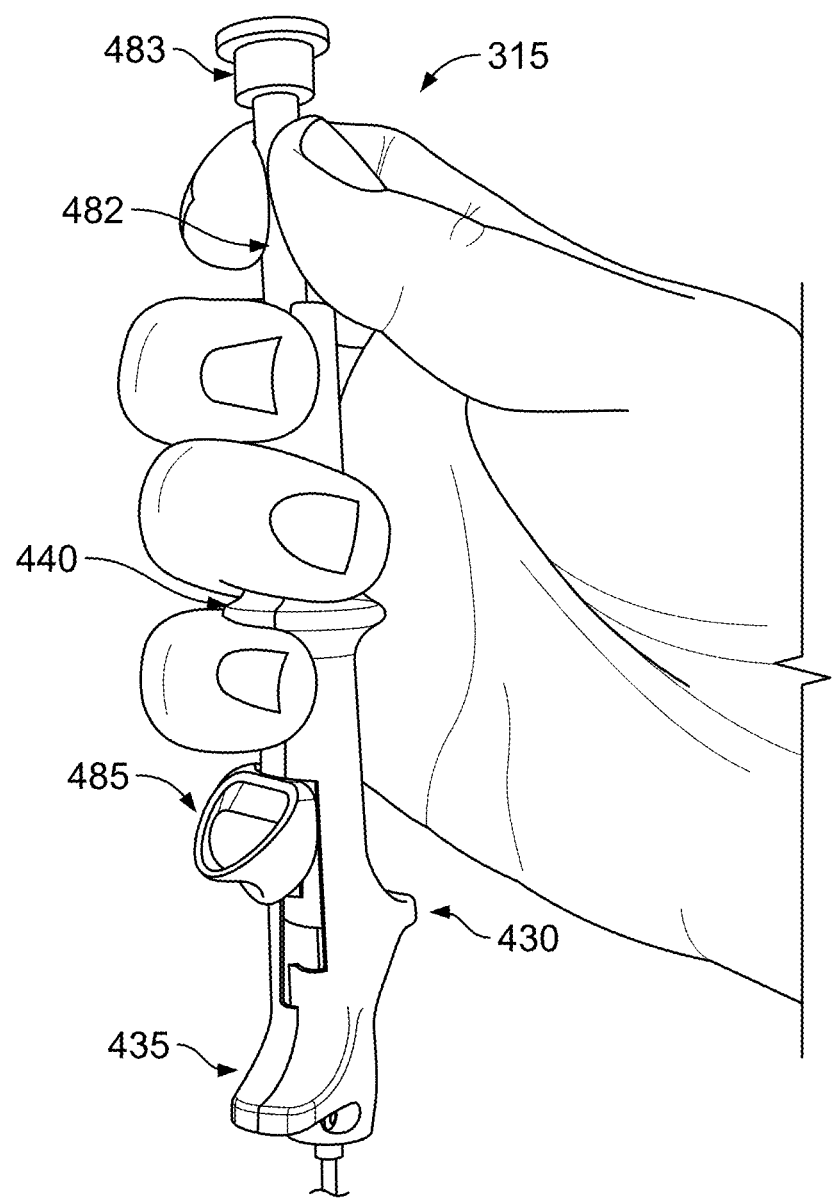
Figure 79:
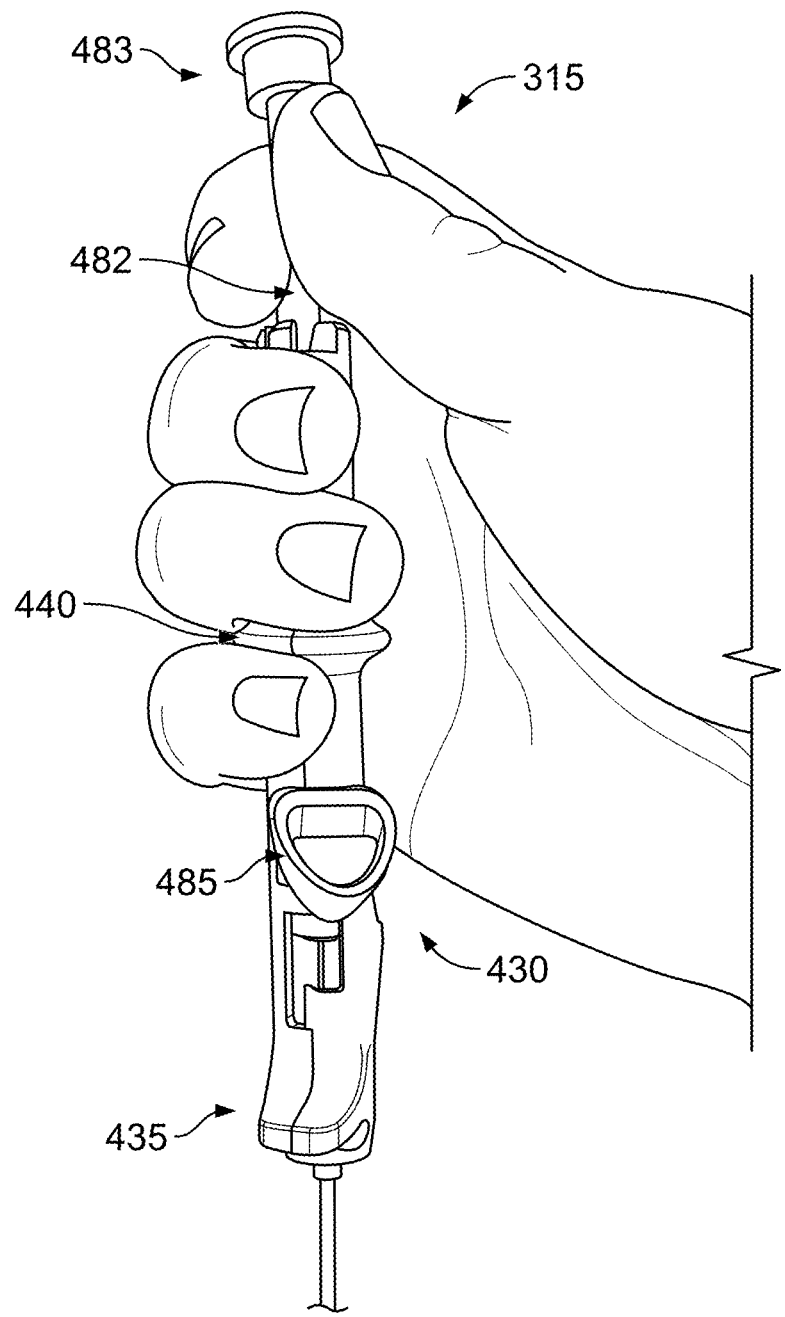
Figure 80:
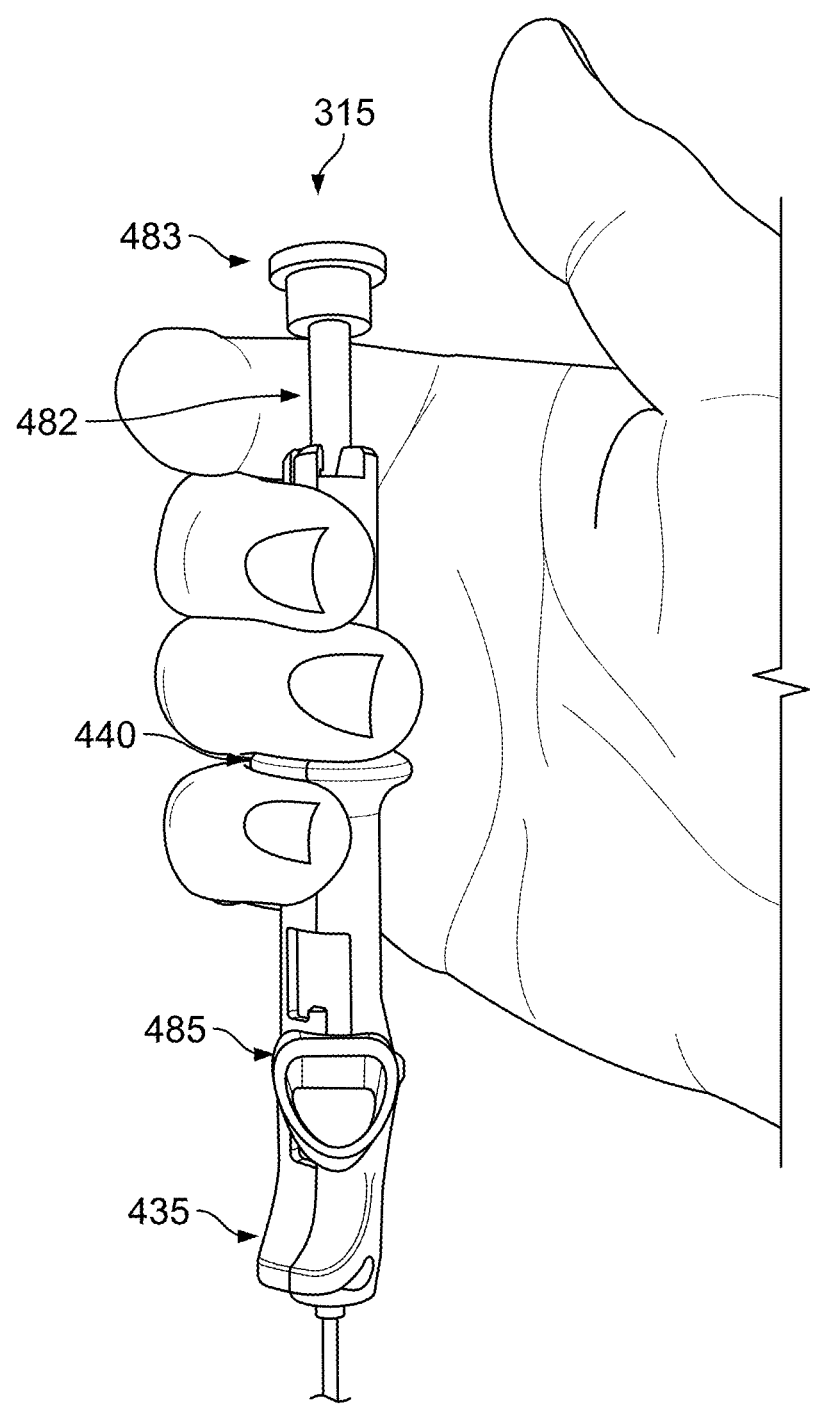
Figure 81:
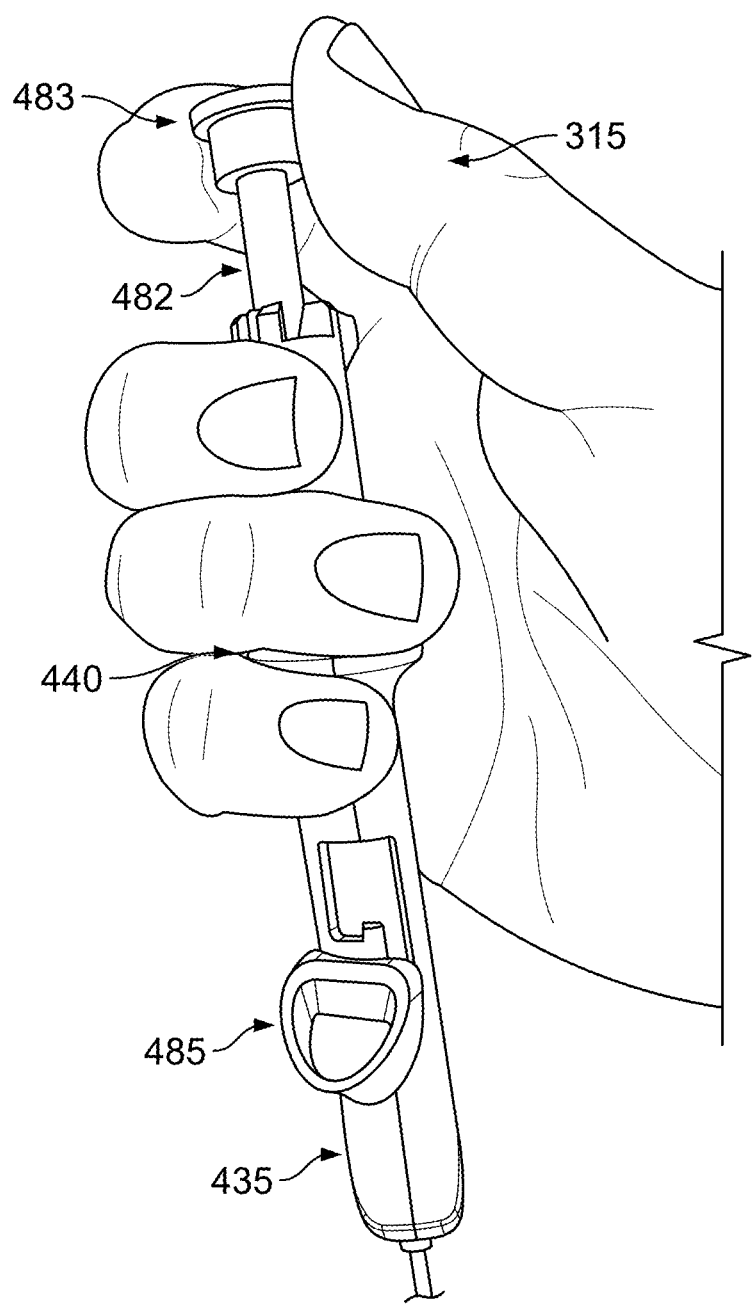
Figure 82:
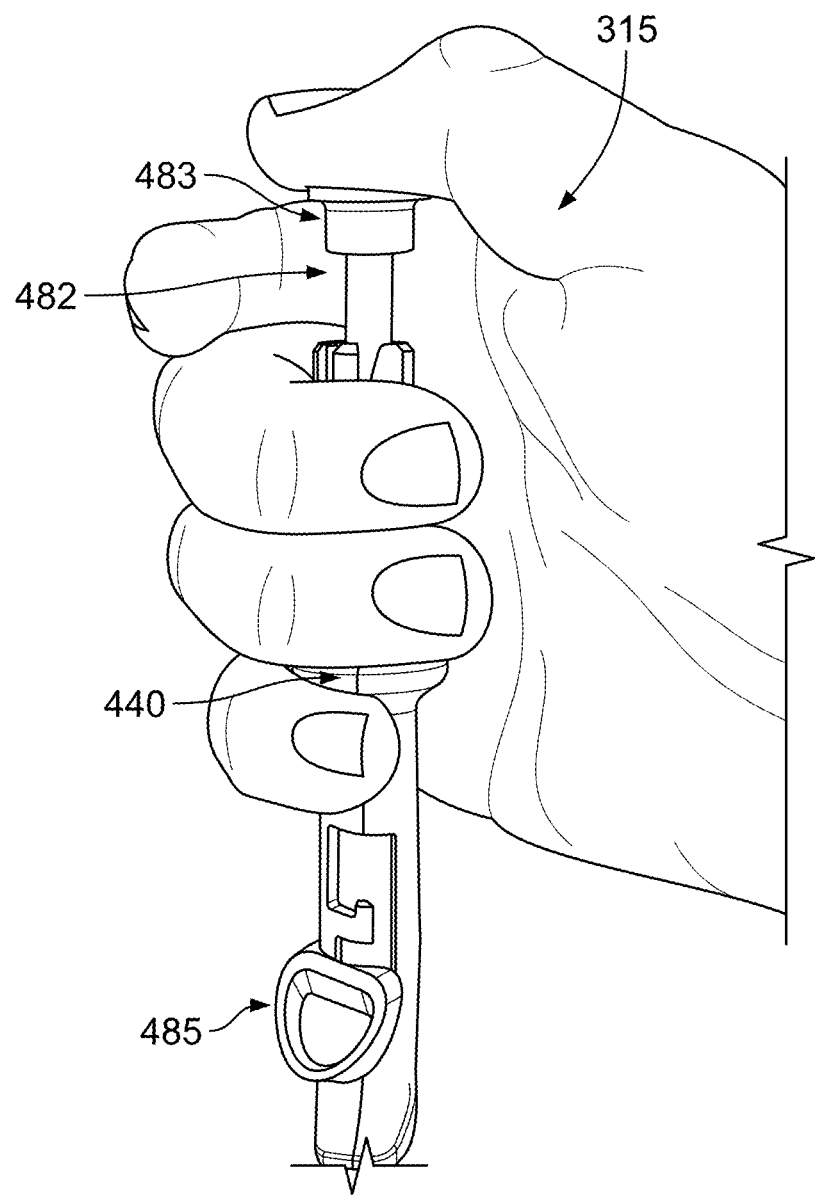

In still another alternative example, as illustrated in FIGS. 78-82, the surgeon may hold the inserter 315 like a ballpoint pen. In this exemplary use (based on the discussion herein), the surgeon may engage the extension 482 and/or the end cap 483 between thumb and index finger, with the other three fingers wrapped around handle 375 such that third grip 440 is positioned between two fingers (such as pinkie and ring fingers, as illustrated in FIGS. 78, 79 and 81). This grip allows for both rotation of extension 482, and thus actuator 485, and, by pressing on the proximal surface of the end cap 483 with the thumb (FIG. 82), axial movement of the extension 482, and thus pusher to deploy the anchors. As illustrated in FIG. 80, the extension 482 may be released while the actuator 485 is positioned within the second portion 455, such that spring 484 automatically moves actuator 485, and thus pusher 480 distally. However, spring 484 may not have sufficient force to eject the distal anchor from shaft 370. Such a spring force may decrease the risk of accidental deployment of the distal anchor, such that depression of the thumb on end cap 483 is required for actual deployment.

It should also be appreciated that, inasmuch as shaft 370 is fixed to handle 375 and inasmuch as anchors 320 are fixed against rotation relative to shaft 370 (i.e., by virtue of upraised portions 335 of anchors 320 being disposed in slot 405 of shaft 370), the position of first grip 430 and second grip 435 of handle 375 indicate the rotational disposition of anchors 320 within shaft 370 even when the distal end of shaft 370 is disposed at a remote location within the body. And it should also be appreciated that where shaft 370 is curved, the position of first grip 430 and second grip 435 of handle 375 also indicate the orientation of the curvature of shaft 370.

In another embodiment, the present invention includes a method of packaging the inserter 315 including positioning the actuator 485 against the first stop 465 to prevent movement of the actuator 485 relative to the handle 375, optionally sterilizing the inserter 315 and/or packaging, and packaging the inserter 315 in at least one layer of packaging. The inserter 315 may also include the anchor assembly 310 positioned within the shaft 370 and ready for use. The packaging may also include an instructions for use or surgical technique document detailing at least one surgical method for which inserter 315 may be used.

It will be appreciated that certain changes may be made to novel system 305 without departing from the scope of the present invention. By way of example but not limitation, the configuration of anchor assembly 310 may be modified, e.g., the configuration and/or number of anchors 320 may be modified, terminus knot 360 may comprise a knot different than that disclosed, slip knot 365 may comprise a slip knot different than that disclosed above, etc. By way of further example but not limitation, the configuration of inserter 315 may be modified from that disclosed.

The foregoing disclosure of embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. For example, any number of sutures may be prepared ahead of time. In addition, the advancement of the anchors within the cannula may occur before or after needle insertion. In addition, the delivery of the second anchor may not require that the needle be fully withdrawn; for example when two anchors are to be delivered through a single insertion site. As one of ordinary skill in the art would appreciate, other sequences of steps may be possible. Therefore, the particular order of the steps set forth herein should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

It should be understood that many additional changes in the details, materials, steps and arrangements of parts, which have been herein described and illustrated in order to explain the nature of the present invention, may be made by those skilled in the art while still remaining within the principles and scope of the invention.

The invention claimed is:

1. A method of using an inserter, comprising:
inserting a shaft of the inserter into soft tissue, a first anchor and a second anchor received within the shaft, a length of suture connecting the first anchor and the second anchor, the inserter including a housing and an implant push rod, the push rod connected to an actuator and an actuator extension, the actuator extension extending from a proximal end of the housing and the actuator extending from a side of the housing, wherein the housing includes a biasing element between the actuator and the actuator extension positioned longitudinally relative to a longitudinal axis defined by the housing, wherein the actuator extension is a most proximal feature of the inserter;
engaging the actuator or the actuator extension to slide the push rod towards a distal end of the housing of the inserter to expel the first anchor from an open distal end of the shaft;
engaging the actuator or the actuator extension to slide the push rod towards the proximal end of the housing after the first anchor is expelled; and engaging the actuator or the actuator extension to slide the push rod towards the distal end of the housing to expel the second anchor from the open distal end of the shaft after the push rod is slid towards the proximal end of the housing.

2. The method of claim 1, wherein sliding the push rod towards the proximal end of the housing provides a tactile response.

3. The method of claim 1, wherein sliding the push rod includes overcoming a biasing force of the biasing element.

4. The method of claim 1, wherein the housing and actuator facilitates engagement of the inserter with a syringe-type grip, wherein the housing and the actuator extension facilitates engagement of the inserter with a ballpoint pen-type grip.

5. The method of claim 4, wherein sliding the push rod includes manipulating a cap at a proximal end of the actuator extension.

6. The method of claim 1, wherein sliding the push rod includes sliding the actuator and the actuator extension along a same direction.

7. A method of using an inserter, comprising:
inserting a shaft of the inserter into a soft tissue, a first anchor and a second anchor received within the shaft, a length of suture connecting the first anchor and the second anchor, the inserter including a housing and an implant push rod, the push rod connected to an actuator and an actuator extension, the actuator extension extending from a proximal end of the housing and a thumb actuator extending from a side of the housing, wherein the housing includes a biasing element between the actuator and the actuator extension positioned longitudinally relative to a longitudinal axis defined by the housing, wherein the actuator extension is a most proximal feature of the inserter;
engaging the actuator or the actuator extension to slide a push rod in a first direction to expel the first anchor from an open distal end of the shaft; and
engaging the actuator or the actuator extension to slide the push rod in a second direction after the first anchor is expelled, the second direction being different than the first direction; and
engaging the actuator or the actuator extension to slide the push rod in the first direction to expel the second anchor from the open distal end of the shaft after the push rod is slid towards the second direction.

8. The method of claim 7, wherein sliding the push rod in a second direction provides a tactile response.

9. The method of claim 7, wherein sliding the push rod includes overcoming a biasing force of the spring biasing element.

10. The method of claim 7, wherein the housing and actuator facilitates engagement of the inserter with a syringe-type grip, wherein the housing and the actuator extension facilitates engagement of the inserter with a ballpoint pen-type grip.

11. The method of claim 7, wherein sliding the push rod includes manipulating a cap at a proximal end of the actuator extension.

12. The method of claim 7, wherein sliding the push rod includes sliding the actuator and the actuator extension along a same direction.

13. A method of using an inserter for meniscus surgery, comprising:
inserting a portion of a shaft of the inserter into meniscus tissue, a first anchor and a second anchor received within the shaft, a length of suture connecting the first anchor and the second anchor, the inserter including a housing and an implant push rod, the push rod connected to an actuator and an actuator extension, the actuator extension extending from a proximal end of the housing and a thumb actuator extending from a side of the housing, wherein the housing includes a biasing element between the actuator and the actuator extension positioned longitudinally relative to a longitudinal axis defined by the housing, wherein the actuator extension is a most proximal feature of the inserter;
engaging the actuator or the actuator extension to slide a push rod in a first longitudinal direction to expel the first anchor from an open distal end of the shaft through the meniscus tissue; and
engaging the actuator or the actuator extension to slide the push rod in a second longitudinal direction after the first anchor is expelled, the second direction being different than the first direction; and
engaging the actuator or the actuator extension to slide the push rod in the first longitudinal direction to expel the second anchor through the meniscus tissue after the push rod is slid towards the second longitudinal direction.

14. The method of claim 13, wherein actuating the push rod in a second direction provides a tactile response.

15. The method of claim 13, wherein actuating the push rod includes overcoming a biasing force of the biasing element.

16. The method of claim 13, wherein the housing and the actuator facilitates engagement of the inserter with a syringe-type grip, wherein the housing and the actuator extension facilitates engagement of the inserter with a ballpoint pen-type grip.

17. The method of claim 13, wherein actuating the push rod includes manipulating a cap at a proximal end of the actuator extension.

18. The method of claim 13, wherein actuating the push rod includes actuating the actuator and the actuator extension along a same direction.

* * * * *